US009540369B2

(12) United States Patent
Striker et al.

(10) Patent No.: US 9,540,369 B2
(45) Date of Patent: Jan. 10, 2017

(54) USE OF KINASE INHIBITORS TO INCREASE THE SUSCEPTIBILITY OF GRAM POSITIVE BACTERIA TO BETA LACTAM ANTIBIOTICS

(71) Applicant: Wisconsin Alumni Research Foundation, Madison, WI (US)

(72) Inventors: Robert Todd Striker, Madison, WI (US); John-Demian Sauer, Madison, WI (US); Nathan Wlodarchak, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/695,813

(22) Filed: Apr. 24, 2015

(65) Prior Publication Data

US 2015/0307495 A1    Oct. 29, 2015

Related U.S. Application Data

(60) Provisional application No. 62/034,916, filed on Aug. 8, 2014, provisional application No. 61/984,277, filed on Apr. 25, 2014.

(51) Int. Cl.
| | | |
|---|---|---|
| *C07D 401/14* | (2006.01) | |
| *A61K 31/437* | (2006.01) | |
| *C07D 471/04* | (2006.01) | |
| *C07D 487/04* | (2006.01) | |

(52) U.S. Cl.
CPC .......... *C07D 471/04* (2013.01); *C07D 487/04* (2013.01)

(58) Field of Classification Search
CPC .......................... C07D 401/14; A61K 31/437
USPC .......................................... 546/119; 514/303
See application file for complete search history.

(56) References Cited

U.S. PATENT DOCUMENTS 7,625,890 B2 * 12/2009 Heerding ............. C07D 471/04
 514/228.5

* cited by examiner

*Primary Examiner* — Niloofar Rahmani
(74) *Attorney, Agent, or Firm* — Boyle Fredrickson, S.C.

(57) ABSTRACT

Methods of using certain kinase inhibitors for treating Gram positive bacterial infections are disclosed. When co-administered with a β-lactam antibiotic, the disclosed compounds increase the susceptibility of infectious Gram positive bacteria to the β-lactam antibiotic.

The disclosed kinase inhibitors have either of the general formulas:

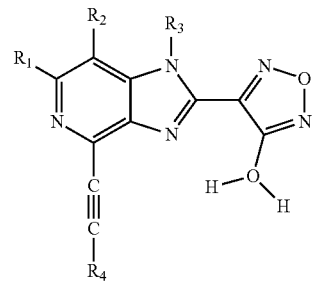

or

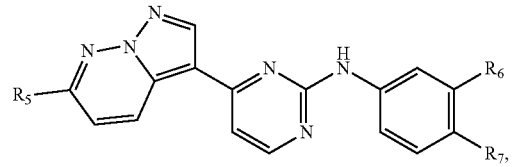

or the specific formula:

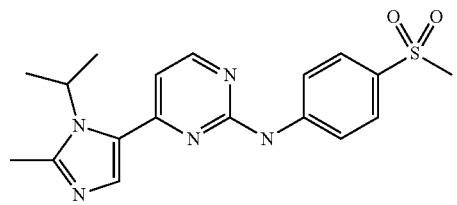

9 Claims, 58 Drawing Sheets
(30 of 58 Drawing Sheet(s) Filed in Color)

USE OF KINASE INHIBITORS TO INCREASE THE SUSCEPTIBILITY OF GRAM POSITIVE BACTERIA TO BETA LACTAM ANTIBIOTICS

CROSS-REFERENCE TO RELATED APPLICATIONS

This application claims the benefit of U.S. provisional Application No. 61/984,277 filed on Apr. 25, 2014, and U.S. provisional Application No. 62/034,916 filed on Aug. 8, 2014. Each of these applications is incorporated by reference herein in its entirety.

STATEMENT REGARDING FEDERALLY FUNDED RESEARCH AND DEVELOPMENT

This invention was made with government support under AI057153 awarded by the National Institutes of Health. The government has certain rights in the invention.

FIELD OF THE INVENTION

This invention relates generally to the treatment of bacterial infections. More particularly, the present invention is directed to compounds that can be administered along with β-lactams to treat Gram-positive bacterial infections. The disclosed compounds increase the susceptibility of the infectious bacteria to β-lactams, and thus increase the effectiveness of β-lactams as antibacterial therapeutics.

BACKGROUND OF THE INVENTION

*Listeria monocytogenes* is a common environmental Gram-positive bacterium that upon ingestion can cause the serious disease listeriosis (1). Listeriosis is normally contracted from ingestion of contaminated food by at risk populations which include the elderly, the immunocompromised and pregnant women (2-3). Disease symptoms can range from mild gastroenteritis to severe meningitis and spontaneous miscarriage (4). Current therapy calls for high dose aminopenicillins combined with gentamicin (5). Although *L. monocytogenes* is highly susceptible to this treatment in vitro, the fatality rate from confirmed cases of listeriosis remains high, sometimes reaching ~30%, suggesting an increased need for better therapeutic strategies for treating listeriosis (6-7).

β-lactam antibiotics have been a critical part of treatment for Gram-positive bacterial infections since they were discovered (8). Unfortunately, due to the increasing frequency of antibiotic resistance, β-lactams are no longer effective against many pathogens, including certain penicillin resistant Streptococci and Enterococci, and most notoriously Methicillin-Resistant *Staphylococcus aureus* (MRSA) (9). MRSA strains, including the community associated strains such as USA300, contain the mecA gene which encodes the Penicillin Binding Protein 2A (PBP2A), a PBP that confers resistance to all approved β-lactams with the exception of ceftaroline (10-11). Similarly, resistance to drugs targeting *Mycobacterium tuberculosis* has been on the increase worldwide, motivating the search for new methods for identifying drug targets and understanding resistance mechanisms in *Mycobacterium tuberculosis* (see, e.g., Ioerger, Thomas R., et al., Identification of new drug targets and resistance mechanisms in *Mycobacterium tuberculosis*, PLOS One 8(9), September 2013, e75245, p. 1-13). The alarming increase in the development of antibiotic resistance, particularly to β-lactams, has resulted in a need for new strategies for antimicrobial therapy.

Despite this widely acknowledged need, truly novel antibiotic classes have not been developed for decades. Collectively, the cell wall active β-lactams (various penicillins, cephalosporins, monolactams, and carbapenems) have been the most prescribed antibiotics worldwide since penicillin was discovered and remain so today, despite increasing resistance.

*S. aureus*, and many other important pathogens, including *L. monocytogenes, Mycobacterium tuberculosis* and *Enterococcus faecalis*, express a bipartite membrane-associated eukaryotic-like serine/threonine kinase that has one or more extracellular repeat of a homologous family of PBPs (12). This family of proteins is known as the Penicillin binding protein and Serine-Threonine kinase associated protein (PASTA) kinases (12). PASTA kinases have extracellular penicillin binding domains that have previously been shown to bind fragments of peptidoglycan, likely generated by cell wall damage or remodeling, and an intracellular serine threonine kinase domain, similar to those found in eukaryotic cells (13).

While the substrates and function of the PASTA kinases are incompletely defined, they appear to have varied functions in different organisms ranging from playing a role in biofilm formation (*Streptococcus mutans*) to being essential in some organisms (*M. tuberculosis*) (14-15). Deletion of Stk1, the PASTA kinase in *S. aureus*, reverses the methicillin resistant phenotype in MRSA (16-17). In addition, deletion of the PASTA kinase in *E. faecalis*, PrkC, led to a >100-fold sensitization to certain β-lactam antibiotics (18). However, the mechanism for this effect remains unclear.

Rajagapol et al. (WO 2013/066469) disclose the use of certain kinase inhibitors to increase the sensitivity of bacterial pathogens to β-lactam antibiotics. As is well-known in the art, kinase inhibitors encompass a large family of compounds that vary substantially in structure, specific target, and targeting mechanism, and the successful use of a specific kinase inhibitor for a given therapeutic purpose can not be predictably applied to other kinase inhibitors. This is particularly true for inhibitors having a substantially different core structure than those that have been previously disclosed. Thus, there is a need in the art for other compounds that can be used to increase the susceptibility of bacterial pathogens to β-lactam antibiotics.

SUMMARY OF THE INVENTION

The present invention relates to the inventors' identification of a small number of kinase inhibitors screened from a large number of such inhibitors that can increase the susceptibility of MRSA, *Listeria* bacteria, *Mycobacterium* bacteria, or a combination thereof to β-lactam antibiotics. The compounds identified include compounds and related analogs identified using an in silico docking model that form two separate scaffold formulas (alkyne imidazopyridine aminofurazans and pyrazolo[1,5-b]pyridazines).

Accordingly, in a first aspect, this disclosure provides a method of treating a Gram-positive bacterial infection in a subject in need thereof. The method includes the step of administering to the subject an effective amount of a compound having the chemical structure:

(a)

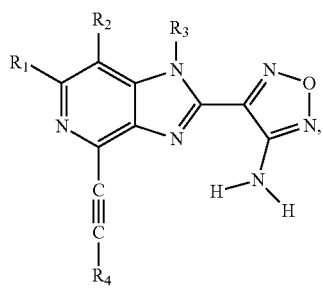

wherein one of $R_1$ and $R_2$ is H;

wherein the other of $R_1$ and $R_2$ is —OX, wherein X is selected from the group consisting of

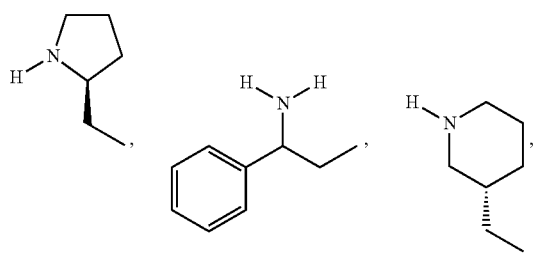

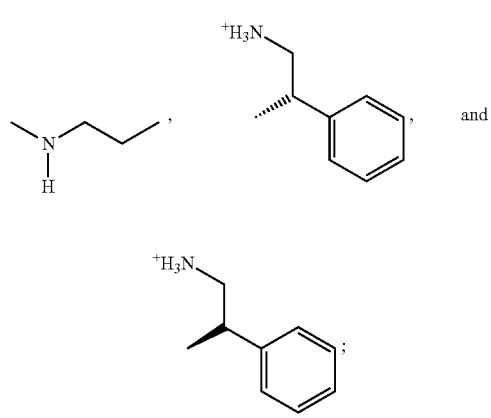

wherein $R_3$ is selected from the group consisting of —CH$_2$CH$_3$,

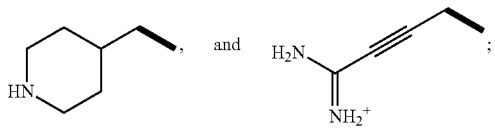

and wherein $R_4$ is selected from the group consisting of

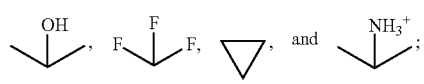

(b)

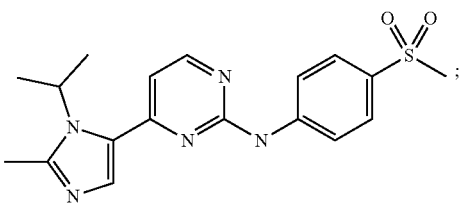

(c)

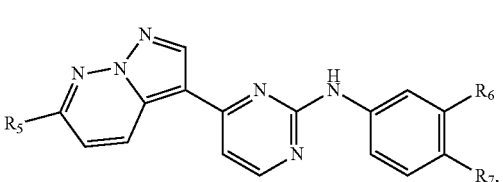

wherein $R_5$ is H or

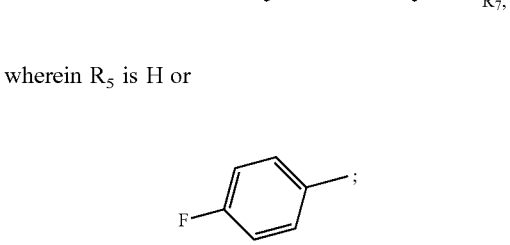

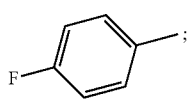

wherein $R_6$ is H or —CF$_3$; and
wherein $R_7$ is selected from the group consisting of

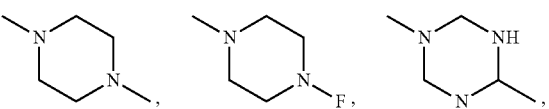

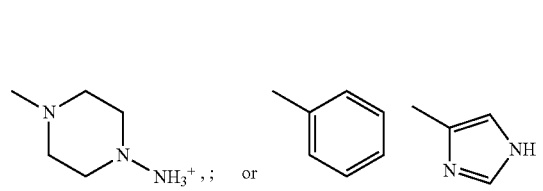

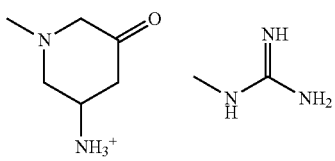

(d) a pharmaceutically acceptable salt of any of the structures shown in (a), (b) or (c). In performing the method, the extent of the Gram-positive bacterial infection is reduced in the subject.

In some embodiments, the compound administered is:

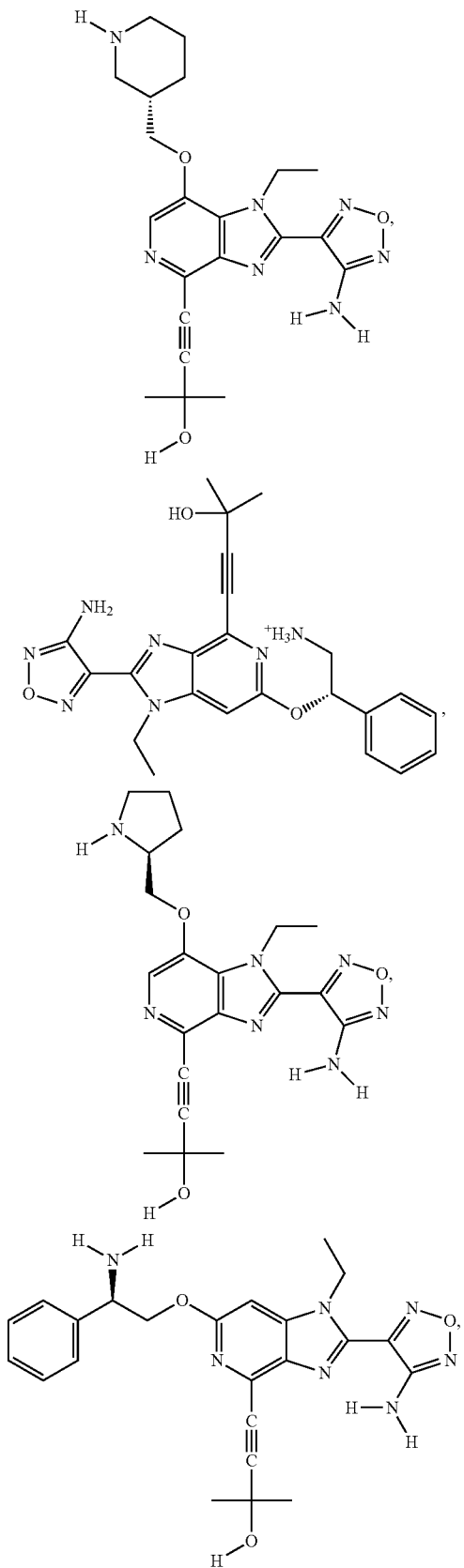

In some embodiments, the Gram positive bacterial infection is caused by *Listeria monocytogenes, Staphylococcus aureus, Streptococcus pneumonia, Mycobacterium tuberculosis, Nocardia farcinia,* a *Clostridium*, or an *enteroccci*. In some such embodiments, the Gram-positive bacterial infection is caused by *Mycobacterium tuberculosis, Listeria monocytogenes* or Methicillin Resistant *Staphylococcus aureus* (MSRA).

In some embodiments, the method further includes the step of administering a β-lactam antibiotic to the subject. In some embodiments, the β-lactam antibiotic is benzathine penicillin, benzylpenicillin (penicillin G), phenoxymethylpenicillin (penicillin V), procaine penicillin, methicillin, oxacillin, nafcillin, cloxacillin, dicloxacillin, flucloxacillin, temocillin, amoxicillin, ampicillin, co-amoxiclav, azlocillin, carbenicillin, ticarcillin, mezlocillin, piperacillin, cephalosporins, cephalexin, cephalothin, cefazolin, cefaclor, cefuroxime, cefamandole, cephamycins, cefotetan, cefoxitin, ceftriaxone, cefotaxime, cefpodoxime, cefixime, ceftazidime, cefepime, cefpirome, imipenem, meropenem, ertapenem, faropenem, doripenem, monobactams, aztreonam, tigemonam, nocardicin A, or tabtoxinine-P-lactam.

In a second aspect, the disclosure encompasses compounds having the formula:

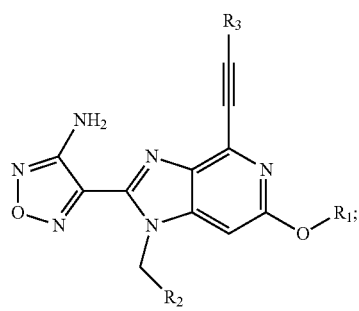

wherein R₁ is selected from the group consisting of

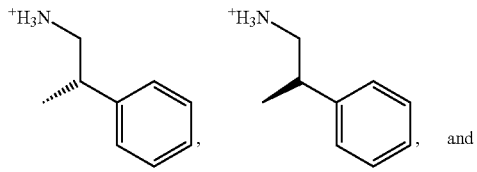
and

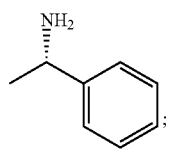
;

R₂ is selected from the group consisting of —CH₃,

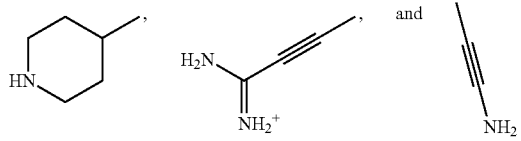
;

R₃ is selected from the group consisting of

;

wherein if R₂ is —CH₃, then R₃ is not

;

or a salt thereof. In some embodiments, the compound is included in a that also includes a pharmaceutically acceptable carrier.

In some embodiments, the compound has a structure selected from the group consisting of:

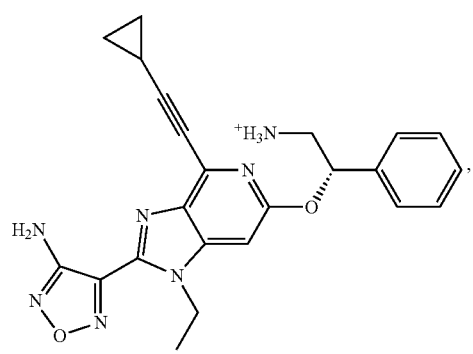

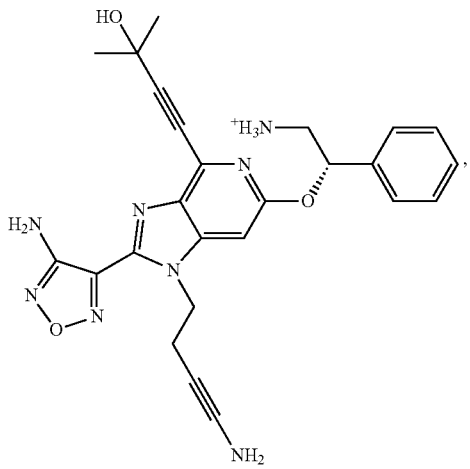

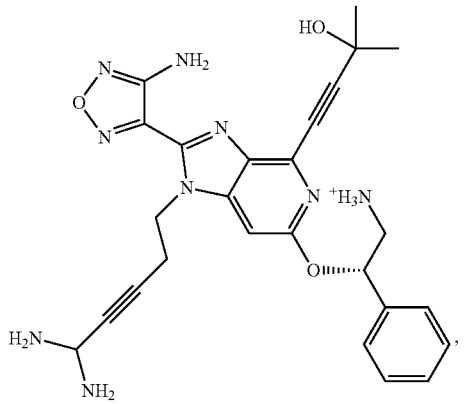

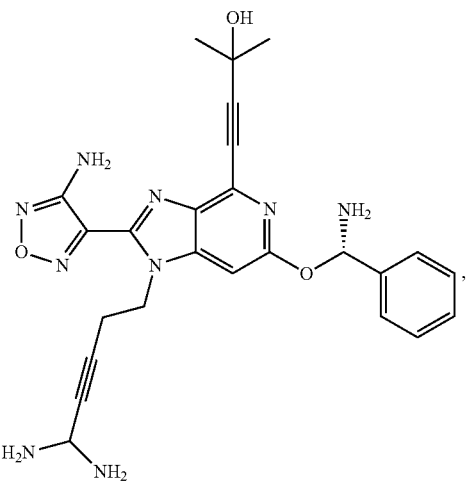

-continued

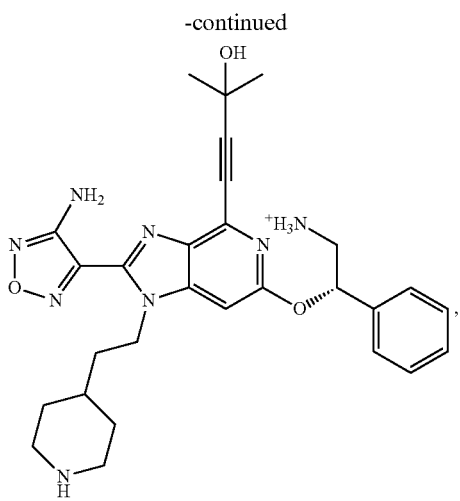

,

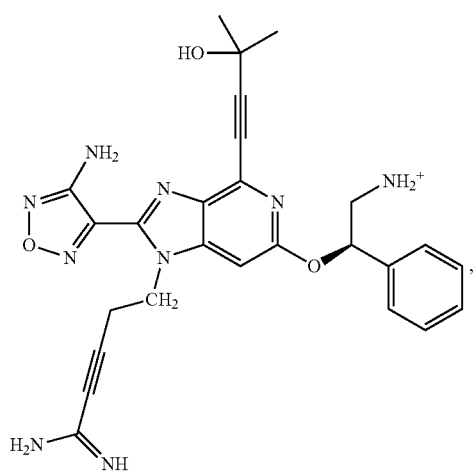

,

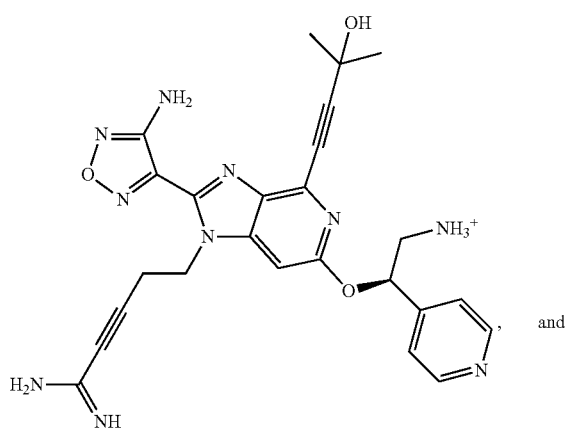

and

-continued

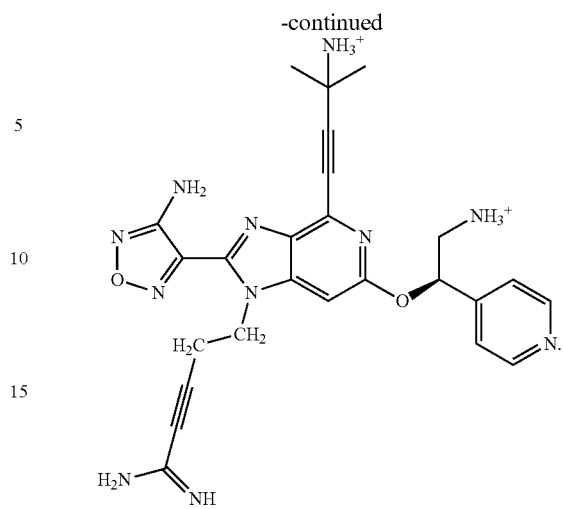

In third aspect, the disclosure encompasses compounds having the formula:

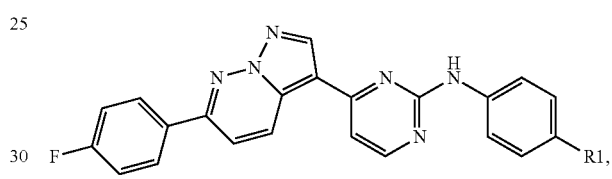

wherein R1 is selected from the group consisting of:

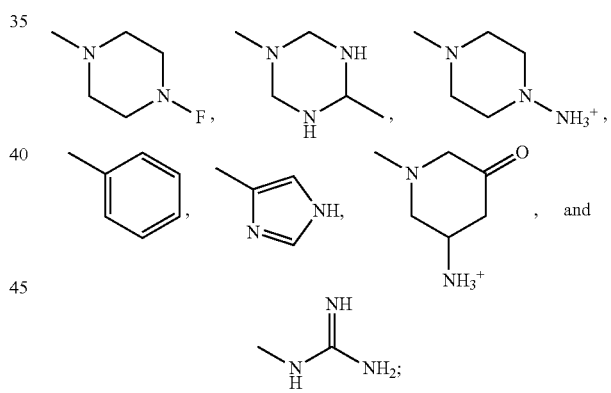

or a salt thereof.

In some embodiments, the compound is included in a composition with a pharmaceutically acceptable carrier.

Other objects, features and advantages of the present invention will become apparent after review of the specification, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows results with ampicillin in the presence (open shape) or absence (closed shape) of 10 μM staurosporine.

FIG. 1B shows results with ceftriaxone in the presence (open shape) or absence (closed shape) of 10 μM staurosporine.

FIG. 1C shows results with cefalexin in the presence (open shape) or absence (closed shape) of 10 μM staurosporine.

FIG. 1D shows results with vancomycin in the presence (open shape) or absence (closed shape) of 10 μM staurosporine.

FIG. 1E shows results with kanamycin in the presence (open shape) or absence (closed shape) of 10 μM staurosporine.

FIG. 5A. Overnight cultures of wild type L. monocytogenes were back diluted and treated with 10-fold serial dilutions of ceftriaxone in the presence (open shape) or absence (closed shape) of 50 μM AZD5438. Antibiotic concentrations are μg/ml. Growth was analyzed for 12 hours at 15 minute intervals. Data are representative of at least 3 independent repeats.

FIG. 5B. Autophosphorylation (arrow) and myelin basic protein (MBP) phosporylation (*) activity was assayed for PrkA (lanes 1-5), Lmo0618 (lanes 6-9), and S.a.Stk1 (lanes 10-11) in the presence or absence of 1μM, 10 μM or 100 μM AZD5438.

FIG. 39A shows the multiple interactions with the R1 group (FIG. 38) we will optimize. Similar interactions occur when compound 39 is modeled in the MRSA kinase. In FIG. 39B it is apparent that the F-phenyl R2 group packs well against residues of the bacterial kinase, but in FIG. 39C clashes with the dark loop of human CDK2 (see highlighted circle). In bacterial kinases this loop has some flexibility, but in human kinases it does not due to the presence of the pink loop residues 154-165 that pack down the glycine rich loop in the human kinases (FIG. 39C).

DETAILED DESCRIPTION OF THE INVENTION

Figure 1A:
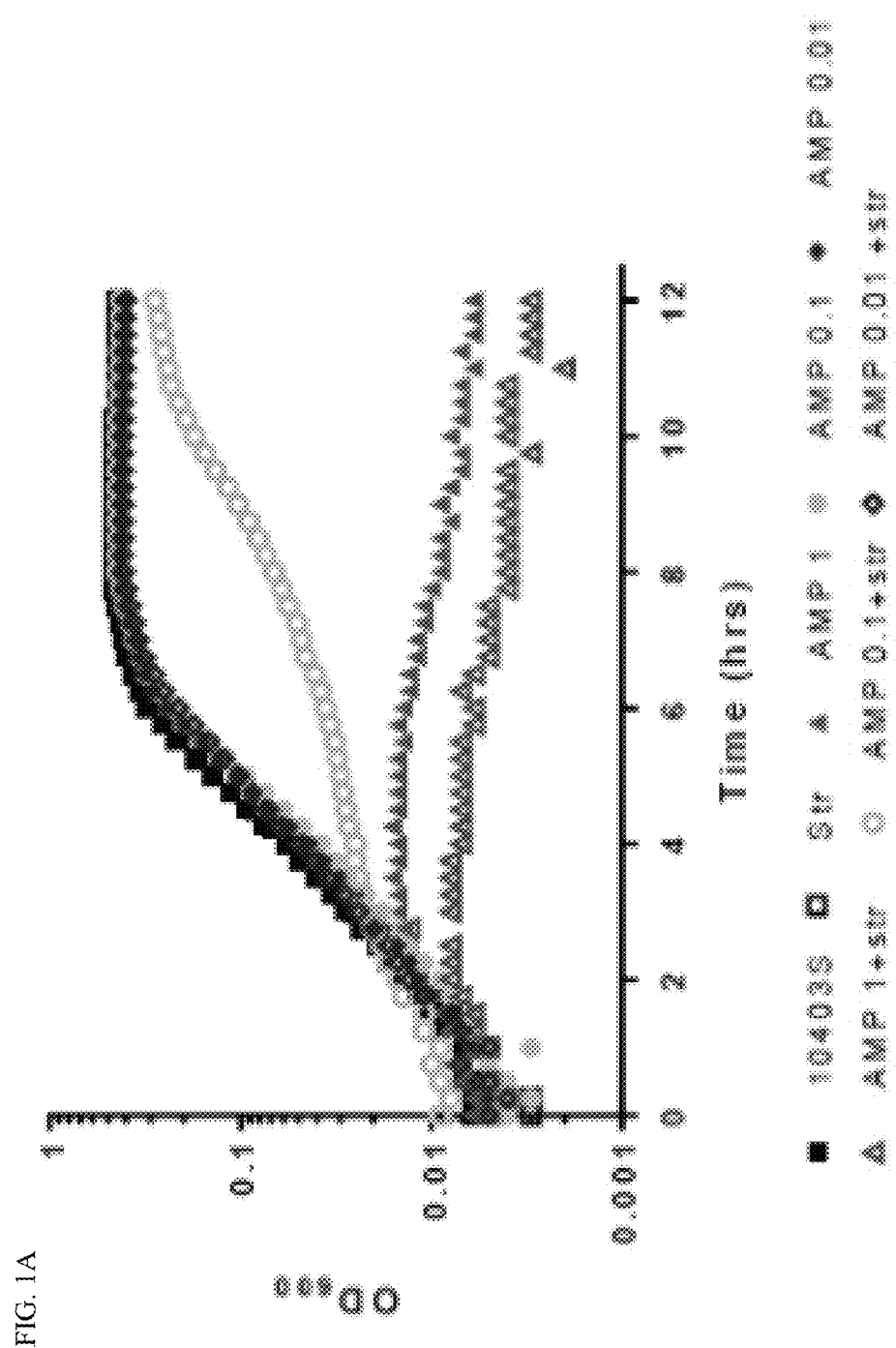
FIGS. 1A-1E. Staurosporine sensitizes *L. monocytogenes* to β-lactam antibiotics. Overnight cultures of wild type *L. monocytogenes* were back diluted and treated with 10-fold serial dilutions of ampicillin. Antibiotic concentrations are μg/ml. Growth was analyzed for 12 hours at 15 minute intervals. Data are representative of at least 3 independent repeats.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described.

The disclosed compound formulas and structures can in some cases vary between neutral, acid, and/or basic salt forms, depending on the surrounding environment, and such forms may be used interchangeably herein. As a non-limiting example, a primary amine moiety on a compound may be interchangeably designated as —$NH_2$ or as $NH_3^+$. Furthermore, a given compound may have equivalent resonance structures, which may be used interchangeably herein. Finally, a number of the disclosed compounds may exist as multiple enantiomers having different biological/biochemical effects. Herein, all structures that are drawn as a single enantiomer or without a designated stereochemistry encompass all possible enantiomers of the structure.

All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The embodiments described herein relate to compositions and methods for treating infections caused by Gram-positive bacteria by increasing the sensitivity of the bacteria to β-lactam antibiotics that are typically used to treat such infections. Specifically, the method involves administering to a subject an effective amount of one or more of the disclosed kinase inhibitors.

As used herein, the term "administering" refers to bringing a subject, tissue, organ or cells in contact with one or more of the kinase inhibitors described in this disclosure. In certain embodiments, the present invention encompasses administering the compounds useful in the present invention to a patient or subject. A "subject," "patient" and "individual," used equivalently herein, refers to a mammal, preferably a human, that either: (1) is infected with a Gram-positive bacteria, such infection being remediable, treatable, or diminished in severity by administration of the kinase inhibitors according to the invention; or (2) is susceptible to such an infection that is preventable by administering same.

As used herein, the terms "effective amount" and "therapeutically effective amount" refer to the quantity of active therapeutic agents sufficient to yield a desired therapeutic response without undue adverse side effects such as toxicity, irritation, or allergic response. The specific "effective amount" will, obviously, vary with such factors as the particular condition being treated, the physical condition of the patient, the duration of the treatment, the nature of concurrent therapy (if any), and the specific formulations employed. In this case, an amount would be deemed therapeutically effective if it resulted in one or more of the following: (a) the prevention of infection caused by a Gram-positive bacteria; and (b) the reduction or stabilization of infection caused by a Gram-positive bacteria. The optimum effective amounts can be readily determined by one of ordinary skill in the art using routine experimentation.

There are few antibiotics left to treat drug resistant bacteria, and there is no existing technology to re-sensitize MRSA to β-lactams. In some embodiments, compositions of this invention are used to treat infections by drug-resistant strains of bacteria. By "drug-resistant" it is meant that the bacteria are resistant to treatment with one or more conventional antibiotics. However, the disclosed method may result in improved therapies for treating any Gram-positive bacterial infection that is typically treated with β-lactams, including without limitation infections caused by *Listeria monocytogenes, Staphylococcus aureus* (including MSRA), *Streptococcus pneumoniae, Mycobacterium tuberculosis* and other mycobacteria, *Nocardia*, including the pan resistant *N. farcinia, Clostridium*, and enterococci. The target of the kinase inhibitors (Stk1) is phylogenetically distinct in Gram-negative and Gram-positive bacteria; so the disclosed compounds can selectively inhibit Gram-positive bacteria (and not act against the Gram-negative flora of the human gut), a potentially useful characteristic.

The disclosed compounds may be administered prior to, simultaneously with, or subsequent to a β-lactam antibiotic ("co-administration"). The kinase inhibitor and antibiotic may be administered separately by different routes, if desired. As used herein, the term "co-administered" is used to denote simultaneous or sequential administration. Preferably, such co-administration produces a synergistic effect. The terms "synergy" and "synergistic effect" indicate that the effect produced when two or more drugs are co-administered is greater than would be predicted based on the effect produced when the compounds are administered individually. In general, a synergistic effect is most clearly demonstrated at sub-optimal concentrations of the compounds (i.e., sub-therapeutic dosages). A lower dosage minimizes the potential of side effects, thereby providing an increased margin of safety. Synergy can result in lower cytotoxicity, increased antimicrobial effect, or some other beneficial effect of the combination compared with the individual components.

In one embodiment, the disclosed compounds are co-administered with a β-lactam antibiotic. In some embodiments, one or more of the disclosed compounds are co-administered with an antibiotic selected from the group consisting of benzathine penicillin, benzylpenicillin (penicillin G), phenoxymethylpenicillin (penicillin V), procaine penicillin, methicillin, oxacillin, nafcillin, cloxacillin, dicloxacillin, flucloxacillin, temocillin, amoxicillin, ampicillin, co-amoxiclav, azlocillin, carbenicillin, ticarcillin, mezlocillin, piperacillin, cephalosporins, cephalexin, cephalothin, cefazolin, cefaclor, cefuroxime, cefamandole, cephamycins, cefotetan, cefoxitin, ceftriaxone, cefotaxime, cefpodoxime, cefixime, ceftazidime, cefepime, cefpirome, imipenem, meropenem, ertapenem, faropenem, doripenem, monobactams, aztreonam, tigemonam, nocardicin A, and tabtoxinine-β-lactam.

In some embodiments, the disclosed compounds and the antibiotic will be administered by the same route and in a single composition, so as to ensure that they are given simultaneously to the subject. In some embodiments, the disclosed compounds and the antibiotic will be administered by different routes and in separate compositions, for example to improve stability and/or efficacy.

The disclosure also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Selective Pharmacologic Inhibition of a PASTA Kinase with Staurosporine or AZD5438 Increases Listeria monocytogenes Susceptibility to β-Lactam Antibiotics Abstract.

While β-lactam antibiotics are a critical part of the antimicrobial arsenal, they are frequently compromised by various resistance mechanisms including changes in penicillin binding proteins of the bacterial cell wall. Genetic deletion of the Penicillin binding protein and Serine-Threonine kinase associated protein (PASTA) kinase in Methicillin Resistant Staphylococcus aureus (MRSA) has been shown to restore β-lactam susceptibility. However, the mechanism remains unclear and whether pharmacologic inhibition would have the same effect is unknown.

In this Example, we demonstrate that pharmacologic inhibition of the PASTA kinase in Listeria monocytogenes by the nonselective kinase inhibitor staurosporine results in enhanced susceptibility to both aminopenicillin and cephalosporin antibiotics, and that pharmacologic inhibition of the PASTA kinase in Listeria monocytogenes by the selective kinase inhibitor AZD5438 enhanced susceptibility to cephalosporin antibiotics. Resistance to vancomycin, another class of cell wall synthesis inhibitor, or antibiotics that inhibit protein synthesis was unaffected by staurosporine treatment.

Phosphorylation assays with purified kinases revealed that staurosporine selectively inhibited the PASTA kinase of L. monocytogenes (PrkA). Importantly, staurosporine did not inhibit a L. monocytogenes kinase without a PASTA domain (Lmo0618) or the PASTA containing kinase from MRSA (Stk1). Overexpression of prkA via a theophylline controlled riboswitch partially protected L. monocytogenes from staurosporine induced cell wall stress sensitization. Overall these results suggest that pharmacologic targeting of PASTA kinases can increase the efficacy of β-lactam antibiotics.

Introduction.

In this Example, we test the hypothesis that pharmacologic inhibition of the PASTA kinase will lead to increased β-lactam susceptibility in the Gram positive pathogen L. monocytogenes. We demonstrate that L. monocytogenes is resistant to treatment with the non-specific kinase inhibitor staurosporine, but that combination therapy with β-lactam antibiotics and staurosporine leads to an ~100 fold increase in susceptibility to the β-lactam antibiotic. Importantly, the synergistic effect was only observed with β-lactams and not with other cell wall acting antibiotics such as vancomycin or non-cell wall active antibiotics such as kanamycin. We further show that staurosporine inhibits autophosphorylation of the L. monocytogenes PASTA kinase as well as substrate-level phosphorylation, while the S. aureus kinase is resistant to staurosporine treatment. Finally, we demonstrate that overexpression of the PASTA kinase in wild type L. monocytogenes reverses the synergistic effect of staurosporine and β-lactam antibiotics. Taken together, this work suggests that pharmacologic inhibition of PASTA kinases, in combination with β-lactam treatment, is a viable antibiotic development strategy.

Methods.

Antibiotics. Ampicillin (AMP), Ceftriaxone (CTX), Cefalexin (LEX), and Vancomycin (VAN) were purchased from Sigma Aldrich (St. Louis, Mo.) and resuspended according to the manufacturer's protocol. Kanamycin (KAN) was purchased from Fisher Scientific (Waltham, Mass.) and resuspended according to the manufacturer's protocol.

Bacterial strains and Growth. All L. monocytogenes strains used and generated in this study were derived from the 10403s background. Overexpression of prkA was achieved by placing the gene under control of a theophylline controlled riboswitch (19). Briefly, promoterless prkA was amplified and fused to a T5 promoter and theophylline riboswitch E (19) using splice overlap extension (SOE) PCR (20) (Table 1). The SOE product was then ligated into an erythromycin resistant derivative of the phage integration vector pPL2 (21) facilitating single copy, theophylline inducible expression from the chromosome in L. monocytogenes to create the strain prkA$^{theo}$. Staphylococcus aureus strain USA300 LAC was used both as a source of PASTA kinase DNA for cloning as well as in antibiotic treatment assays. Eschericia coli strains XL-1Blue and Rosetta BL21 were used for subcloning and protein expression, respectively. When needed, erythromycin (Sigma-Aldrich) was used at a final concentration of 2 μg/ml, chloramphenicol (Sigma-Aldrich) was used at 10 μg/ml and kanamycin (Sigma-Aldrich) was used at 20 μg/ml.

TABLE 1

Primers used in Example 1

| Primer Name | Sequence (5'-3') | Source |
|---|---|---|
| MLR50 (prkA$^{ribo}$ A) | GGCCGGGCCCGGAAATCATAAAAAATTTA TTTGC (SEQ ID NO: 1) | This study |
| MLR51 (prkA$^{ribo}$ B) | CTTAATCGCTTACCAATCATCATCTTGTT GTTACCTCCTTAGCA (SEQ ID NO: 2) | This study |
| MLR52 (prkA$^{ribo}$ C) | TGCTAAGGAGGTAACAACAAGATGATGAT TGGTAAGCGATTAAG (SEQ ID NO: 3) | This study |
| MLR53 (prkA$^{ribo}$ D) | GGCCCTCGAGTAATTTGGATAAGGGACTG TAC (SEQ ID NO: 4) | This study |
| JDS50 (lmo1820F) | ATATTATGGATCCATGATGATTGGTAAGC GATTAAGCGATCGAT (SEQ ID NO: 5) | This study |
| JDS54 (lmo1820R) | ATTATACAATTGTTTCTTTTTCTTGCTCA TTTTTTCTTTTTCTTATCTTTTTTCTC (SEQ ID NO: 6) | This study |
| JDS52 (lmo0618F) | ATATTATGGATCCATGGGAGAAATGACAC TTGCTTTTATAGAAGAACA (SEQ ID NO: 7) | This study |

TABLE 1-continued

Primers used in Example 1

| Primer Name | Sequence (5'-3') | Source |
|---|---|---|
| JDS55 (lmo0618R) | ATTATACAATTGGCCCTCTGTTGG TGGGCTGAAT (SEQ ID NO: 8) | This study |
| SA-STPK-F | TAGGATCCATGATAGGTAAAATAATAAAT GAAC (SEQ ID NO: 9) | This study |
| SA-STPK-R | TATAGAATTCTTATCGTGTTGATTTC TTTTTAGGTTTTG (SEQ ID NO: 10) | This study |

Broth growth curves. For in vitro growth experiments, *L. monocytogenes* strains were grown in brain heart infusion (BHI) medium at 30° C. overnight to stationary phase without shaking Overexpression strains were grown in BHI supplemented with 2 mM theophylline at 30° C. overnight without shaking to stationary phase. Methicillin-resistant *S. aureus* (strain USA300) was grown in tryptic soy broth (TSB) at 37° C. overnight with gyratory shaking (250 rpm) to stationary phase. Overnight stationary-phase cultures were back diluted 1:50 (*L. monocytogenes*) or 1:100 (*S. aureus*). Growth was measured at optical density 600 nm ($OD_{600}$) at fifteen minute intervals over the course of 12 hours in a 96-well plate format using an Eon Microplate Spectrophotometer or Synergy HT Microplate Spectrophotometer (BioTek Instruments, Inc., Winooski, Vt.). All growth experiments were repeated at least three times. For all in vitro growth assays, staurosporine (Calbiochem, Billerica, Mass.) was used at a final concentration of 10 μM, AZD 5438 (Selleck Chemicals, Houston) was used at 50 μM, and antibiotics were used at the concentrations specified in the figure legends.

Lmo0618, PrkA, S.a.Stk1 protein expression and purification. Using *L. monocytogenes* or *S. aureus* genomic DNA as template, lmo0618, prkA, and SaStk1 kinase domains were amplified (Table 1) and ligated into the expression vector GEX-2T to construct a glutathione S transferase (GST) fusion protein. The plasmids were transformed into Rosetta *E. coli* BL21, and protein expression was analyzed by SDS PAGE. The bacteria were pelleted by centrifugation, resuspended in 15 ml of lysis buffer (1× phosphate buffered saline [PBS], 1% Triton X-100, 2 μg/ml aprotinin, 1 μg/ml leupeptin, 25 μg/mlphenylmethylsulfonyl fluoride [PMSF]) and lysed with a cell disruptor (Branson, Danbury Conn.). Cell debris was pelleted by centrifugation for 15 minutes.

The supernatant was incubated with a slurry of glutathione-Sepharose 4B beads (GE Healthcare Life Sciences, Pittsburgh, Pa.) and 1X PBS (50:50 v/v) for one hour at 4° C. with gentle agitation. Following incubation, beads were pelleted by centrifugation, washed with five ml cold 1X PBS, and resuspended in five ml 1X PBS. The bound protein was eluted using disposable chromatography columns (Thermo Scientific, Rockford, Ill.) and an elution buffer containing 50 mM Tris (pH 8.0) and 20 mM reduced glutathione. The fractions were assessed for purity via SDS-PAGE, and fractions with estimated >95% purity were concentrated via centrifugation and glutathione was removed and exchanged with 1X PBS using a buffer exchange unit (Amicon, Billerica, Mass.).

In vitro protein phosphorylation. Phosphorylation assays were performed by mixing 1 μg of PrkA, Lmo0618, or S.a.Stk1 in a 10 μl reaction mixture containing 50 mM Tris-HCl (pH 7.4), 1 mM DTT, 5 mM $MnCl_2$, 250 μM ATP, 1 μCi of [$\gamma$-$^{32}$P]-ATP, followed by incubation at room temperature, overnight. To investigate substrate-level phosphorylation, ~10 μg of myelin basic protein (Novatein Biosciences, Woburn, Mass.) were added to the reaction mixture described above and incubated at room temperature, overnight. The reactions were terminated by adding 5X SDS loading buffer. Samples were fractionated by SDS-PAGE, fixed and dried, and analyzed by autoradiography.

Results

Figure 1B:
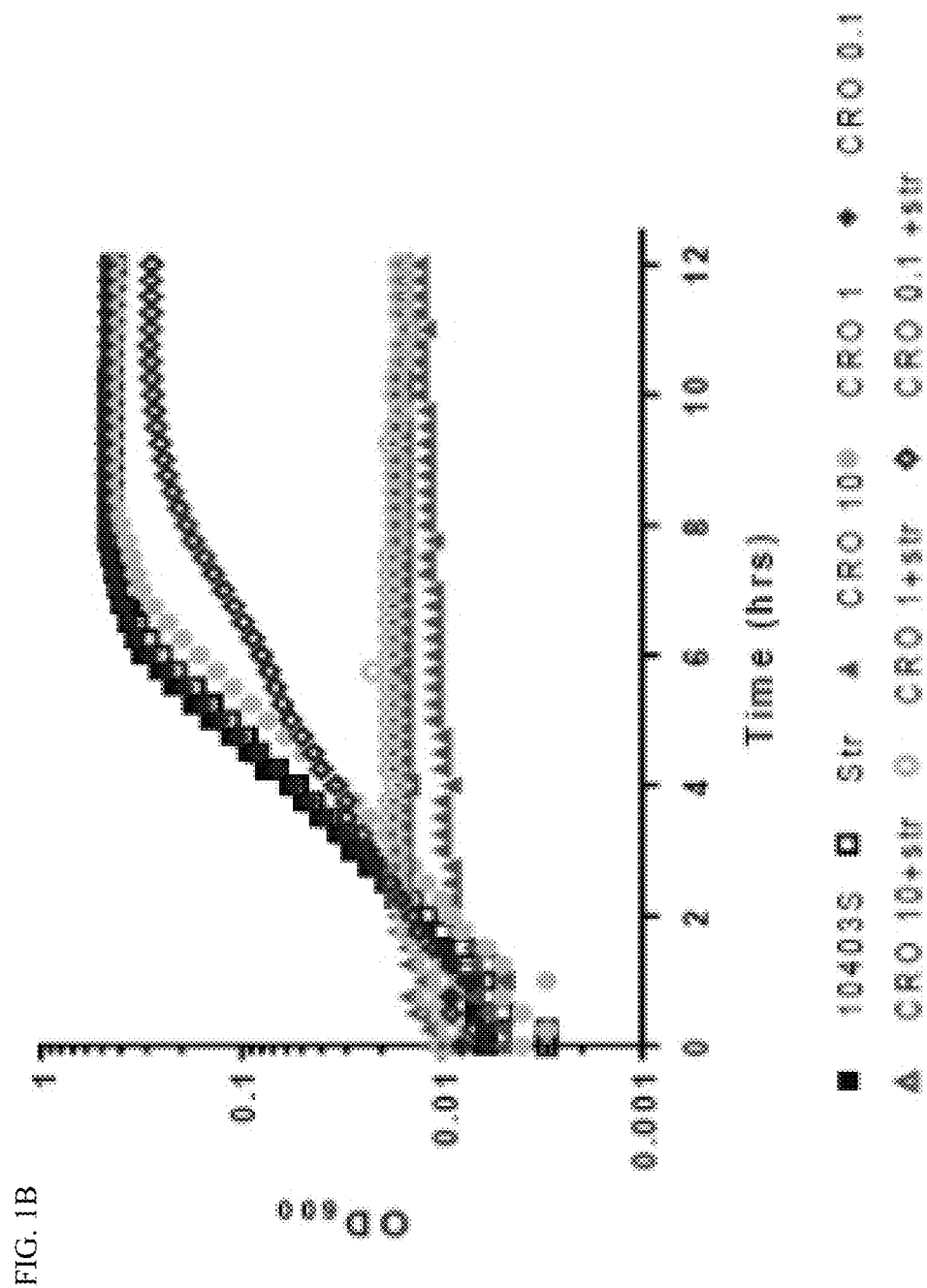
Figure 1C:
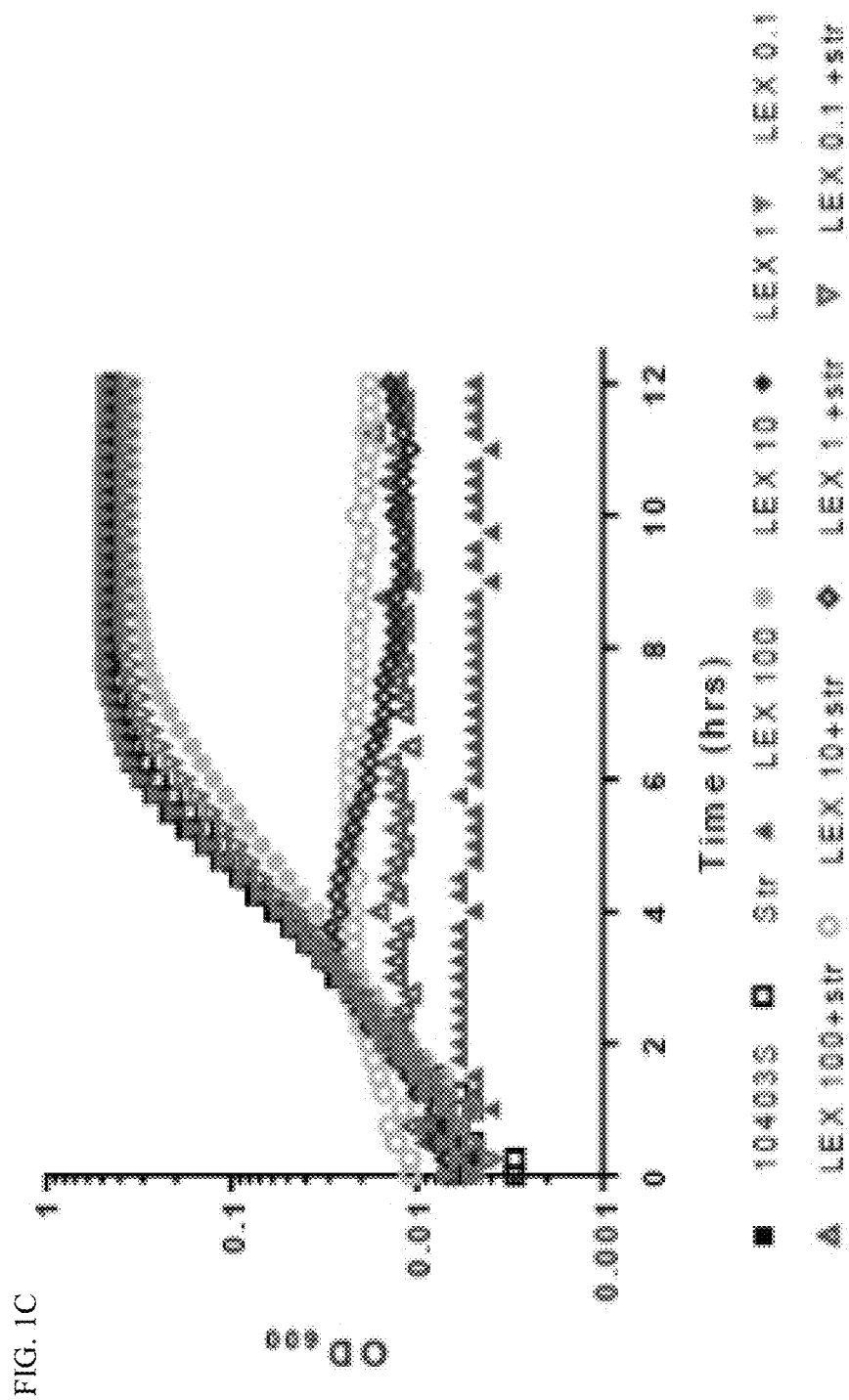
Figure 1D:
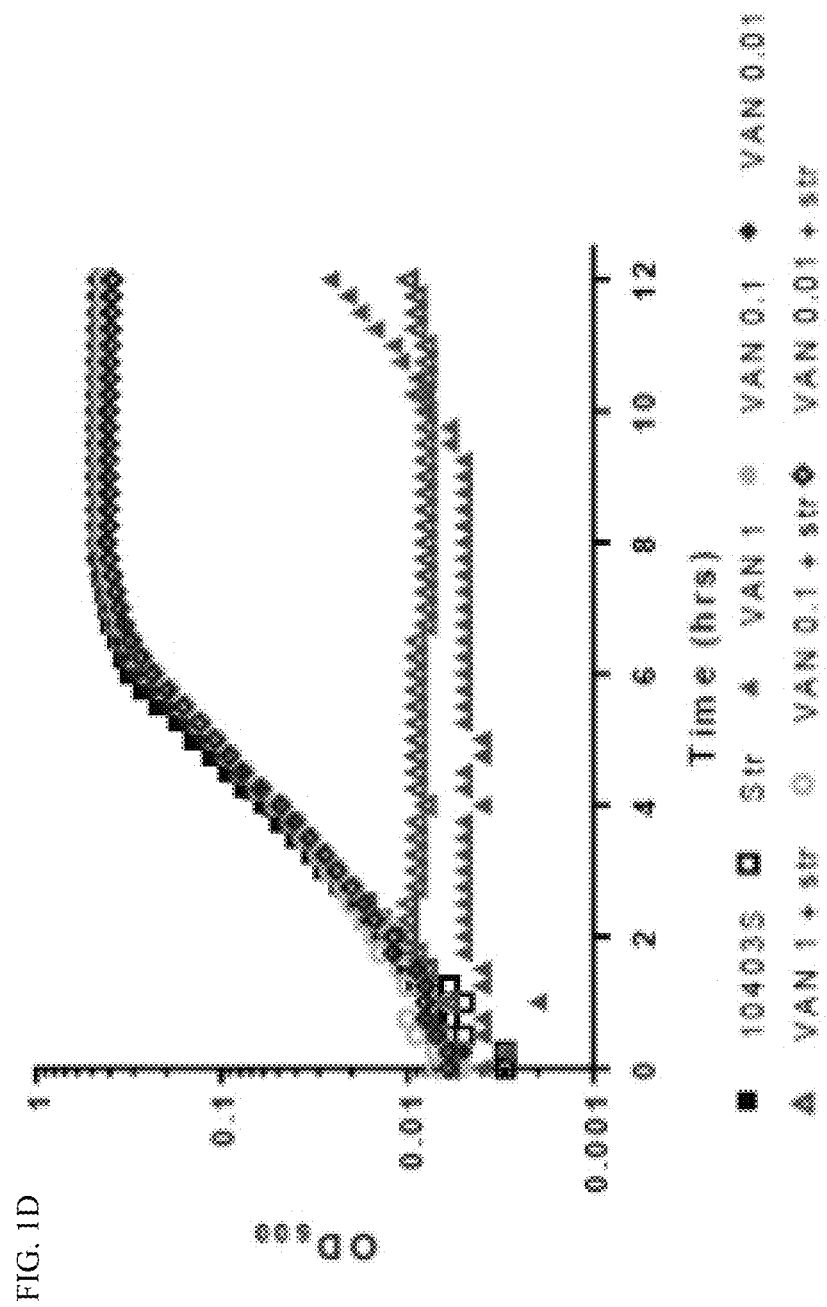
Figure 1E:
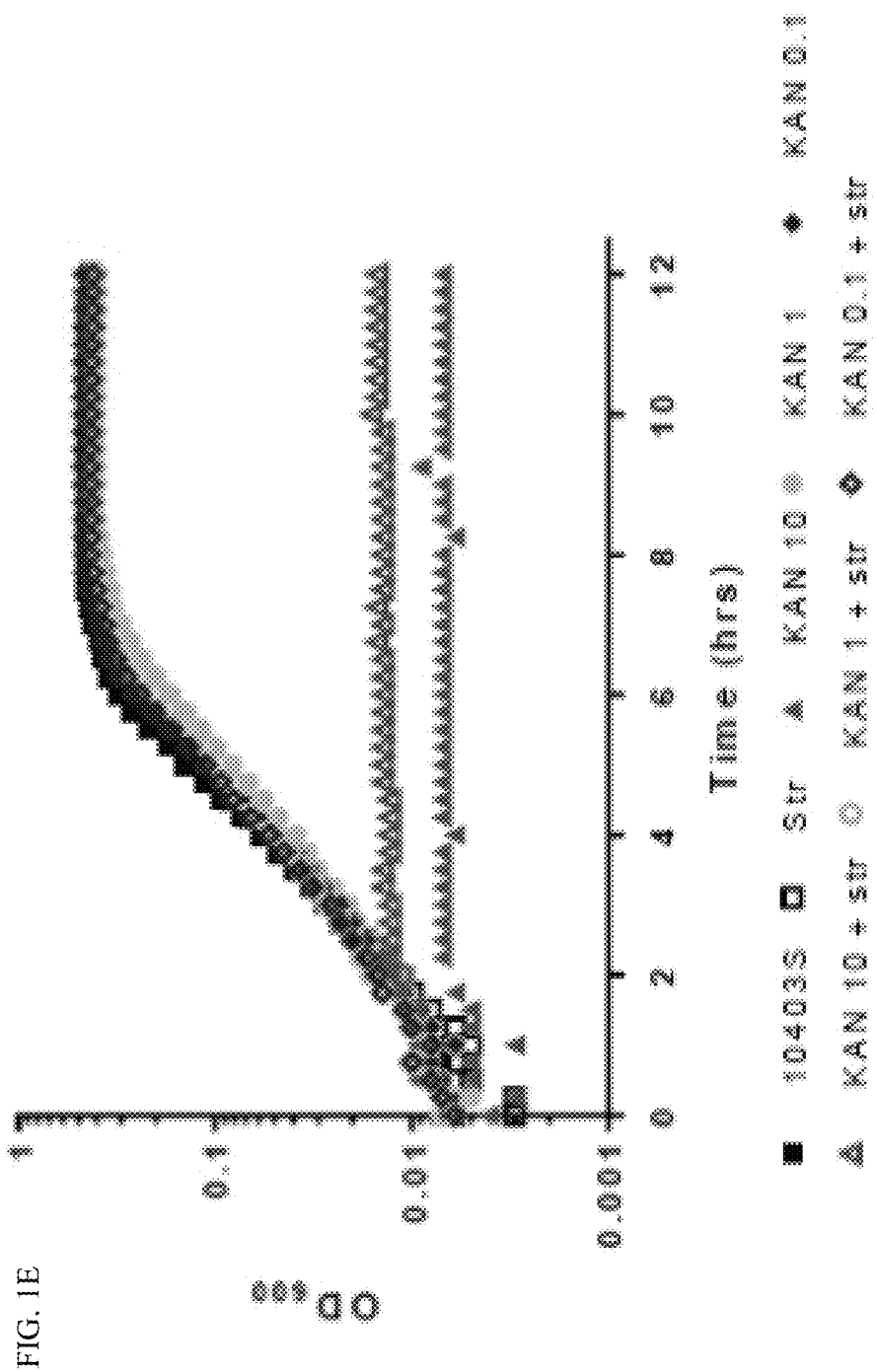
Figure 1F:
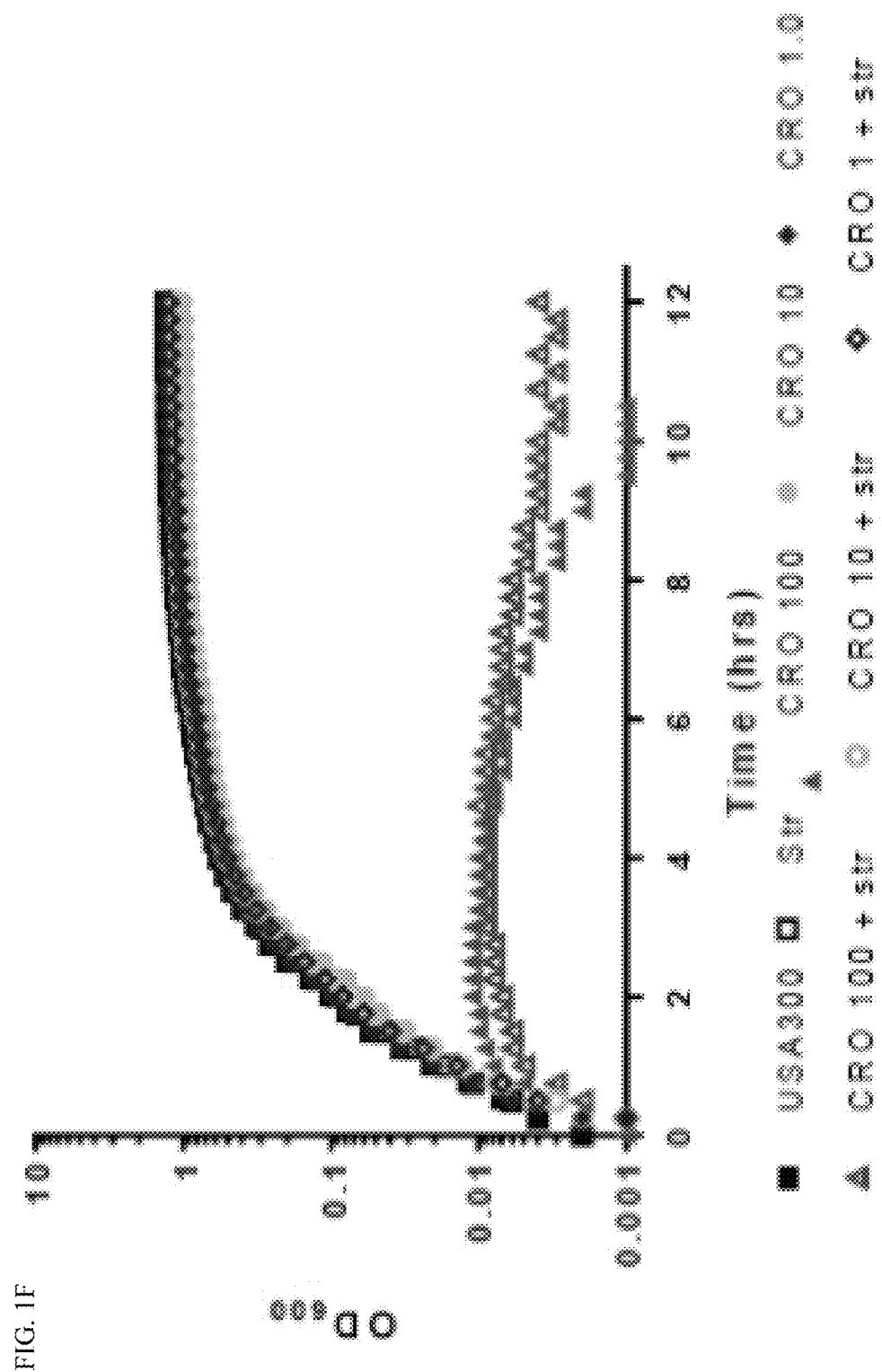
FIG. 1F shows results for overnight cultures of S. aureus that were back diluted and treated with ceftriaxone in the presence (open shape) or absence (closed shape) of 10 μM staurosporine.

Staurosporine sensitizes *L. monocytogenes* to β-lactam antibiotics. Deletion of the PASTA kinase in *S. aureus* or *E. faecalis* leads to an increase in susceptibility to β-lactam antibiotics (16-18). To test the hypothesis that pharmacologic inhibition of bacterial ser/threonine kinases could result in a synergistic sensitization to antibiotics we incubated the model Gram positive pathogen *L. monocytogenes* with or without the non-specific kinase inhibitor staurosporine in the presence of various antibiotics. Staurosporine treatment alone had a minimal effect on *L. monocytogenes* growth (FIG. 1 A-E). Similarly, sub-inhibitory concentrations of antibiotic had no effect on *L. monocytogenes* growth (FIG. 1A-E). However, treatment of *L. monocytogenes* with sub-inhibitory concentrations of β-lactam antibiotics (ampicillin, cefalexin and ceftriaxone), in the presence of 10 μM staurosporine led to a 10-100 fold increase in susceptibility (FIG. 1A-C). Staurosporine also increased the sensitization of *L. monocytogenes* to lysozyme, another source of cell wall stress (data not shown).

Importantly, as was previously shown with *S. aureus* and *E. faecalis* kinase deletion mutants, susceptibility to other cell wall acting antibiotics such as vancomycin or ribosome inhibitors such as kanamycin, was unaffected (FIG. 1 D, E). Also similar to deletion of PrkC in *E. faecalis*, treatment of wild type *L. monocytogenes* resulted in a growth defect specifically in chemically defined media, but not in rich media. Furthermore, while staurosporine had potent effects on the susceptibility of *L. monocytogenes* to β-lactam antibiotics, *S. aureus* susceptibility to ceftriaxone or other β-lactam or non-β-lactam antibiotics was unaffected (FIG. 1F and data not shown). Furthermore, we confirmed the synergistic activity of staurosporine and β-lactam antibiotics by immunofluorescence microscopy where we observed grossly disrupted bacterial morphology following combination drug treatments but not with either staurosporine or sub-inhibitory doses of β-lactam antibiotics alone. Taken together these data suggest that pharmacologic kinase inhibition by staurosporine in *L. monocytogenes* specifically sensitizes bacteria to β-lactam antibiotics.

Figure 2:
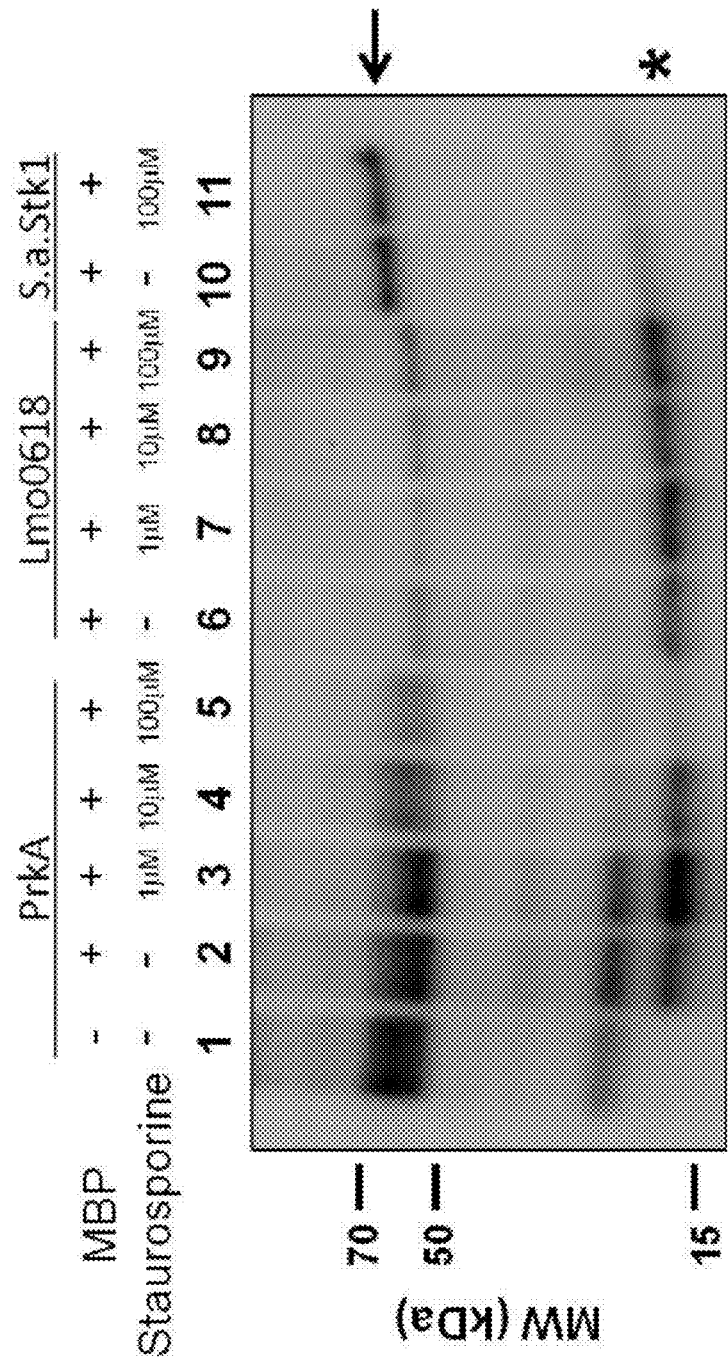
FIG. 2. Staurosporine inhibits PrkA in vitro phosphorylation in a dose-dependent manner. Autophosphorylation (arrow) and myelin basic protein (MBP) phosporylation (*) activity was assayed for PrkA (lanes 1-5), Lmo0618 (lanes 6-9), and S.a.Stk1 (lanes 10-11) in the presence or absence of 1 μM, 10 μM or 100 μM staurosporine.

Staurosporine selectively prevents *L. monocytogenes* PrkA phosphorylation. *L. monocytogenes*, like many Gram positive pathogens encodes two predicted serine/threonine kinases, one with an extracellular PASTA domain (PrkA) and one without (Lmo0618) (22). To determine if staurosporine, a broad spectrum kinase inhibitor (23), can selectively inhibit either or both of these kinases, the catalytic domains of both kinases were cloned into a GST bacterial expression vector, purified and assayed for activity in the presence or absence of increasing concentrations of staurosporine. Both PrkA as well as Lmo0618 have kinase activity as evidenced both by autophosphorylation as well as phosphorylation of the non-specific substrate Myelin Basic Protein (MBP) (FIG. 2). However, only PrkA, and not Lmo0618, was inhibited by staurosporine, both at the level of autophosphorylation as well as substrate level phosphorylation in a staurosporine concentration-dependent manner. Consistent with what we observed in antibiotic sensitization assays, the purified PASTA kinase from *S. aureus* was also resistant to staurosporine treatment. Taken together, these data suggest that staurosporine specifically inhibits the PASTA kinase in *L. monocytogenes*, potentially leading to sensitization to β-lactam antibiotics.

Figure 3A:
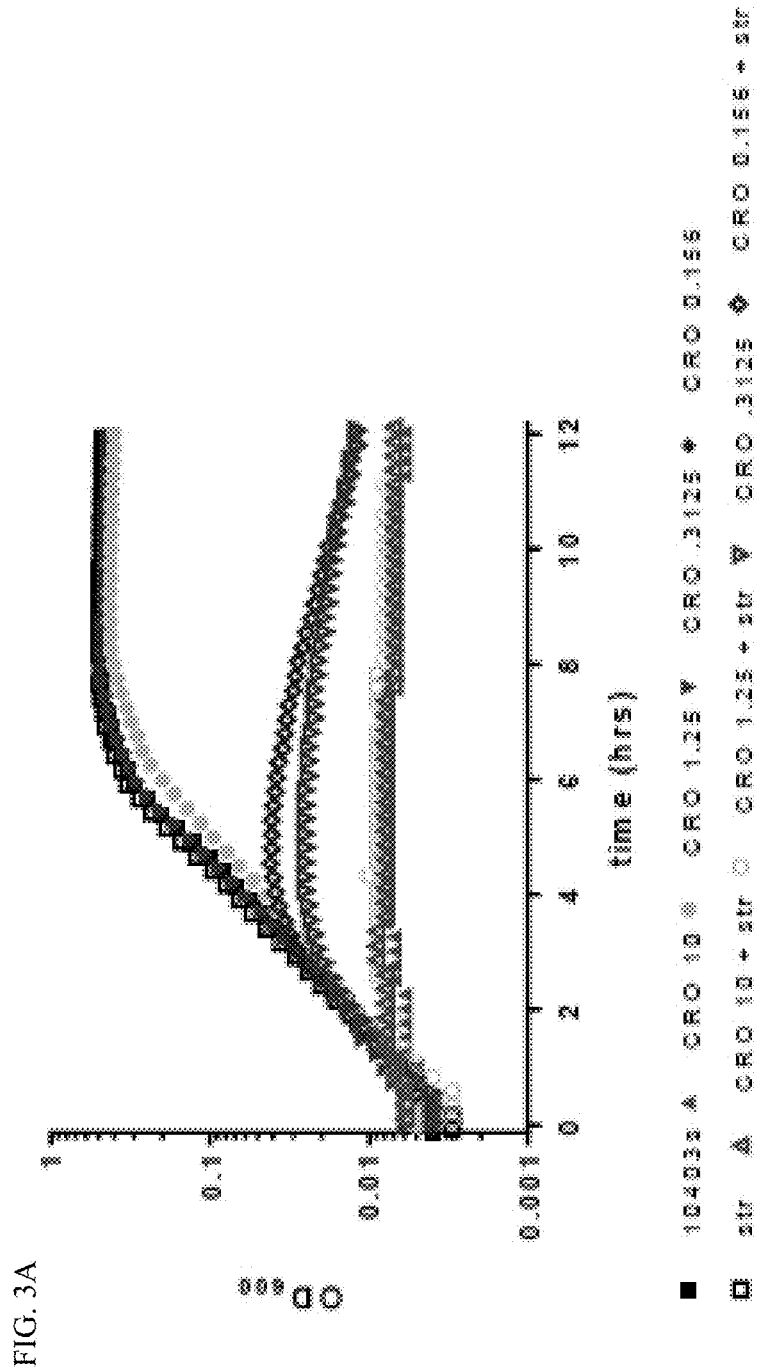
FIGS. 3A-3D. Overexpression of PrkA rescues the staurosporine induced susceptibility of L. monocytogenes to ceftriaxone. Overnight cultures of wild type (3A and 3B) or prkA$^{theo}$ (3C and 3D) L. monocytogenes were back diluted and treated with the indicated concentration of ceftriaxone in the presence (open shape, dashed line) or absence (closed shape, solid line) of 10 μM staurosporine and in the presence (3B and 3D) or absence of 2 mM theophylline (3A and 3C). Antibiotic concentrations are μg/ml. Growth was analyzed for 12 hours at 15 minute intervals. Data are representative of at least 3 independent repeats.
Figure 3B:
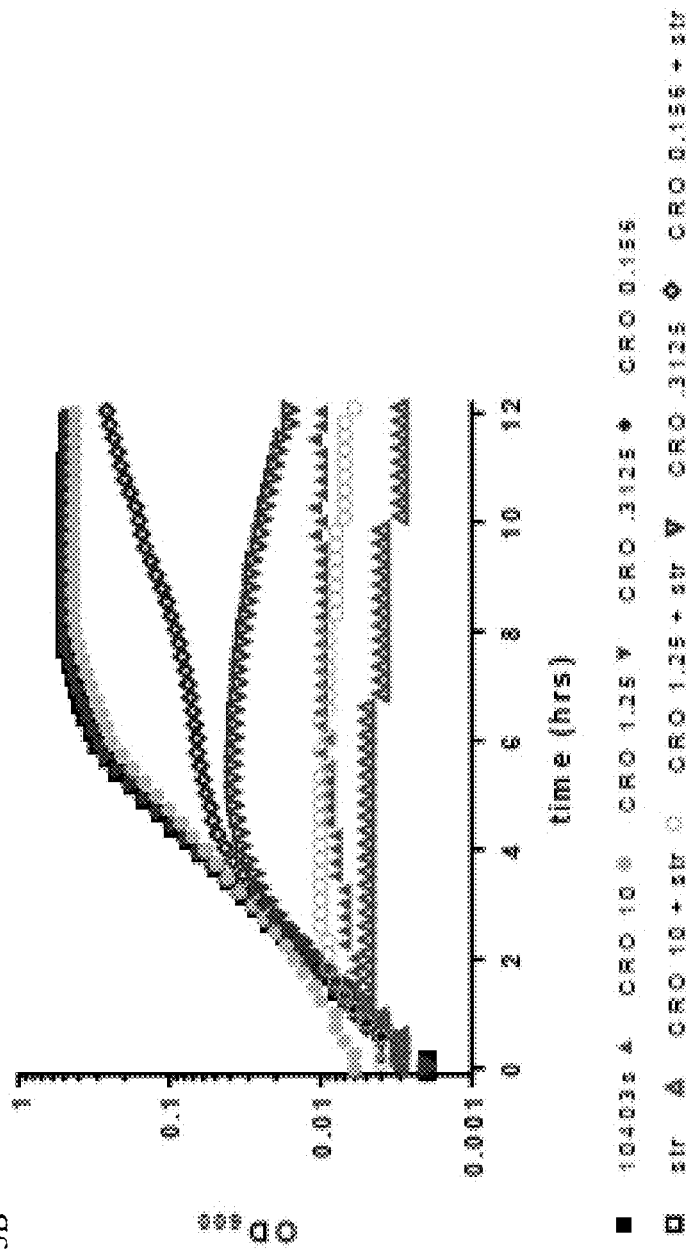
Figure 3C:
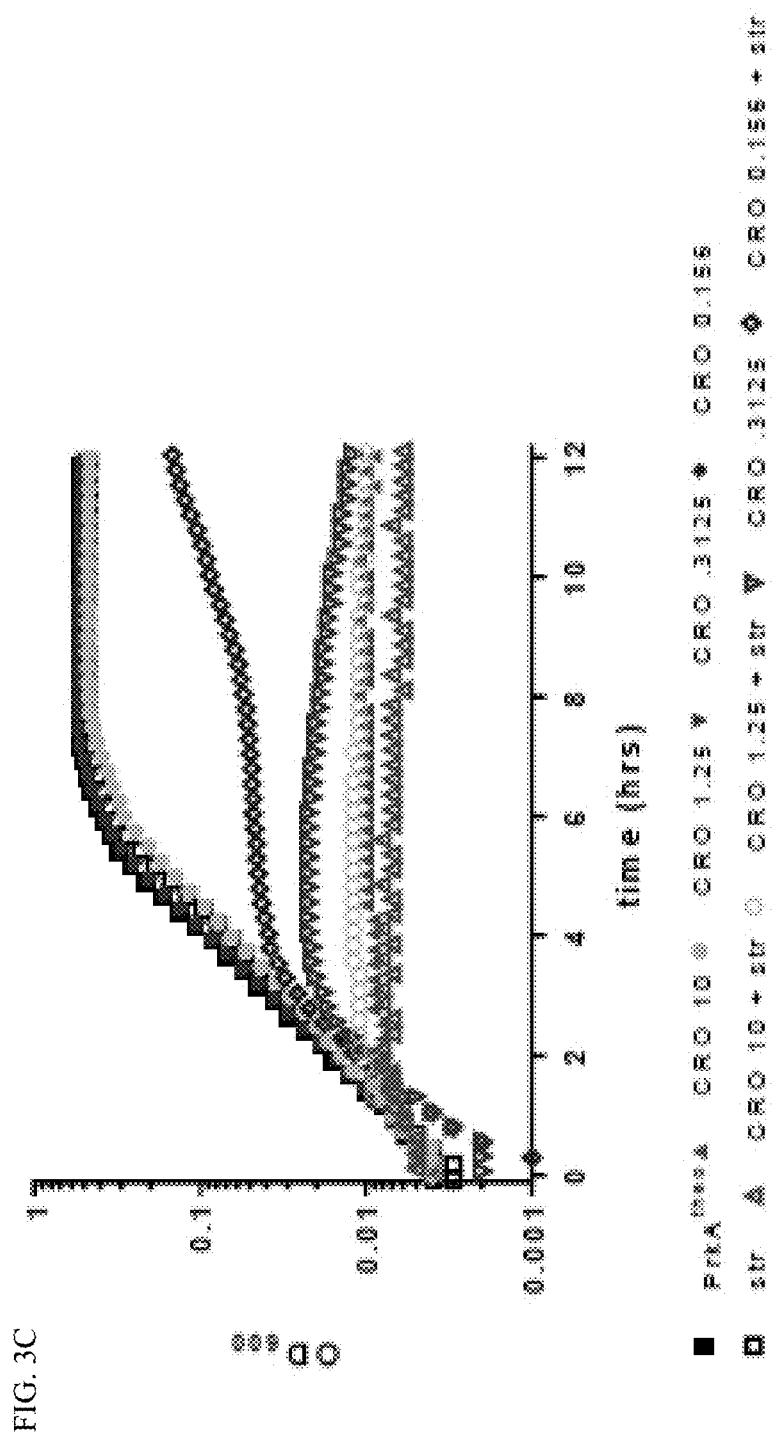
Figure 3D:
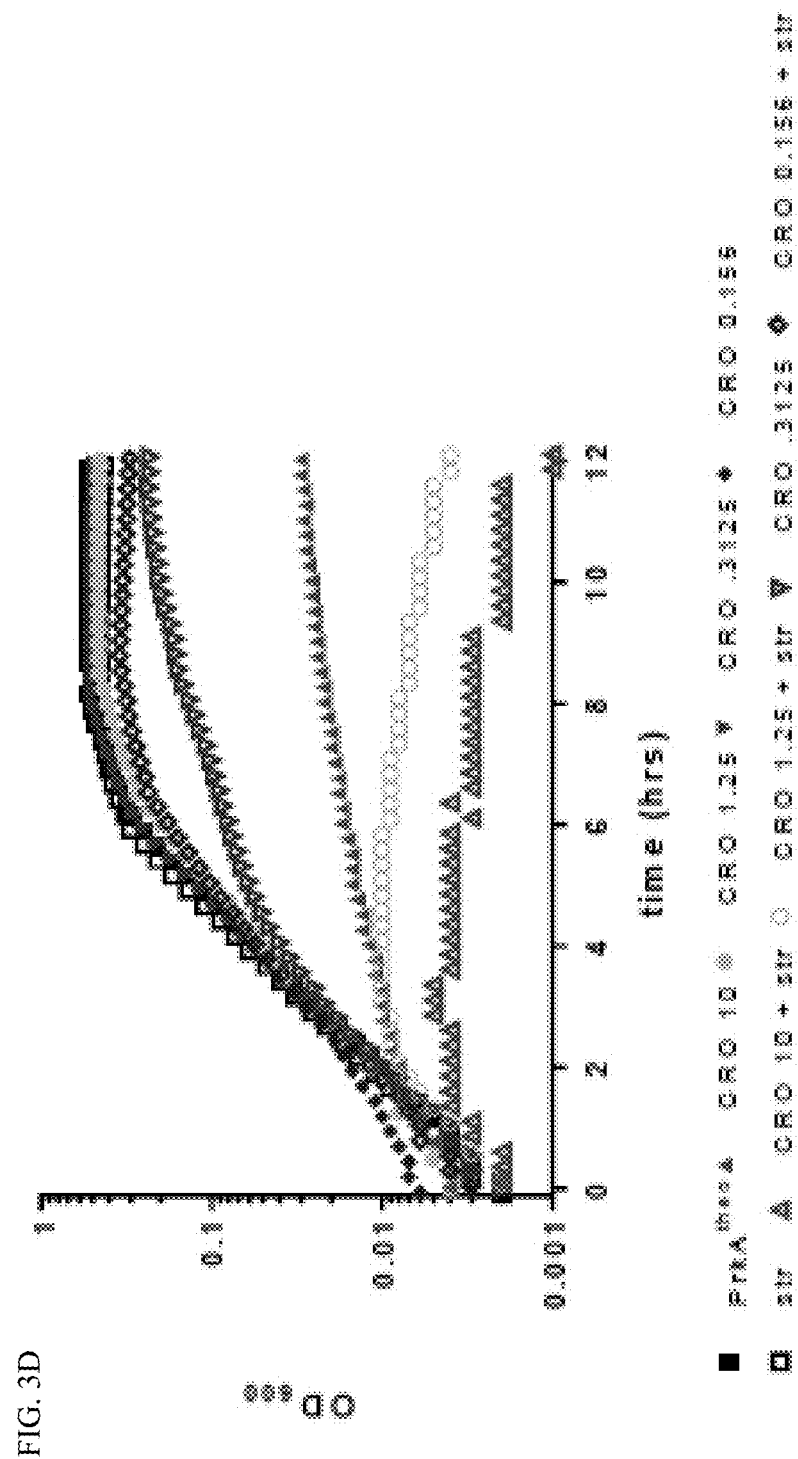

Overexpression of prkA rescues staurosporine sensitivity in *L. monocytogenes*. Repeated attempts to delete prkA in *L. monocytogenes* have failed, suggesting that the gene may be essential. Therefore, to genetically test the role of PrkA in staurosporine mediated β-lactam antibiotic sensitization, we engineered a strain of *L. monocytogenes* to overexpress prkA from a theophylline inducible riboswitch. Treatment of *L. monocytogenes* with staurosporine in combination with ceftriaxone led to a 100-fold increase in susceptibility to ceftriaxone as previously demonstrated (FIGS. 3A,C). However, upon overexpression of prkA, the sensitivity was partially rescued such that staurosporine only led to a 10-fold increase in susceptibility to ceftriaxone (FIG. 3D). Although the rescue was incomplete, this was likely due to the fact that we were overexpressing a target molecule that is itself still sensitive to staurosporine mediated inhibition.

Similarly, ampicillin and cefalexin sensitivities were decreased following overexpression of prkA, while kanamycin and vancomycin sensitivities were unaffected (data not shown). Together with the biochemical phosphorylation inhibition data, this suggests that staurosporine sensitizes *L. monocytogenes* to β-lactam antibiotics through the inhibition of the PASTA kinase, PrkA.

Figure 4:
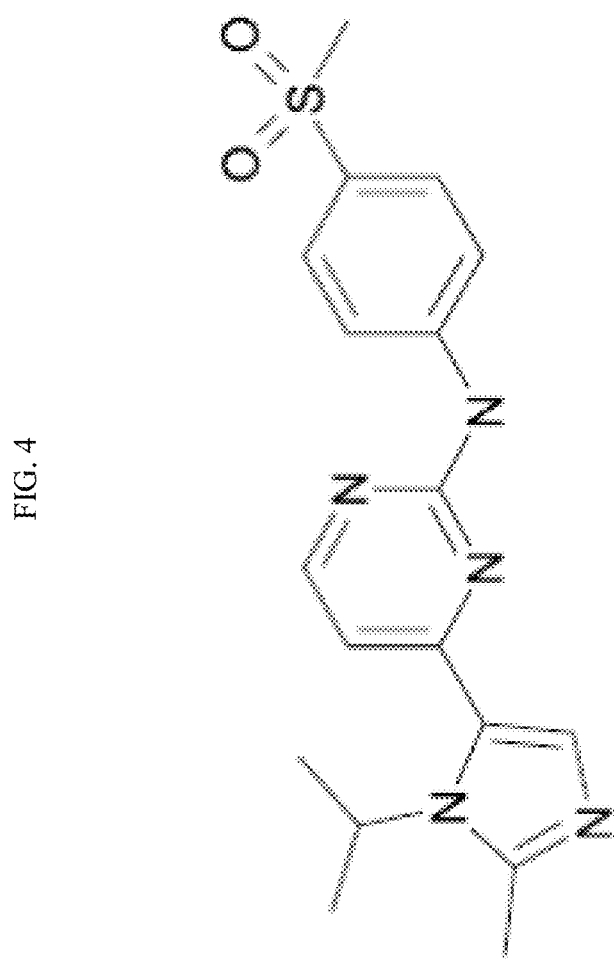
FIG. 4 shows the chemical structure of the CDK inhibitor AZD5438.
Figure 5A:
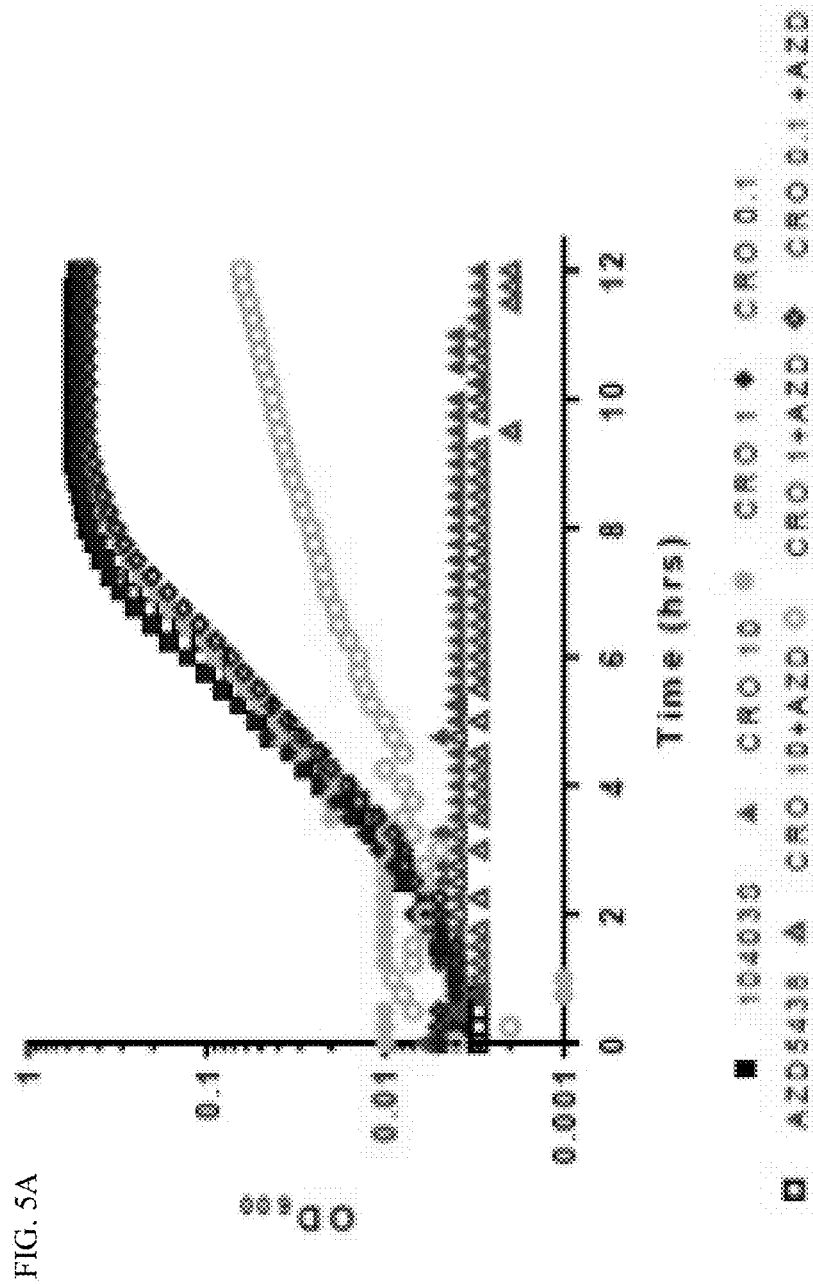
FIGS. 5A and 5B. AZD5438 also sensitizes L. monocytogenes to β-lactam treatment through inhibition of PrkA.
Figure 5B:
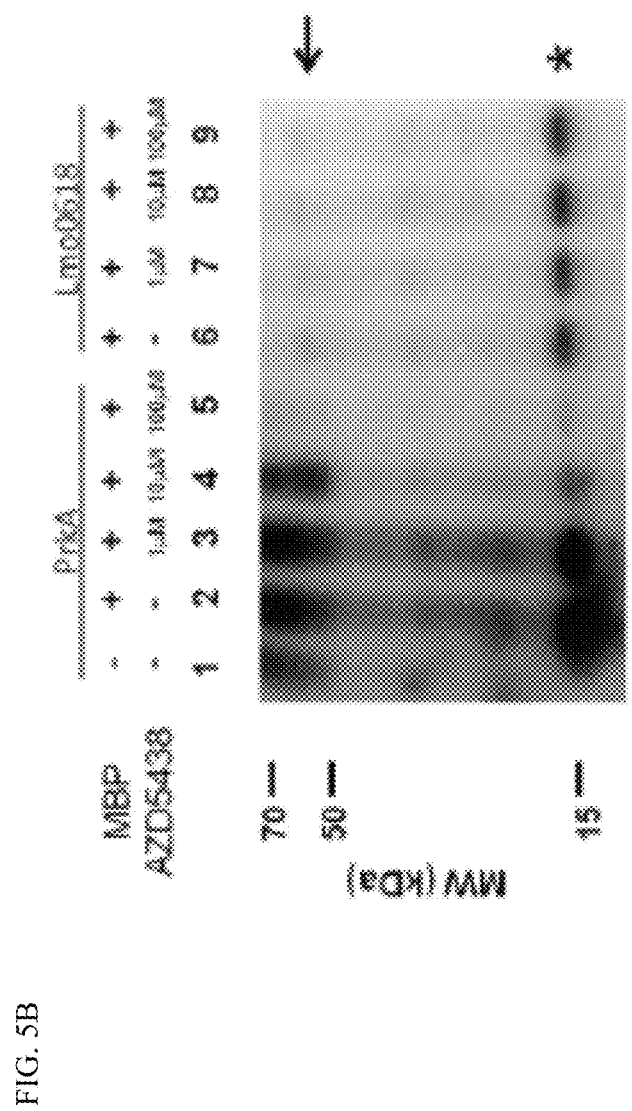

AZD5438 sensitizes *L. monocytogenes* to β-lactam treatment via inhibition of PrkA. Although staurosporine shows specificity for *L. monocytogenes* PrkA relative to Lmo0618 or S.a.Stk1, it has no therapeutic potential due to its nonselective nature and its promiscuity as an inhibitor of eukaryotic kinases. To determine if more selective kinase inhibitors could function to sensitize *L. monocytogenes* to β-lactam antibiotics we screened a small library of kinase inhibitors for β-lactam dependent inhibition of *L. monocytogenes* growth. We identified one compound, AZD5438 (a CDK inhibitor (24); see FIG. 4), capable of inhibiting *L. monocytogenes* growth in a (3-lactam synergistic dependent manner (FIG. 5A). Furthermore, AZD5438 acted synergistically with β-lactam antibiotics against *L. monocytogenes* but not *S. aureus* (data not shown). To determine if the mechanism of action is similar to that of staurosporine, we analyzed the ability of AZD5438 to inhibit PrkA and Lmo0618 activity in a biochemical phosphorylation assay. Similar to staurosporine, we observed that AZD5438 specifically inhibits PrkA while not inhibiting Lmo0618 (FIG. 5B). Taken together this data suggests that both non-selective (staurosporine) and specific (AZD5438) kinase inhibitors can synergistically act to sensitize Gram-positive bacteria, such as the model pathogen *L. monocytogenes*, to β-lactam antibiotic treatment.

Discussion.

The 518 human kinases share common structural features with ~30% similarity across the ~250 amino acid catalytic domain (25). Despite this structural similarity, pharmacologic selectivity has been achieved and resulted in widespread use of kinase inhibitors for cancer as well as other conditions (26). Until recently, prokaryotic phosphorylation was thought to largely be mediated by kinases specific to histidine and aspartyl residues (so called two-component regulators) (27-28). These histidine kinases have very little sequence homology to eukaryotic kinases (29). Histidine kinases typically phosphorylate a single target, the second component of the two-component signaling system that is usually a DNA binding response regulator (30). However, it is now clear that eukaryotic-like serine/threonine kinases (eSTKs) frequently occur in both Gram positive and negative prokaryotes (13).

The PASTA kinases however appear to be specific to Gram-positive bacteria (Firmicutes and Actinobacteria) (13). Similar to eukaryotic serine/threonine kinases, bacterial eSTKs have many targets, and in *L. monocytogenes* PrkA has already been shown to phosphorylate or interact with 62 unique substrates (31). These substrates imply a role for PrkA in carbohydrate metabolism, protein synthesis, cell wall synthesis and division. Indeed, pharmacologic inhibition of PrkA in *L. monocytogenes* leads to chaining and septation defects (data not shown). While most bacteria have only a few eSTKs (four or less) Streptomycetes and Mycobacterial genomes can have 10 or more (13). In MRSA, Stk1 is not an essential gene (16, 32), but attempts to knock out PrkA in *L. monocytogenes* to date have been unsuccessful, highlighting that while there are clearly shared functions, there are likely to be species-specific differences as well.

Staurosporine is a relatively nonselective kinase inhibitor (23). Despite the broad activity of staurosporine against human kinases, and the similarity of bacterial eSTKs to human kinases, we demonstrated selective inhibition of some, but not other bacterial kinases. Others have reported that staurosporine does inhibit the PASTA kinase of *Staphylococcus epidermidis* (33). Furthermore, we onberved additional evidence of of kinase specific selectivity with a different inhibitor, AZD5438. The specific residues that confer inhibitor specificity towards bacterial eSTKs remain to be defined. The specific residues that confer inhibitor specificity in the bacterial eSTKs remain to be defined. These differences are likely in the ATP binding pocket of the kinase domain and unrelated to the presence, absence, or number of repeats of the extracellular penicillin binding domain of the PASTA kinases. Understanding how inhibitor specificity is conferred is an important step in the rational design of inhibitors that will have specificity for bacterial PASTA kinases while avoiding non-specific inhibition of host kinases.

The penicillin binding domain of the PASTA kinases likely acts as a receptor for peptidoglycan fragments generated through cell wall damage or remodeling. In *M. tuberculosis* it was demonstrated that there was specificity for the second and third residues of the stem peptide, as well as the presence of MurNac sugar moiety of peptidoglycan fragments to facilitate binding and signaling through the PASTA domain of PknB (34). Presumably binding cell wall fragments transmits a signal to the kinase through a conformational change that allows regulation of substrates involved in cell wall remodeling and homeostasis. In the case of *L. monocytogenes*, these include cell shape determining proteins (MreB) and peptidoglycan synthesis proteins, GlmU and MurG (31).

In other organisms the PASTA kinases have been suggested to regulate cell wall homeostasis through the phosphorylation of PBPs and autolysins (35-36). Understanding how cell wall damage is recognized by the PASTA domain and what specific responses this triggers to will lead us to a mechanistic understanding of how the PASTA kinases work to maintain cell wall homeostasis and how this affects β-lactam susceptibility.

In summary, PrkA but not Lmo0618 is sensitive to staurosporine inhibition both in a cell free biochemical reaction, as well as in the bacterium. The result of this selective inhibition is to sensitize *L. monocytogenes* to cell wall stress similar to the phenotype seen in PASTA kinase deletions of *S. aureus* and *E. faecalis*. While antibiotic resistance in the model pathogen *L. monocytogenes* is not a burgeoning issue, we believe these data act as a proof of principle that specificity in targeting bacterial PASTA eSTKs is possible.

Pharmacologic inhibitors that target other bacterial PASTA kinases remain to be identified. However, our results suggest that generation of kinase inhibitors with specificity for bacterial PASTA kinases is a potentially viable approach to the development of novel antimicrobials that will work in combination therapy with β-lactam antibiotics. Importantly, we would propose that these inhibitors should work synergistically with β-lactam antibiotics independent of the resistance phenotype of the organisms they target as demonstrated by the resensitization of MRSA to β-lactams upon deletion of its homologous PASTA eSTK. A full analysis of the PASTA kinase phosphorylation substrates will lead to a mechanistic understanding of how kinase inhibition leads to increased β-lactam susceptibility. In addition a systematic understanding of the biochemical and biophysical interactions between kinase inhibitors and the PASTA kinases will facilitate the rational design of inhibitors with specificity for bacterial kinases and with limited cross reactivity with host serine threonine kinases.

References Cited (Background and Example 1):
1. Freitag N E, Port G C, Miner M D. 2009. *Listeria monocytogenes*—from saprophyte to intracellular pathogen. Nat Rev Microbiol 7:623-628.
2. Lecuit M. 2007. Human listeriosis and animal models. Microbes Infect 9:1216-1225.
3. Schlech W F, 3rd, Lavigne P M, Bortolussi R A, Allen A C, Haldane E V, Wort A J, Hightower A W, Johnson S E, King S H, Nicholls E S, Broome C V. 1983. Epidemic listeriosis—evidence for transmission by food. N Engl J Med 308:203-206.
4. Drevets D A, Bronze M S. 2008. *Listeria monocytogenes*: epidemiology, human disease, and mechanisms of brain invasion. FEMS Immunol Med Microbiol 53:151-165.
5. Temple M E, Nahata M C. 2000. Treatment of listeriosis Ann Pharmacother 34:656-661.
6. McCollum J T, Cronquist A B, Silk B J, Jackson K A, O'Connor K A, Cosgrove S, Gossack J P, Parachini S S, Jain N S, Ettestad P, Ibraheem M, Cantu V, Joshi M, DuVernoy T, Fogg N W, Jr., Gorny J R, Mogen K M, Spires C, Teitell P, Joseph L A, Tarr C L, Imanishi M, Neil K P, Tauxe R V, Mahon B E. 2013. Multistate outbreak of listeriosis associated with cantaloupe. N Engl J Med 369:944-953.
7. Jones E M, MacGowan A P. 1995. Antimicrobial chemotherapy of human infection due to *Listeria monocytogenes*. Eur J Clin Microbiol Infect Dis 14:165-175.
8. Lewis K. 2013. Platforms for antibiotic discovery. Nat Rev Drug Discov 12:371-387.
9. Sader H S, Jones R N. 2009. Antimicrobial susceptibility of Gram-positive bacteria isolated from U S medical centers: results of the Daptomycin Surveillance Program (2007-2008). Diagn Microbiol Infect Dis 65:158-162.
10. Villegas-Estrada A, Lee M, Hesek D, Vakulenko S B, Mobashery S. 2008. Co-opting the cell wall in fighting methicillin-resistant *Staphylococcus aureus*: potent inhibition of PBP 2a by two anti-MRSA beta-lactam antibiotics. J Am Chem Soc 130:9212-9213.
11. Richter S S, Heilmann K P, Dohrn C L, Riahi F, Costello A J, Kroeger J S, Biek D, Critchley I A, Diekema D J, Doern G V. 2011. Activity of ceftaroline and epidemiologic trends in *Staphylococcus aureus* isolates collected from 43 medical centers in the United States in 2009. Antimicrob Agents Chemother 55:4154-4160.
12. Yeats C, Finn R D, Bateman A. 2002. The PASTA domain: a beta-lactam-binding domain. Trends Biochem Sci 27:438.
13. Pereira S F, Goss L, Dworkin J. 2011. Eukaryote-like serine/threonine kinases and phosphatases in bacteria. Microbiol Mol Biol Rev 75:192-212.
14. Fernandez P, Saint-Joanis B, Barilone N, Jackson M, Gicquel B, Cole S T, Alzari P M. 2006. The Ser/Thr protein kinase PknB is essential for sustaining mycobacterial growth. J Bacteriol 188:7778-7784.
15. Hussain H, Branny P, Allan E. 2006. A eukaryotic-type serine/threonine protein kinase is required for biofilm formation, genetic competence, and acid resistance in *Streptococcus mutans*. J Bacteriol 188:1628-1632.
16. Tamber S, Schwartzman J, Cheung A L. 2010. Role of PknB kinase in antibiotic resistance and virulence in community-acquired methicillin-resistant *Staphylococcus aureus* strain USA300. Infect Immun 78:3637-3646.
17. Beltramini A M, Mukhopadhyay C D, Pancholi V. 2009. Modulation of cell wall structure and antimicrobial susceptibility by a *Staphylococcus aureus* eukaryote-like serine/threonine kinase and phosphatase. Infect Immun 77:1406-1416.
18. Kristich C J, Wells C L, Dunny G M. 2007. A eukaryotic-type Ser/Thr kinase in *Enterococcus faecalis* mediates antimicrobial resistance and intestinal persistence. Proc Natl Acad Sci USA 104:3508-3513.
19. Topp S, Reynoso C M, Seeliger J C, Goldlust I S, Desai S K, Murat D, Shen A, Puri A W, Komeili A, Bertozzi C R, Scott J R, Gallivan J P. 2010. Synthetic riboswitches that induce gene expression in diverse bacterial species. Appl Environ Microbiol 76:7881-7884.
20. Horton R M, Cai Z L, Ho S N, Pease L R. 1990. Gene splicing by overlap extension: tailor-made genes using the polymerase chain reaction. Biotechniques 8:528-535.
21. Lauer P, Chow M Y, Loessner M J, Portnoy D A, Calendar R. 2002. Construction, characterization, and use of two *Listeria monocytogenes* site-specific phage integration vectors. J Bacteriol 184:4177-4186.
22. Glaser P, Frangeul L, Buchrieser C, Rusniok C, Amend A, Baquero F, Berche P, Bloecker H, Brandt P, Chakraborty T, Charbit A, Chetouani F, Couve E, de Daruvar A, Dehoux P, Domann E, Dominguez-Bernal G, Duchaud E, Durant L, Dussurget O, Entian K D, Fsihi H, Garcia-del Portillo F, Garrido P, Gautier L, Goebel W, Gomez-Lopez N, Hain T, HaufJ, Jackson D, Jones L M, Kaerst U, Kreft J, Kuhn M, Kunst F, Kurapkat G, Madueno E, Maitournam A, Vicente J M, Ng E, Nedjari H, Nordsiek G, Novella S, de Pablos B, Perez-Diaz J C, Purcell R, Remmel B, Rose M, Schlueter T, Simoes N, Tierrez A, Vazquez-Boland J A, Voss H, Wehland J, Cossart P. 2001. Comparative genomics of *Listeria* species. Science 294:849-852.
23. Karaman M W, Herrgard S, Treiber D K, Gallant P, Atteridge C E, Campbell B T, Chan K W, Ciceri P, Davis M I, Edeen P T, Faraoni R, Floyd M, Hunt J P, Lockhart D J, Milanov Z V, Morrison M J, Pallares G, Patel H K, Pritchard S, Wodicka L M, Zarrinkar P P. 2008. A quantitative analysis of kinase inhibitor selectivity. Nat Biotechnol 26:127-132.
24. Heerding D A, Rhodes N, Leber J D, Clark T J, Keenan R M, Lafrance L V, Li M, Safonov I G, Takata D T, Venslaysky J W, Yamashita D S, Choudhry A E, Copeland R A, Lai Z, Schaber M D, Tummino P J, Strum S L, Wood E R, Duckett D R, Eberwein D, Knick V B, Lansing T J, McConnell R T, Zhang S, Minthorn E A, Concha N O, Warren G L, Kumar R. 2008. Identification of 4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol (GSK690693), a novel inhibitor of AKT kinase. J Med Chem 51:5663-5679.

25. Brooijmans N, Chang Y W, Mobilio D, Denny R A, Humblet C. 2010. An enriched structural kinase database to enable kinome-wide structure-based analyses and drug discovery. Protein Sci 19:763-774.
26. Chahrour O, Cairns D, Omran Z. 2012. Small molecule kinase inhibitors as anti-cancer therapeutics. Mini Rev Med Chem 12:399-411.
27. Bakal C J, Davies J E. 2000. No longer an exclusive club: eukaryotic signalling domains in bacteria. Trends Cell Biol 10:32-38.
28. Munoz-Dorado J, Inouye S, Inouye M. 1991. A gene encoding a protein serine/threonine kinase is required for normal development of M. xanthus, a gram-negative bacterium. Cell 67:995-1006.
29. Hanks S K, Hunter T. 1995. Protein kinases 6. The eukaryotic protein kinase superfamily: kinase (catalytic) domain structure and classification. FASEB J 9:576-596.
30. Laub M T, Goulian M. 2007. Specificity in two-component signal transduction pathways. Annu Rev Genet 41:121-145.
31. Lima A, Duran R, Schujman G E, Marchissio M J, Portela M M, Obal G, Pritsch O, de Mendoza D, Cervenansky C. 2011. Serine/threonine protein kinase PrkA of the human pathogen Listeria monocytogenes: biochemical characterization and identification of interacting partners through proteomic approaches. J Proteomics 74:1720-1734.
32. Debarbouille M, Dramsi S, Dussurget O, Nahori M A, Vaganay E, Jouvion G, Cozzone A, Msadek T, Duclos B. 2009. Characterization of a serine/threonine kinase involved in virulence of Staphylococcus aureus. J Bacteriol 191:4070-4081.
33. Liu Q, Fan J, Niu C, Wang D, Wang J, Wang X, Villaruz A E, Li M, Otto M, Gao Q. 2011. The eukaryotic-type serine/threonine protein kinase Stk is required for biofilm formation and virulence in Staphylococcus epidermidis. PLoS One 6:e25380.
34. Mir M, Asong J, Li X, Cardot J, Boons G J, Husson R N. 2011. The extracytoplasmic domain of the Mycobacterium tuberculosis Ser/Thr kinase PknB binds specific muropeptides and is required for PknB localization. PLoS Pathog 7:e1002182.
35. Shah I M, Dworkin J. 2010. Induction and regulation of a secreted peptidoglycan hydrolase by a membrane Ser/Thr kinase that detects muropeptides. Mol Microbiol 75:1232-1243.
36. Dasgupta A, Datta P, Kundu M, Basu J. 2006. The serine/threonine kinase PknB of Mycobacterium tuberculosis phosphorylates PBPA, a penicillin-binding protein required for cell division. Microbiology 152:493-504.

Example 2

Selective Inhibition with GSK690693 Increases Listeria monocytogenes Susceptibility to β-Lactam Antibiotics In this Example, we report the result of a study following the procedure of Example 1, but instead using the selective Akt inhibitor GSK690693 to sensitize L. monocytogenes to β-lactam antibiotics.

We screened a library of 367 kinase inhibitors for β-lactam dependent inhibition of L. monocytogenes growth. Among other candidates reported in Example 3, we identified GSK690693, an Akt inhibitor (see FIG. 6) capable of inhibiting L. monocytogenes growth in a β-lactam synergistic dependent manner (FIG. 7).

Similar to Example 1, wild type L. monocytogenes were back diluted and treated with 10-fold serial dilutions of ceftriaxone in the presence or absence of 100 µM GSK690693. Antibiotic concentrations are µg/ml. Growth was analyzed for 12 hours at 15 minute intervals. Data are representative of at least 3 independent repeats. GSK690693 inhibited L. monocytogenes growth in a β-lactam synergistic dependent manner (FIG. 7).

Example 3

Seven Compounds that Increased Listeria monocytogenes Susceptibility to β-Lactam Antibiotics, and One of these Seven Compounds Also Increased MSRA Susceptibility to β-Lactam Antibiotics In this Example, we summarize the results of growth inhibition screenings of a library of 367 compounds for β-lactam dependent inhibition of both L. monocytogenes and MSRA. We screened a library of 367 kinase inhibitors using growth inhibition assays similar to those reported in Examples 1 and 2.

Consistent with the results of Example 1, AZD5438 (FIG. 4) had an effective dose of 10 µM against L. monocytogenes. Consistent with the results of Example 2, GSK690693 (FIG. 6) had an effective dose of 10 µM against L. monocytogenes.

Figure 8:
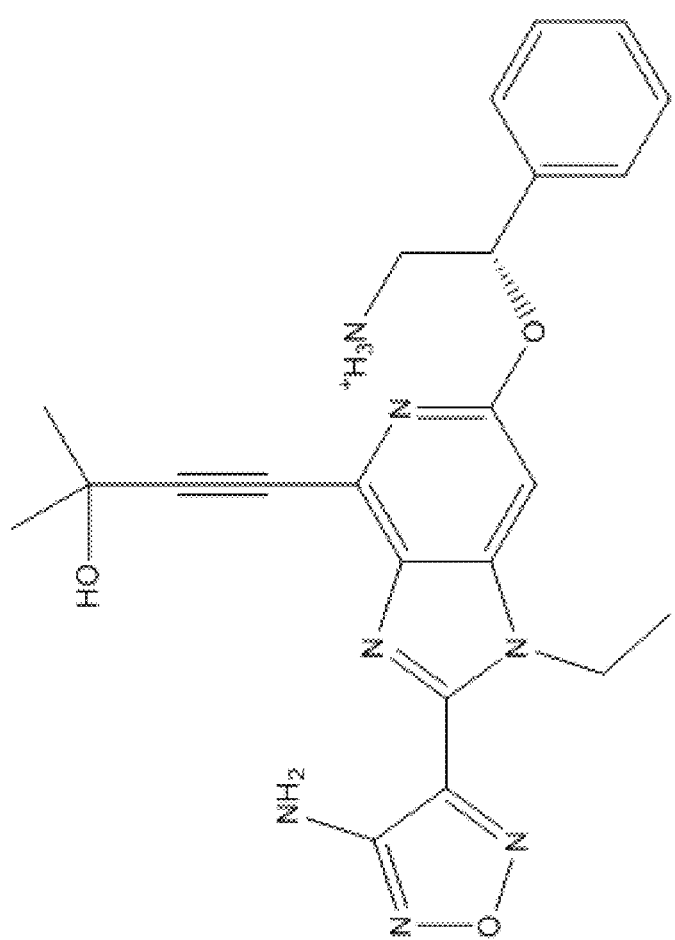
FIG. 8 shows the chemical structure of the Akt inhibitor GSK1007102B.
Figure 9:
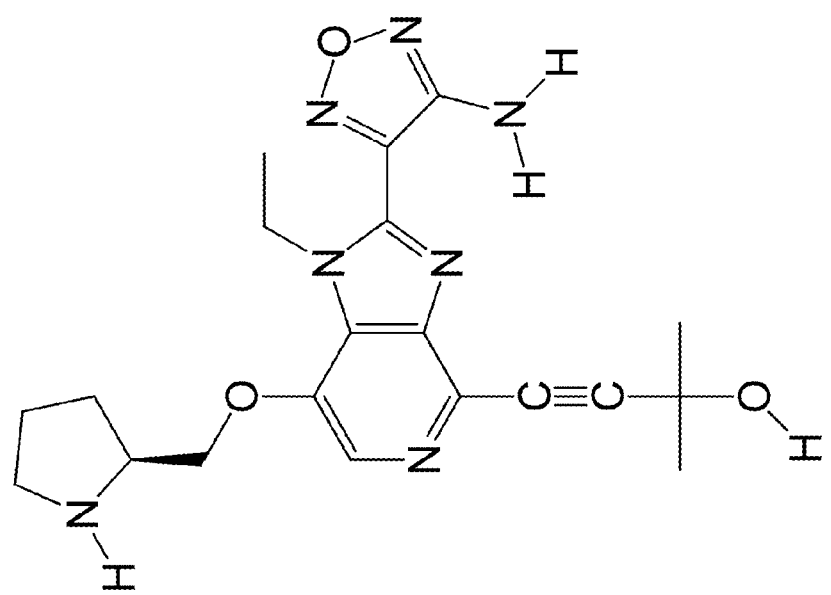
FIG. 9 shows the chemical structure of the RET inhibitor GSK614526A.
Figure 10:
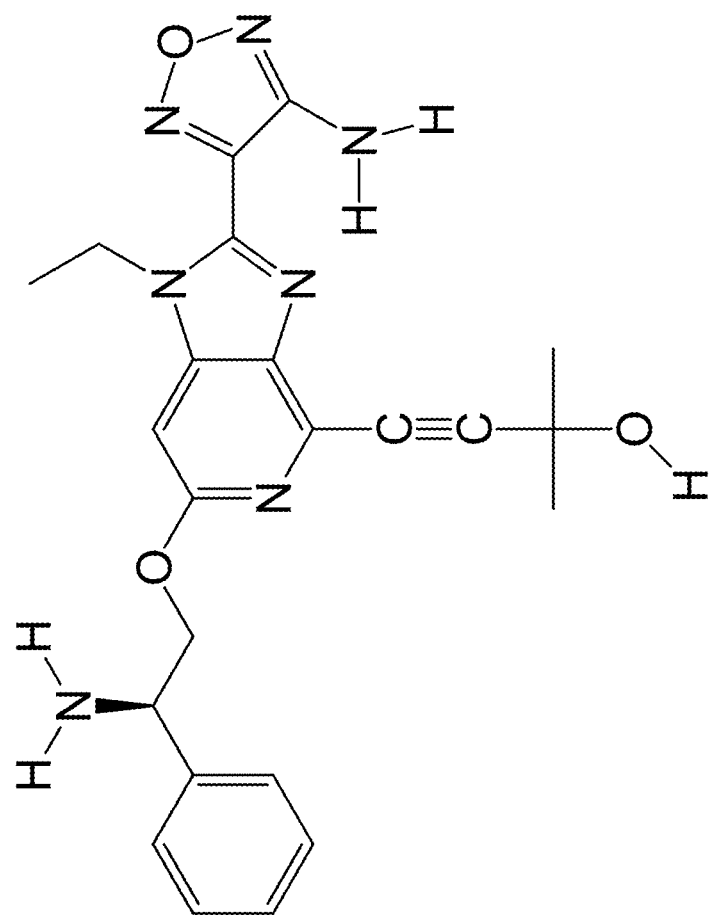
FIG. 10 shows the chemical structure of the Akt inhibitor GSK943949A.

GSK1007102B (FIG. 8) had effective doses of 10 µM, 2 µM, and 400 nM against L. monocytogenes. GSK614526A (FIG. 9) had effective doses of 10 µM and 2 µM against L. monocytogenes. GSK943949A (FIG. 10) had effective doses of 10 µM and 2 µM against L. monocytogenes.

Figure 11:
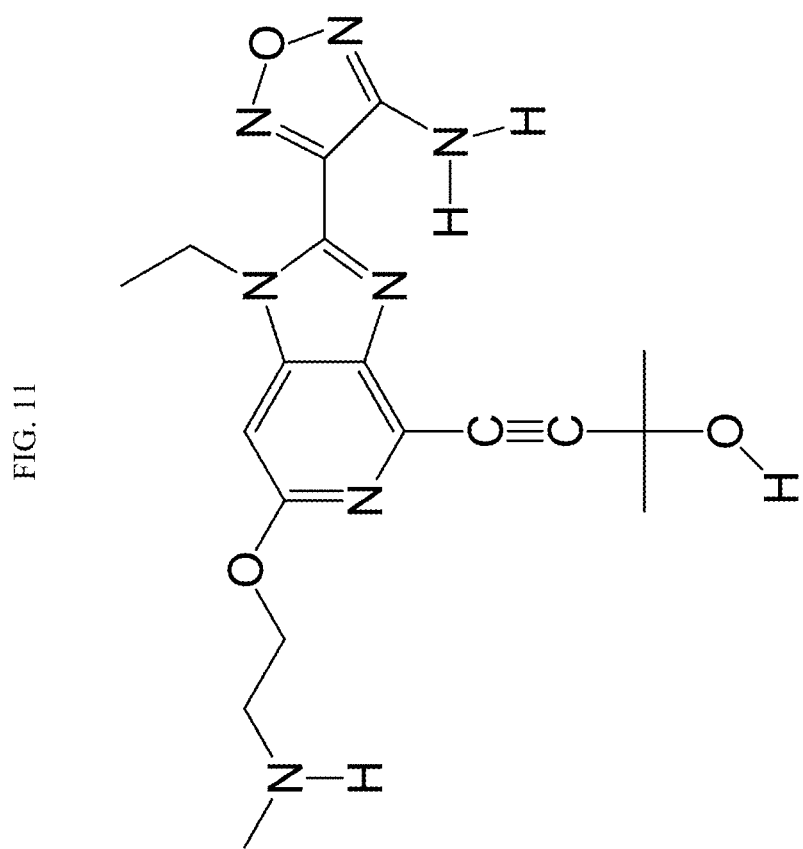
FIG. 11 shows the chemical structure of the Akt inhibitor GSK949675A.

GSK949675A (FIG. 11) was effective against both L. monocytogenes and MSRA, and exhibited an effective dose of 10 µM.

Figure 12:
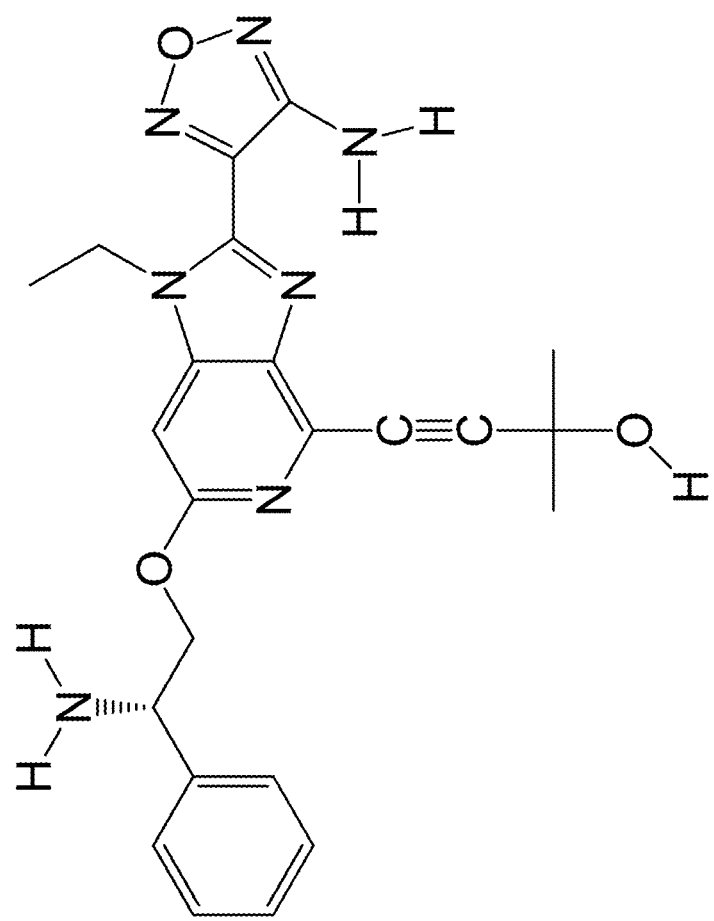
FIG. 12 shows the chemical structure of the Akt inhibitor GSK938890A.

GSK938890 (FIG. 12) had an effective dose of 10 µM against L. monocytogenes.

Example 4

Using Rational Design to Develop Kinase Inhibitors as Drugs for Antibiotic Resistant Bacteria In this Example, we extend the results disclosed above. Specifically, using in silico docking models, in vitro biochemical data, and in vivo bacterial inhibition data, we demontstrate that the alkyne imidazopyridine aminofurizans (AIAs) having the scaffold disclosed above can be effectively used in synergy with β-lactam antibiotics to treat Mycobacterium and Listeria infections.

Introduction

Penicillin binding protein And Ser/Thr kinase Associated (PASTA) kinases are integral membrane kinases that can bind to peptidoglycan fragments and are associated with cell wall maintenance. In silico docking studies have revealed several human kinase inhibitors that may bind well to PASTA kinases, and inhibition of these kinases has been shown to prevent bacterial growth (M. smegmatis [PknB]) or sensitize bacteria to β-lactam antibiotics (M. smegmatis [PknB], L. monocytogenes [PrkA], S. aureus [Stk1]). One class of compounds, the alkyne imidazopyridine aminofurizans, has promising in vitro biochemical and in vivo bacteriological inhibition, and these compounds provide a scaffold for drug optimization.

Methods and Results

In silico docking indicated that AIAs bind to bacterial PASTA kinases with nanomolar or better affinity.

Figure 13A:
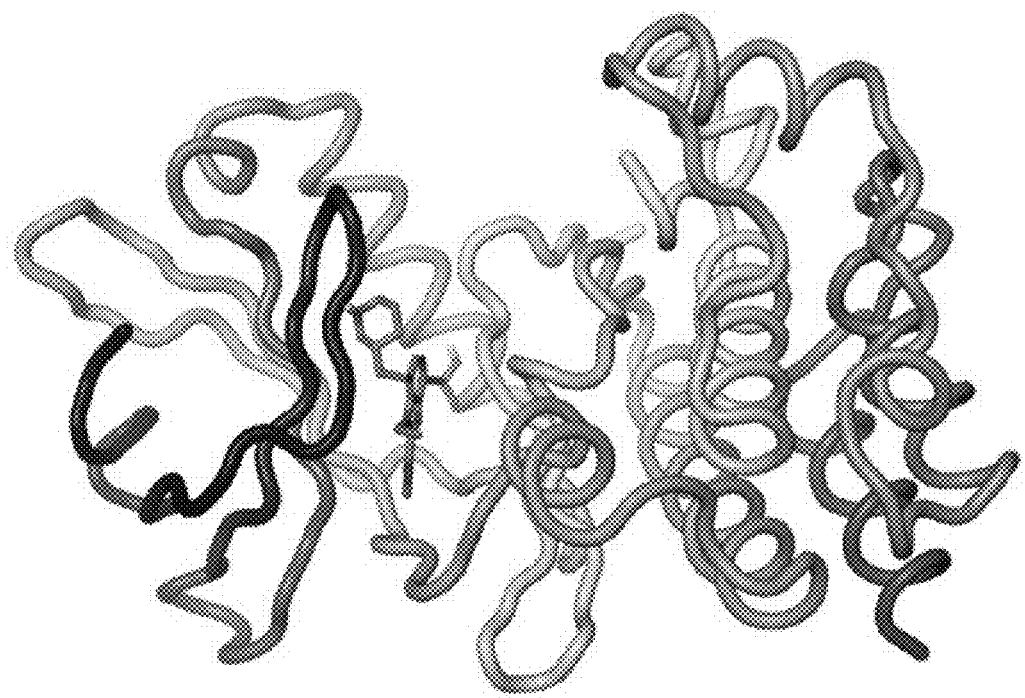
FIG. 13A is a global view showing GSK 690693 docked in PknB
Figure 13B:
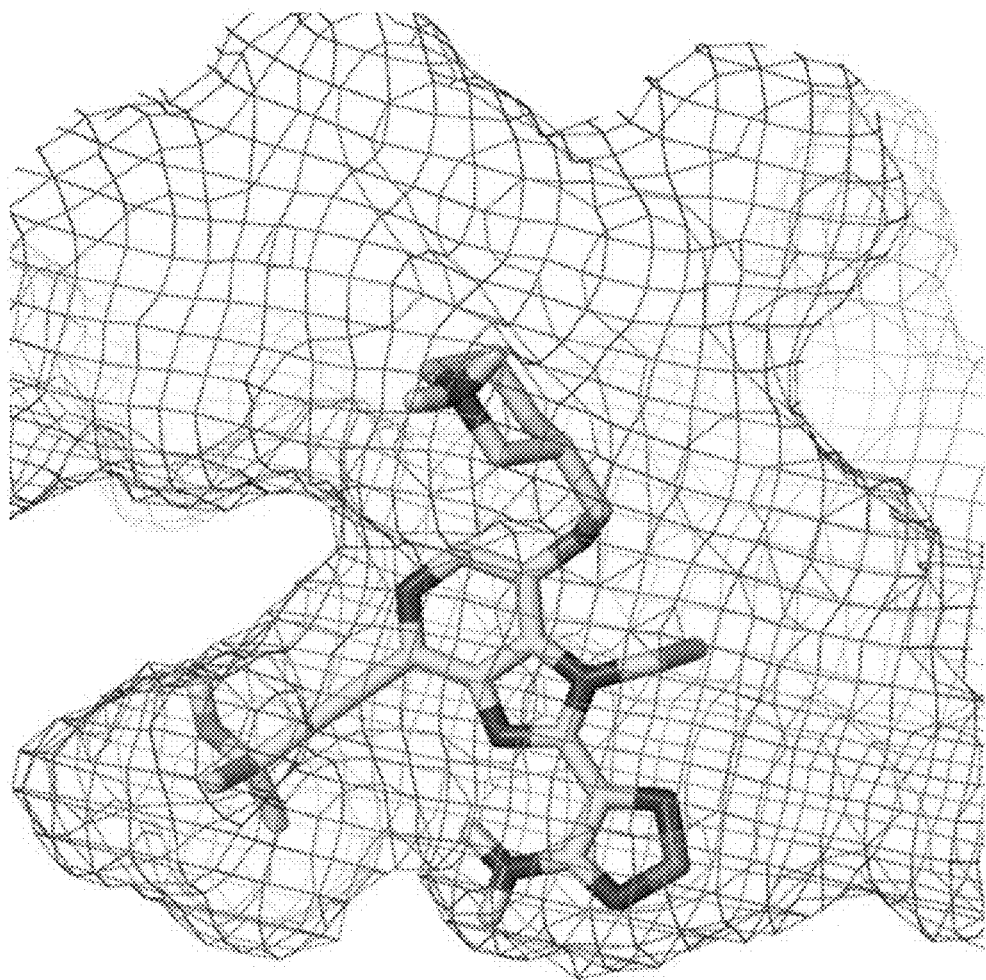
FIG. 13B is a local view showing GSK 690693 docked within the active site of PknB
Figure 13C:
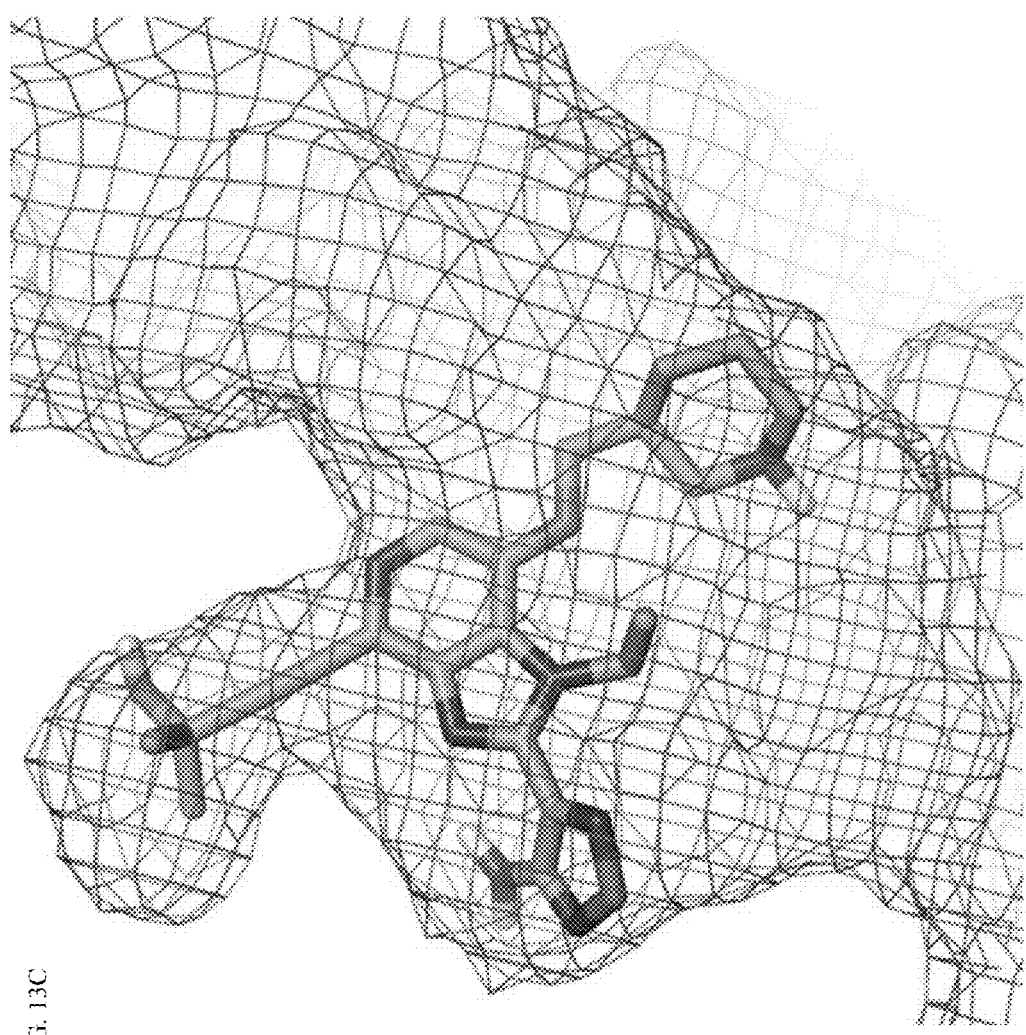
FIG. 13C is a local view showing GSK 690693 docked within the active site of PrkA.
Figure 13D:
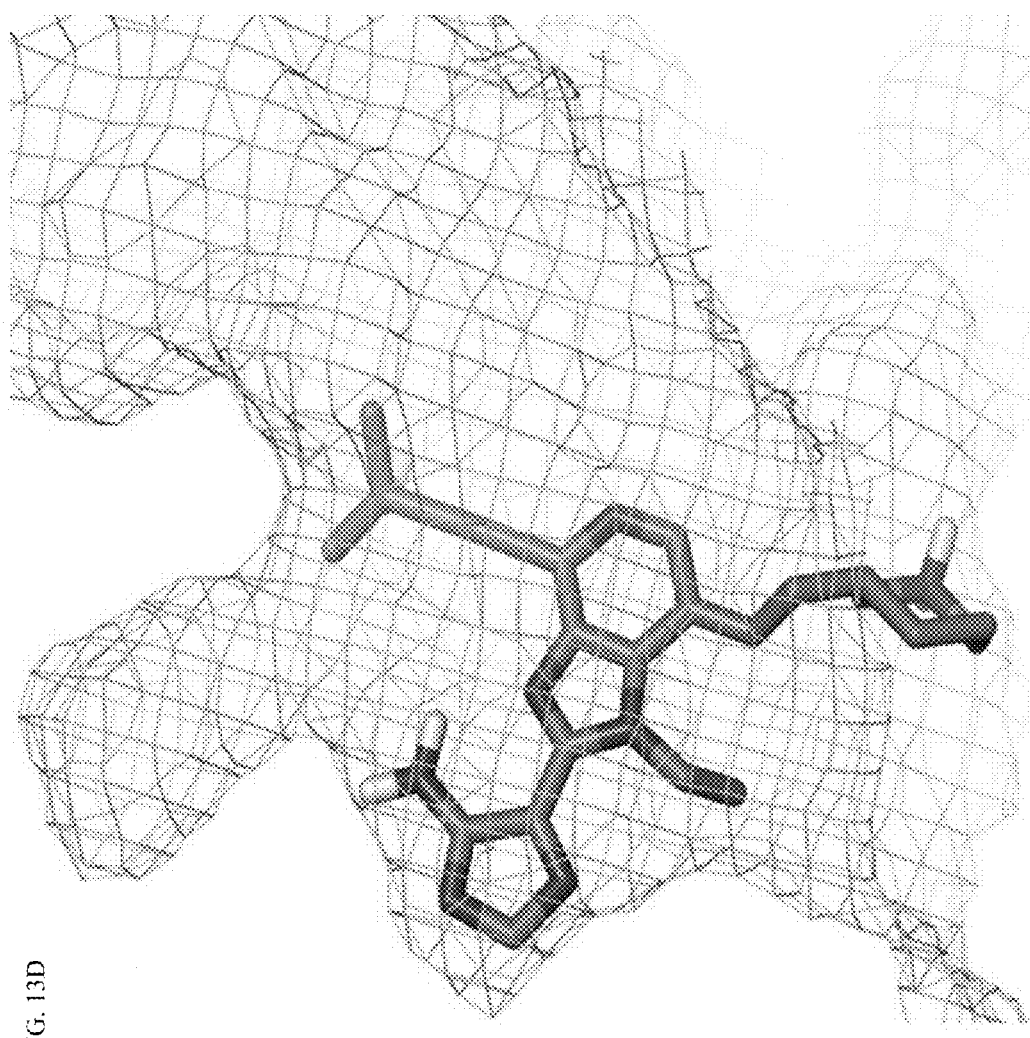
FIG. 13D is a local view showing GSK 690693 docked within the active site of Stk1.
Figure 13E:
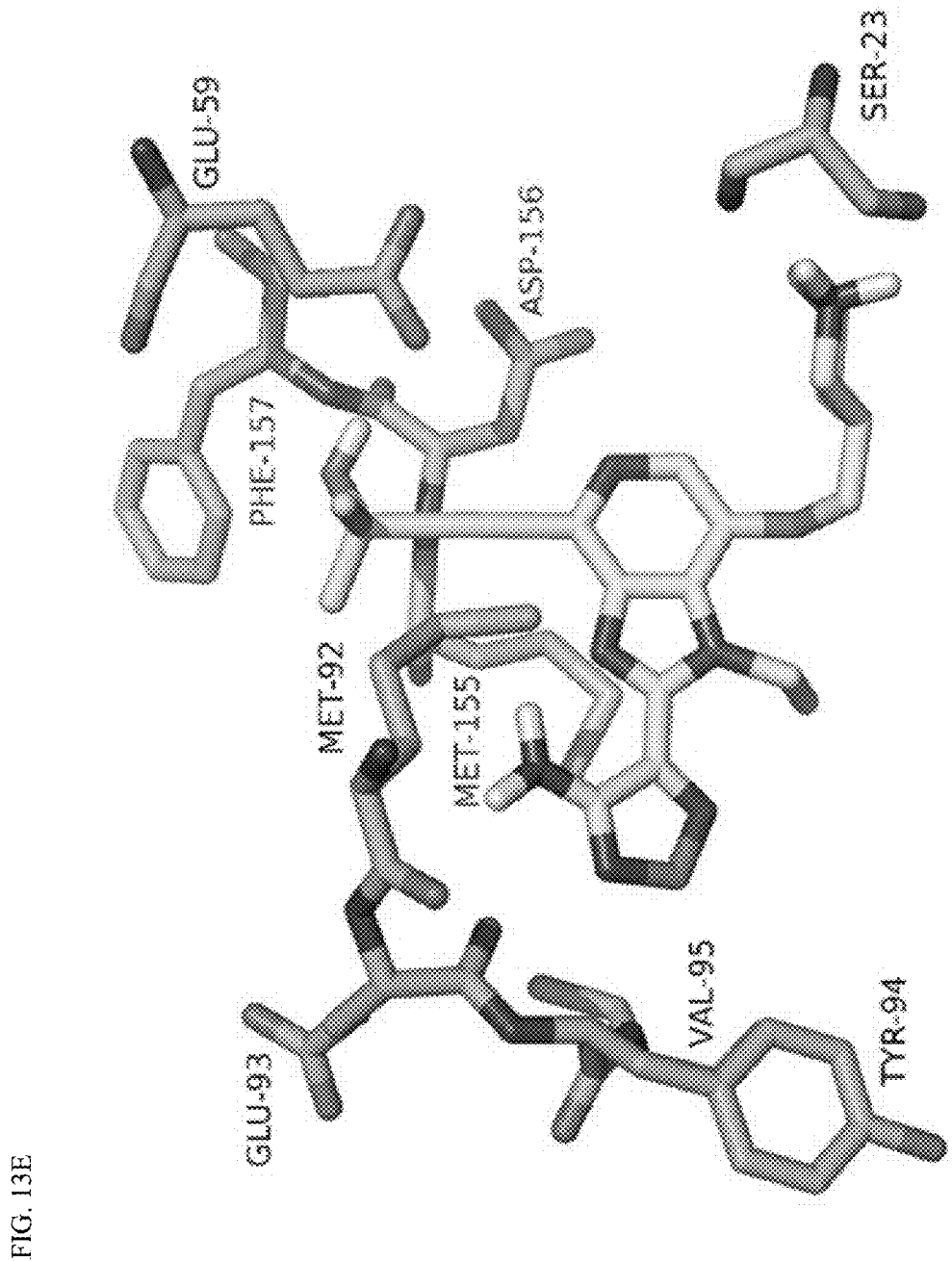
FIG. 13E is a local view showing the hydrogen bonds and stacking interactions of GSK 690693 with several residues in the PknB ATP binding pocket.

Autodock4 (Scripps) was used to dock human kinase inhibitors in models of PknB (106Y) and models of PrkA and Stk1 created by using iTasser to string the primary sequence onto 106Y. GSK690693 (FIG. 6) docks in PknB (FIGS. 13A and 13B), PrkA (FIG. 13C), and Stk1 (FIG. 13D). The alkyne group of GSK690693 preferentially docks in the back pocket of the active site. The pocket of PknB (FIG. 13B) and PrkA (FIG. 13C) is larger than in Stk1 (FIG. 13D), and allows for deeper binding in the active site, yielding more protein-ligand interactions and buried surface area. GSK690693 makes hydrogen bonds and stacking interactions with several residues in the PknB ATP binding pocket (FIG. 13E). Other AIAs follow a similar pattern to GSK 690693.

Human kinases have structural features absent in bacterial PASTA kinases that may be exploited for drug optimization.

Figure 14A:
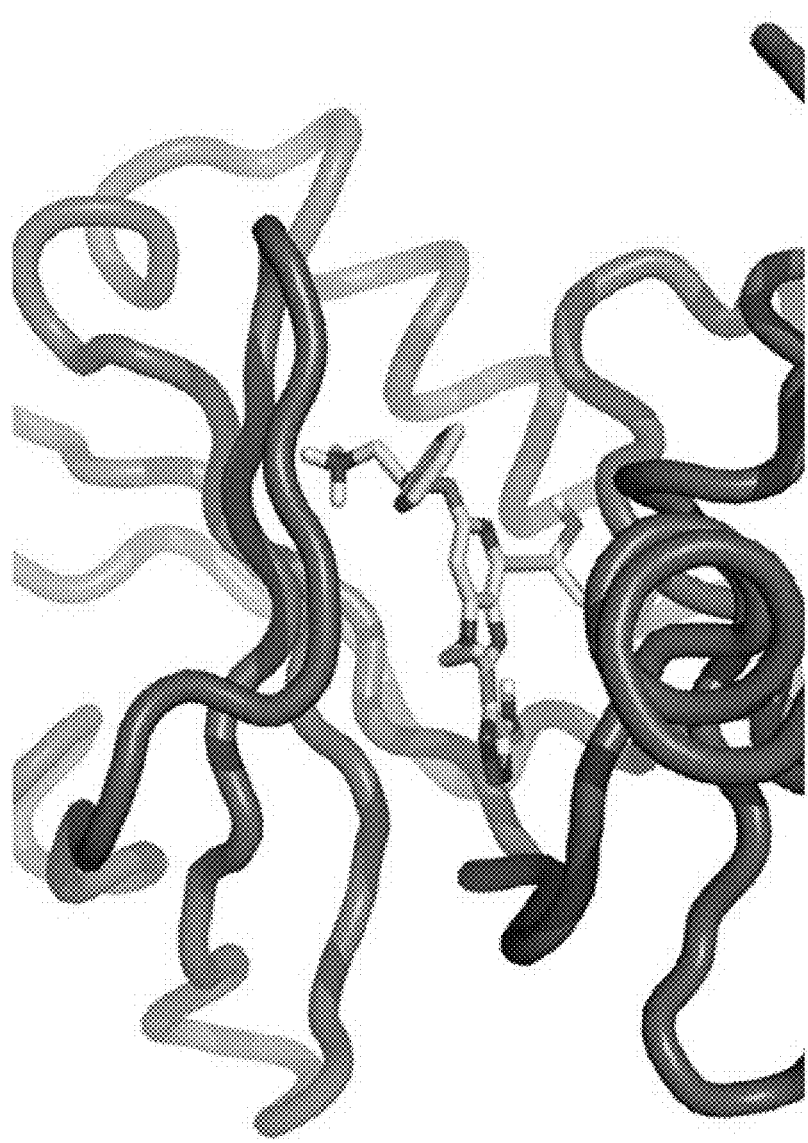
FIG. 14A shows the structure of the PknB backbone near the active site, with GSK 690693 in the center for reference.
Figure 14B:
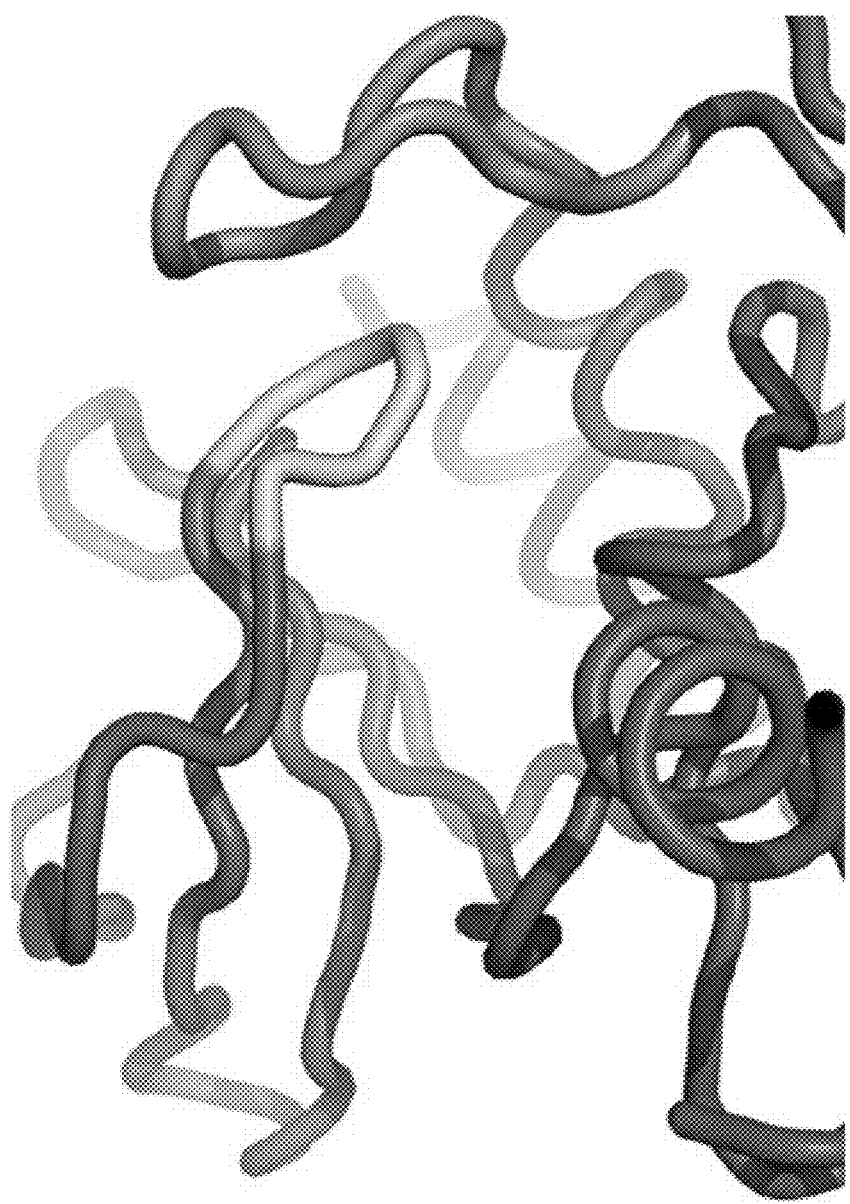
FIG. 14B shows the structure of the backbone of human kinase CDK2 near the active site.
Figure 14C:
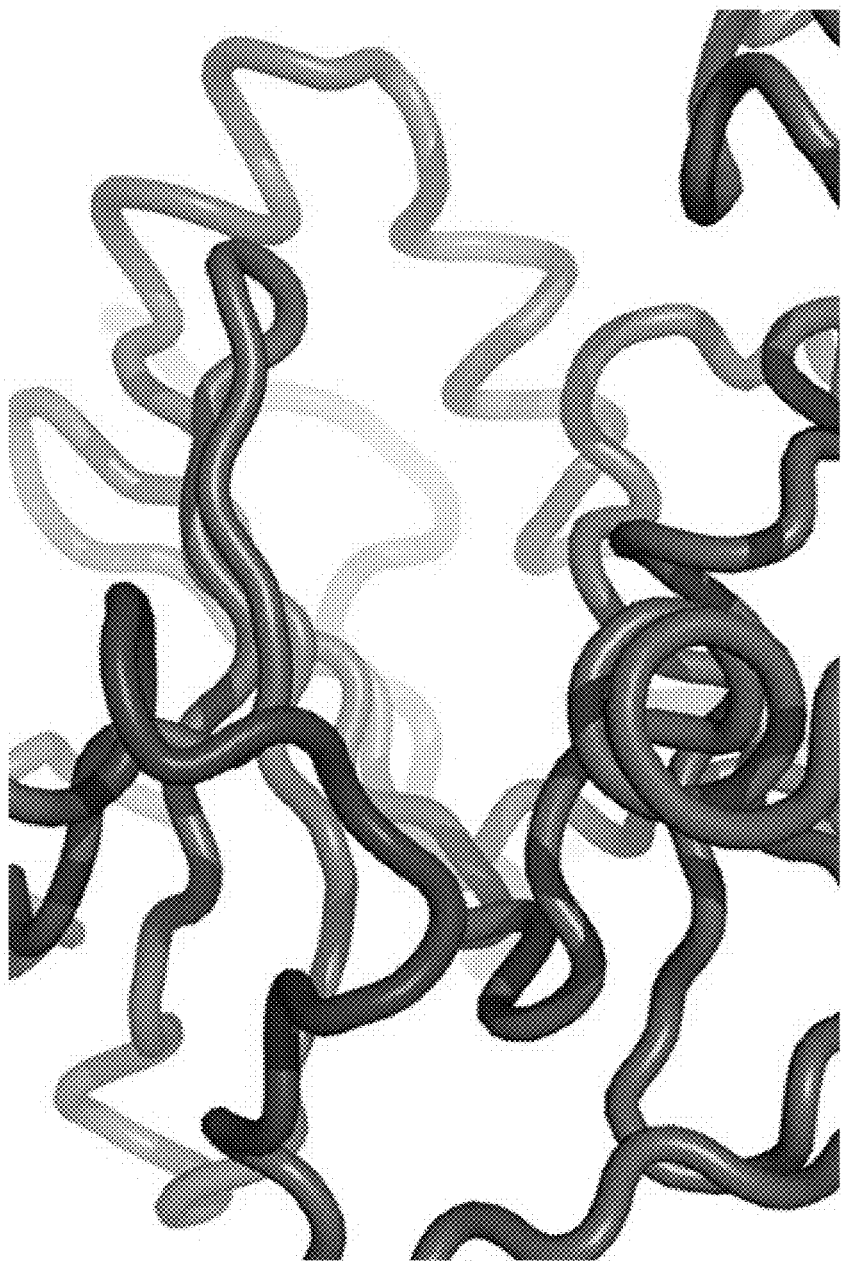
FIG. 14C shows the structure of the backbone of human kinase AKT2 near the active site.

Structures of human kinases CDK2 (4EK3) and AKT2 (3DOE) were aligned with PknB (106Y) using Pymol (Schrödinger). FIG. 14A shows the structure of PknB backbone, with GSK 690693 in the center for reference. As seen in FIG. 14B, CDK2 possesses a side flanking loop (far right) which forms a depression (right center) in the loop above the active site. As seen in FIG. 14C, AK2T possesses a C-terminal loop (foreground of center top quadrant) which flanks the opposite side of the binding site. These structural features can be used to optimize differential drug binding to bacterial PASTA kinases in preference to human kinases.

GSK690693 can inhibit PknB and PrkA enzymatic activity in vitro.

Figure 15A:
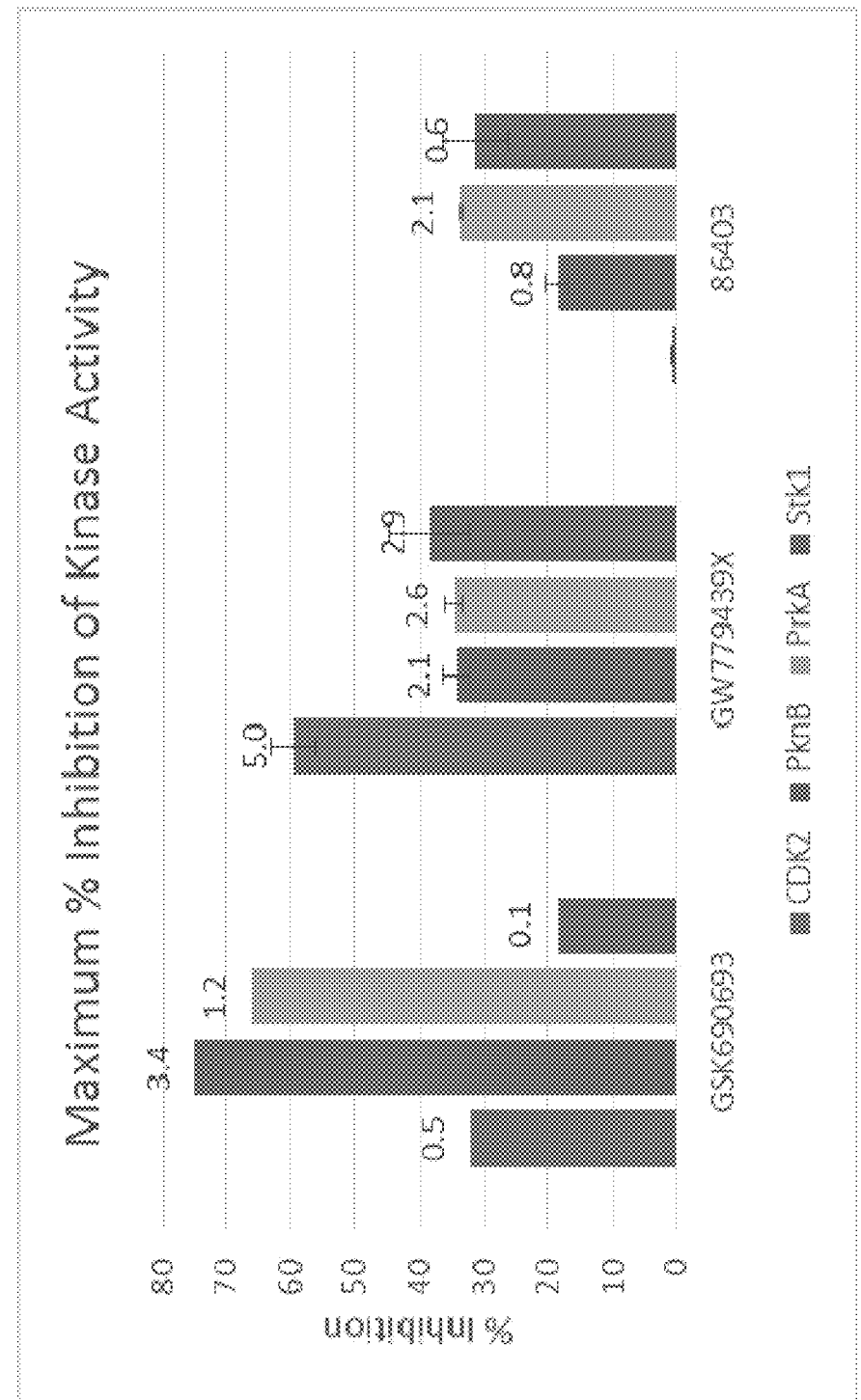
FIG. 15A is a bar graph showing the results of the Kinase-Glo® assay testing the efficacy of the kinase inhibitors GSK690693, GW779439X and 864403 on CDK2, PknB, PrkA, and Stk1. Biochemical IC50s are indicated in the numbers each sample.
Figure 15B:
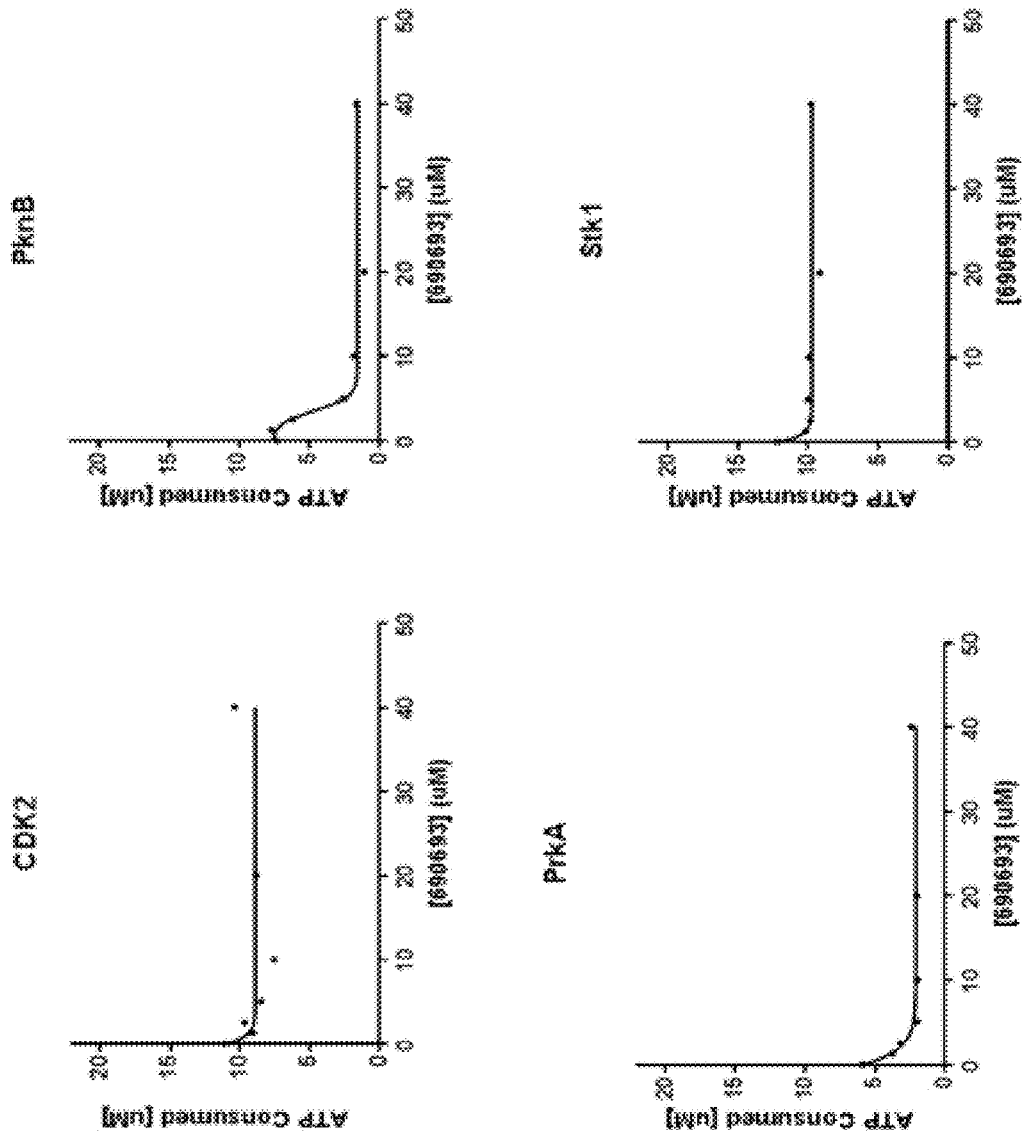
FIG. 15B shows the inhibition curve that results from using GSK690693 on CDK2, PknB, PrkA, and Stk1.

The Kinase-Glo® assay (Promega) was used to test the efficacy of kinase inhibitors on CDK2, PknB, PrkA, and Stk1. In brief, 2.3 µM of kinase (normalized by Bradford assay and visualized on SDS-PAGE) was incubated with 0-40 µM of GSK690693, GW779439X, or 86403 for 10 minutes at 37° C. After incubation, 20 µM of ATP and 10 µM of myelin basic protein (MBP) were added and the phosphorylation reaction was carried out at 37° C. for 1 hour. The reaction was stopped by the addition of 50 µL of Kinase-Glo® reagent and luminescence was measured in a Synergy HT plate reader (BioTek). A standard curve was used to quantify ATP consumption based on measured luminescence, and the maximum percent inhibition of kinase activity was calculated for each combination (FIG. 15A). GSK690693 can inhibit PknB and PrkA more efficiently than Stk1 and is more effective than GW779439X and 86403. Inhibition curves are shown in FIG. 15B for reference.

Alkyne imidazopyridine aminofurazans have in vivo activity against *M. smegmatis* and *L. monocytogenes* but not *S. aureus*.

Figure 16A:
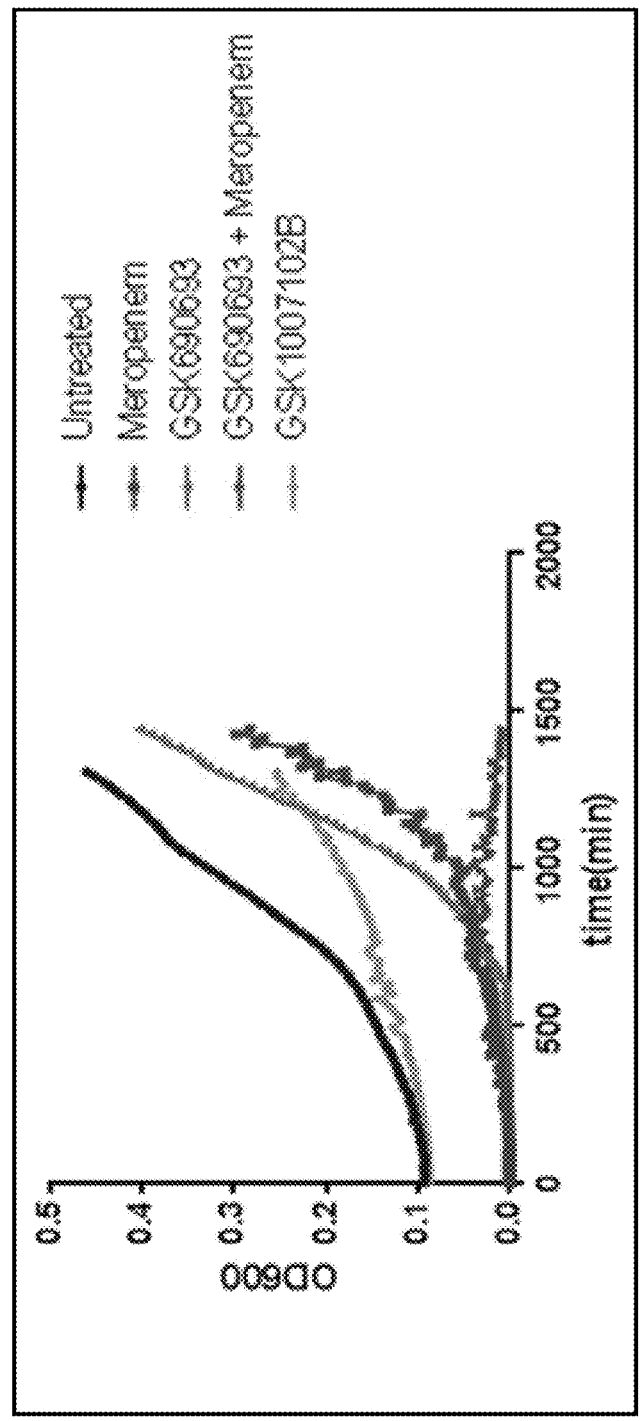
FIG. 16A shows growth curves for M. smegmatis in cultures that are untreated, treated with Miropenem, treated with GSK690693, treated with GSK690693 in combination with Miropenem, and treated with GSK1007102B.
Figure 16B:
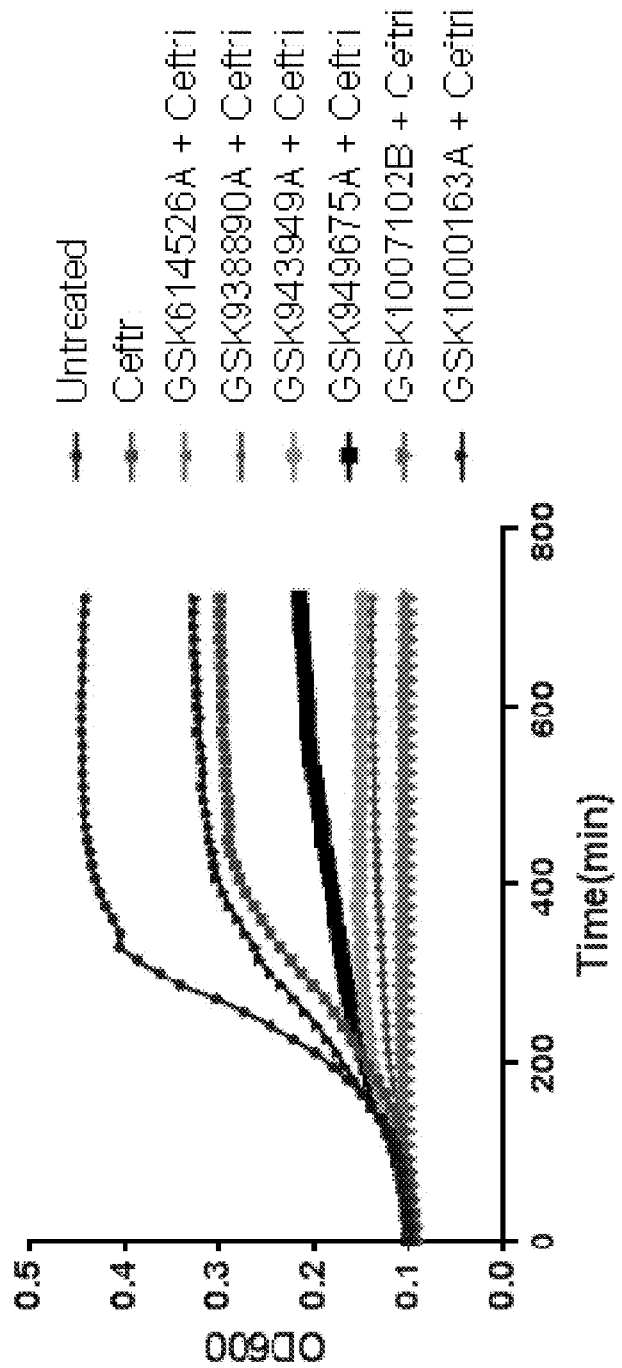
FIG. 16B shows growth curves for L. monocytogenes in cultures that are untreated, treated with Ceftrioxone, and treated with Ceftrioxone in combination with each of 5 kinase inhibitors (GSK614526A, GSK938890A, GSK943949A, GSK949675A, and GSK1007102B).
Figure 16C:
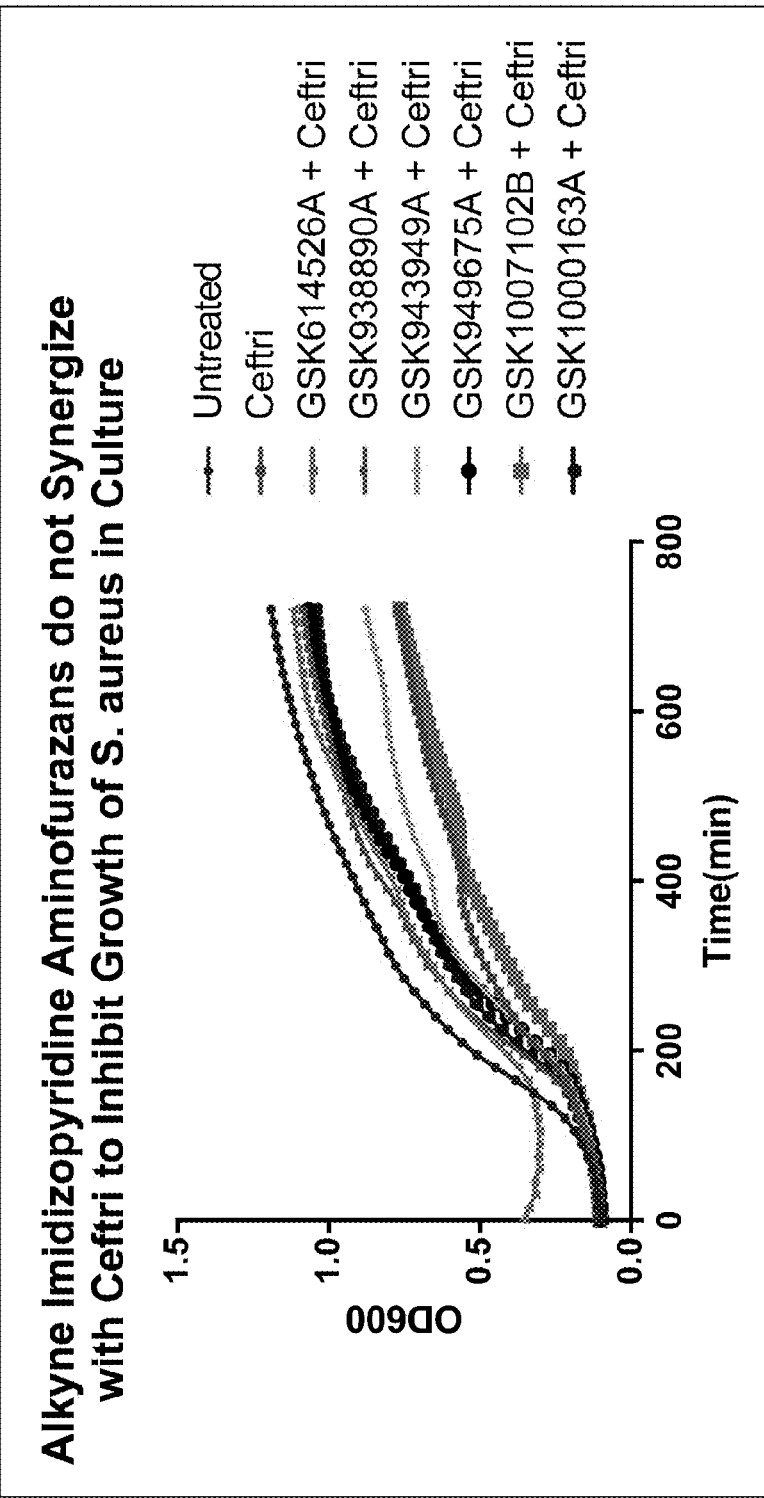
FIG. 16C shows growth curves for S. aureus in cultures that are untreated, treated with Ceftrioxone, and treated with Ceftrioxone in combination with each of 5 kinase inhibitors (GSK614526A, GSK938890A, GSK943949A, GSK949675A, and GSK1007102B).

Various AIA drugs were administered at 10 µM concentration to *M. smegmatis, L. monocytogenes*, and *S. aureus*. As shown in FIG. 16A, GSK690693 exhibits synergy with meropenem against *M. smegmatis*, and GSK1007102B has a minor affect on growth without additional drugs. As shown in FIG. 16B, most, but not all, AIAs exhibit synergy with ceftriaxone against *L. monocytogenes*. As shown in FIG. 16C, AIAs do not exhibit synergy with ceftriaxone against *S. aureus*.

Alkyne imidazopyridine aminofurazans exhibit less host in vivo toxicity than other kinase inhibitors.

The zebrafish (*Danio rerio*) is a common model used to test drug toxicity. It is cost effective to test statistically significant numbers of organisms, and soluble drugs are easily administered in the water. The zebrafish kinases show high homology to higher eukaryotic kinases and several bacterial infection models are currently in use.

Figure 17:
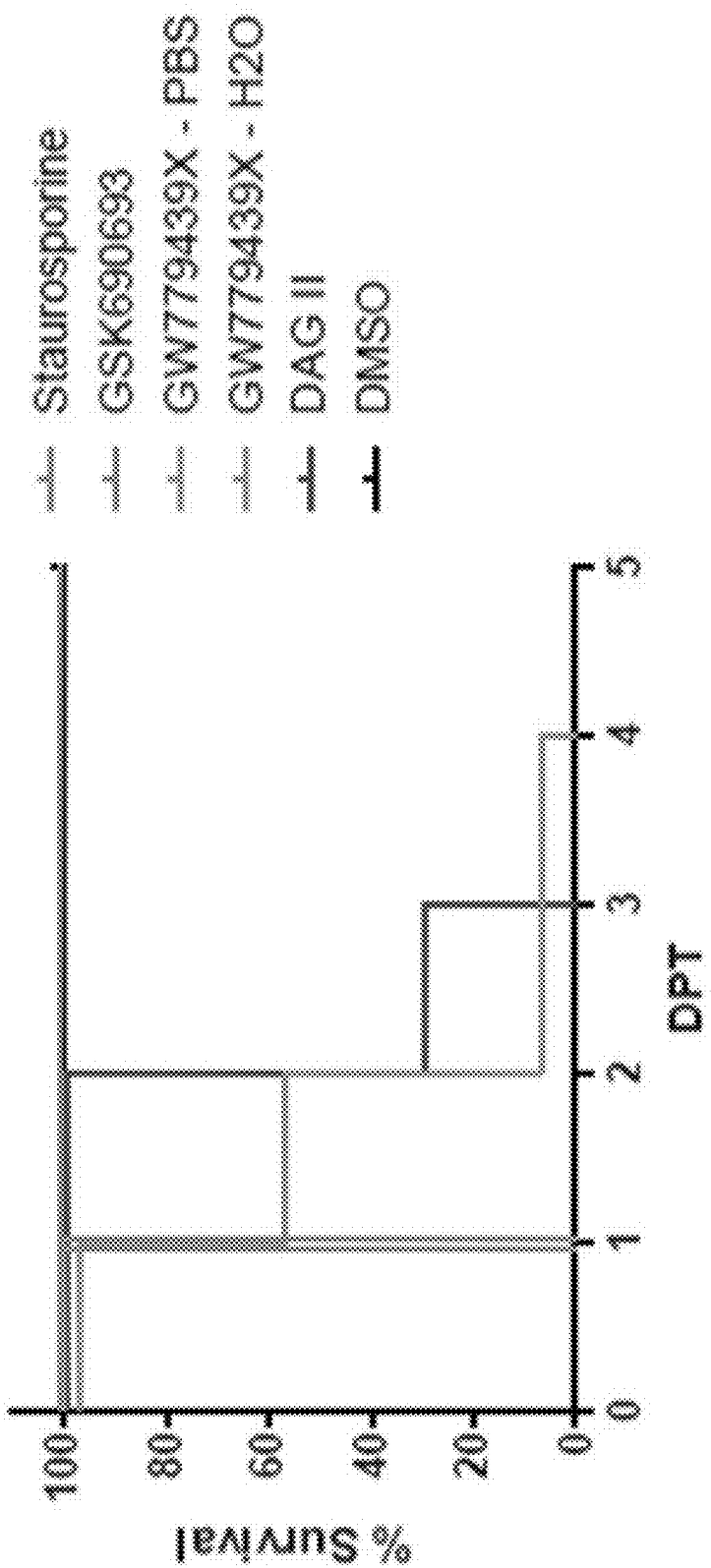
FIG. 17 is a graph showing the results of a zebrafish toxicity assay testing the toxicity of StStaurosporine, GSK690693, GW779439X with PBS, GW779439X with H$_2$O, DAG II, and DMSO.

Human kinase inhibitors were administered to zebrafish in their environment for for five days. As shown in FIG. 17, GSK690693 does not induce toxicity in zebrafish. In contrast, the CDK2 inhibitor GW779439X and the diacylglycerol kinase inhibitor II were highly toxic.

Conclusion

In silico docking of alkyne imidazopyridine aminofurazans (AIAs) in PknB reveal predicted $K_i$s in the low nanomolar range. Specifically, GSK690693 docks in PknB, PrkA, and Stk1 with $K_i$s of 6, 13, and 52 nM. However, the docked orientation of Stk1 varies significantly from the docked orientation in PknB, PrkA, and the co-crystal structure orientation within AKT2 (3DOE). GSK690693 can inhibit all three kinases biochemically, but shows a four-fold increase in inhibition for PknB and PrkA compared to Stk1.

Microbiologic assays support these data, as no AIA has been shown to have activity against *S. aureus*, and most AIAs tested with *L. monocytogenes* can inhibit growth in concert with ceftriaxone (GSK690693, GSK1007102B, GSK949675A, GSK943949A, GSK938890A, and GSK614526A). One of the AIAs tested did not exhibit such synergistic activity (GSK1000163A). In *M. smegmatis*, GSK690693 can work to inhibit growth synergistically with meropenem, and another AIA, GSK1007102B, in addition to showing such a synergistic effect, even shows inhibition in the absence of a β-lactam. None of the other tested AIAs (GSK1000163A, GSK949675A, GSK943949A, GSK938890A, and GSK614526A) shows synergistic activity against *M. smegmatis*.

These data suggest that PASTA kinase inhibitors having the alkyne imidazopyridine aminofurazan scaffold can be effectively used synergistically with β-lactams to more effectively treat *Listeria* and *Mycobacterium* infections, particularly in cases where the infectious bacterium has developed antibiotic resistance.

Example 5

Predicted Binding Energies for Known AIA Kinase Inhibitors Docked to PknB

Figure 6:
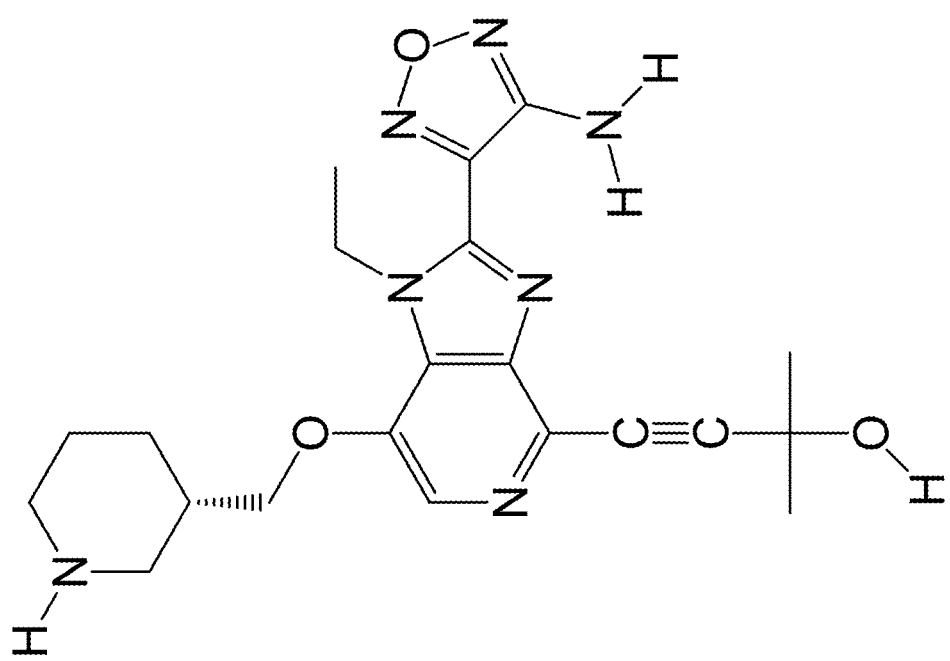
FIG. 6 shows the chemical structure of the Akt inhibitor GSK690693.
Figure 7:
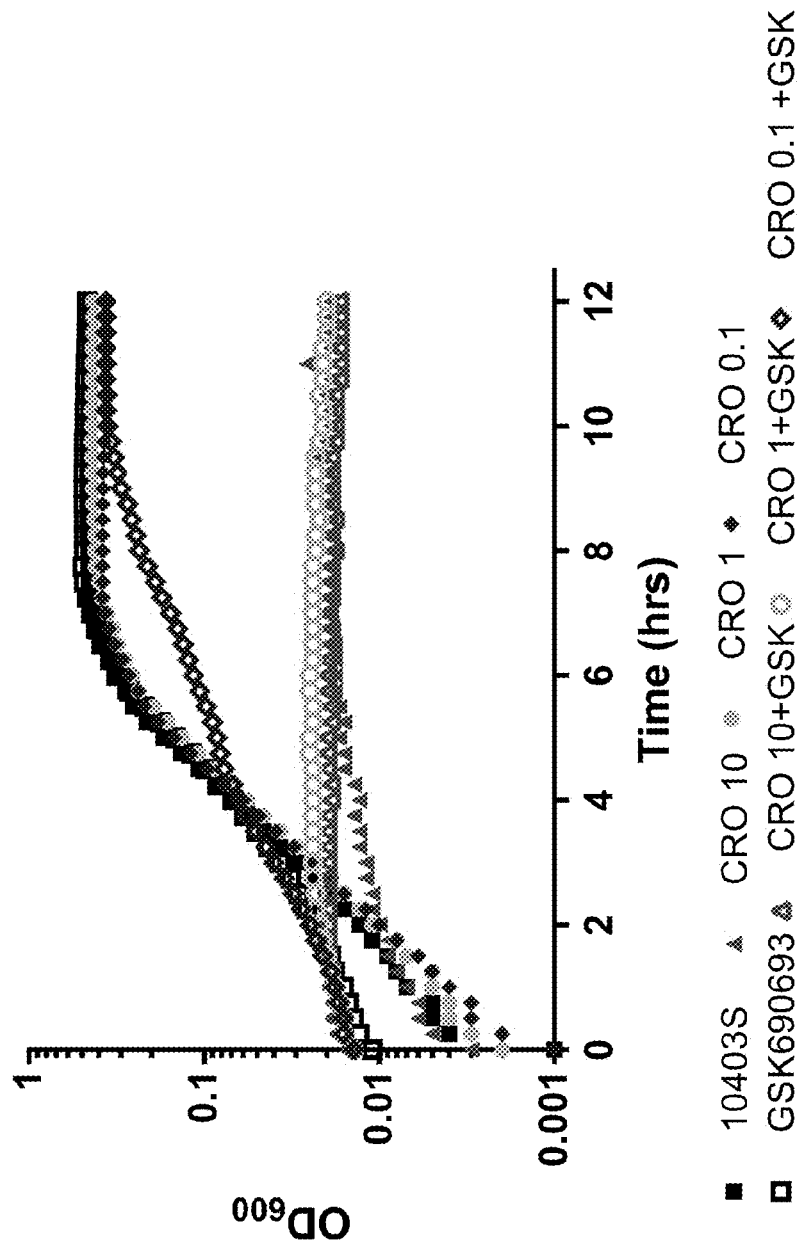
FIG. 7. GSK690693 also sensitizes L. monocytogenes to β-lactam treatment through inhibition of PrkA. Overnight cultures of wild type L. monocytogenes were back diluted and treated with 10-fold serial dilutions of ceftriaxone in the presence (open shape) or absence (closed shape) of 100 μM GSK690693. Antibiotic concentrations are μg/ml. Growth was analyzed for 12 hours at 15 minute intervals. Data are representative of at least 3 independent repeats.
Figure 18:
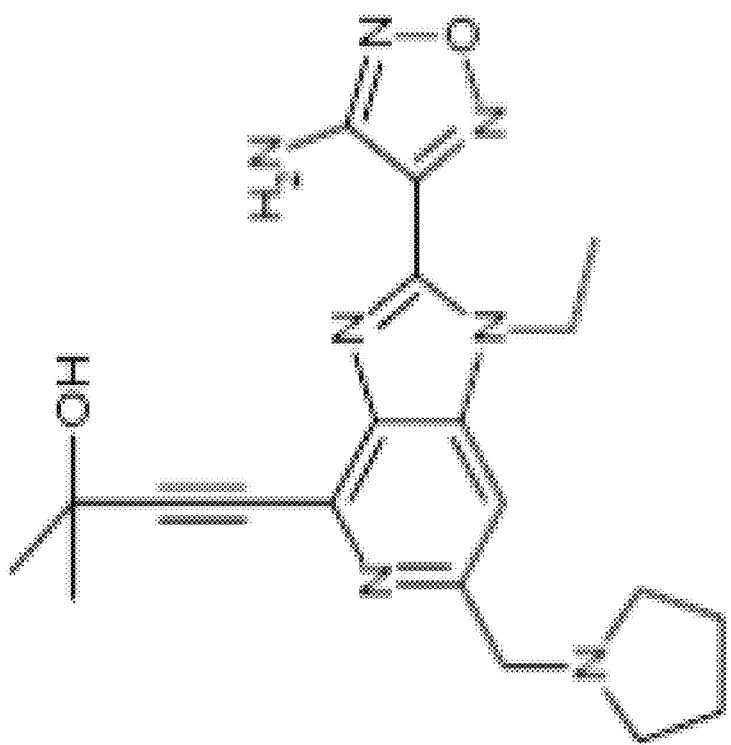
FIG. 18 shows the chemical structure of the AIA kinase inhibitor GW1000163A.

In this Example, we used in silico docking to predict the binding energies (kcal/mol) and $K_i$s (nM) of known AIA kinase inhibitors docked into the tuberculosis kinase PknB For compound GSK690693; see FIG. 6), the predicted binding energy is −11.19 kcal/mol, and the predicted $K_i$ is 6 nM. For compound GSK1007102B; see FIG. 8), the predicted binding energy is −10.44 kcal/mol, and the predicted $K_i$ is 17 nM. For compound GSK1007102B (; see FIG. 8), the predicted binding energy is −10.44 kcal/mol, and the predicted $K_i$ is 17 nM. For compound GW1000163A (see FIG. 18), the predicted binding energy is −10.44 kcal/mol, and the predicted $K_i$ is 14 nM. For compound GSK949675A; see FIG. 11), the predicted binding energy is −9.43 kcal/mol, and the predicted $K_i$ is 104 nM. For compound GSK943949A (a/k/a GSK943949A; see FIG. 10), the predicted binding energy is −10.19 kcal/mol, and the predicted $K_i$ is 34 nM. For compound GSK938890A; see FIG. 12), the predicted binding energy is −10.19 kcal/mol, and the predicted $K_i$ is 34 nM. For compound GSK614526A; see FIG. 9), the predicted binding energy is −10.15 kcal/mol, and the predicted $K_i$ is 36 nM.

These results confirm the potential utility of the AIA compounds in treating tuberculosis.

Example 6

Predicted Binding Energies for Synthetic AIA Analogs Docked to PknB

In this Example, we used in silico docking to predict the binding energies (kcal/mol) and $K_i$s (nM) of various synthetic analogs having the AIA scaffold docked into the tuberculosis kinase PknB A number of these analogs exhibited lower $K_i$s than the naturally occurring kinase inhibitors tested in Example 5 (and several exhibited substantially lower $K_i$s), indicating that they may potentially have greater efficacy in treating tuberculosis than the naturally occurring compounds.

Figure 19:
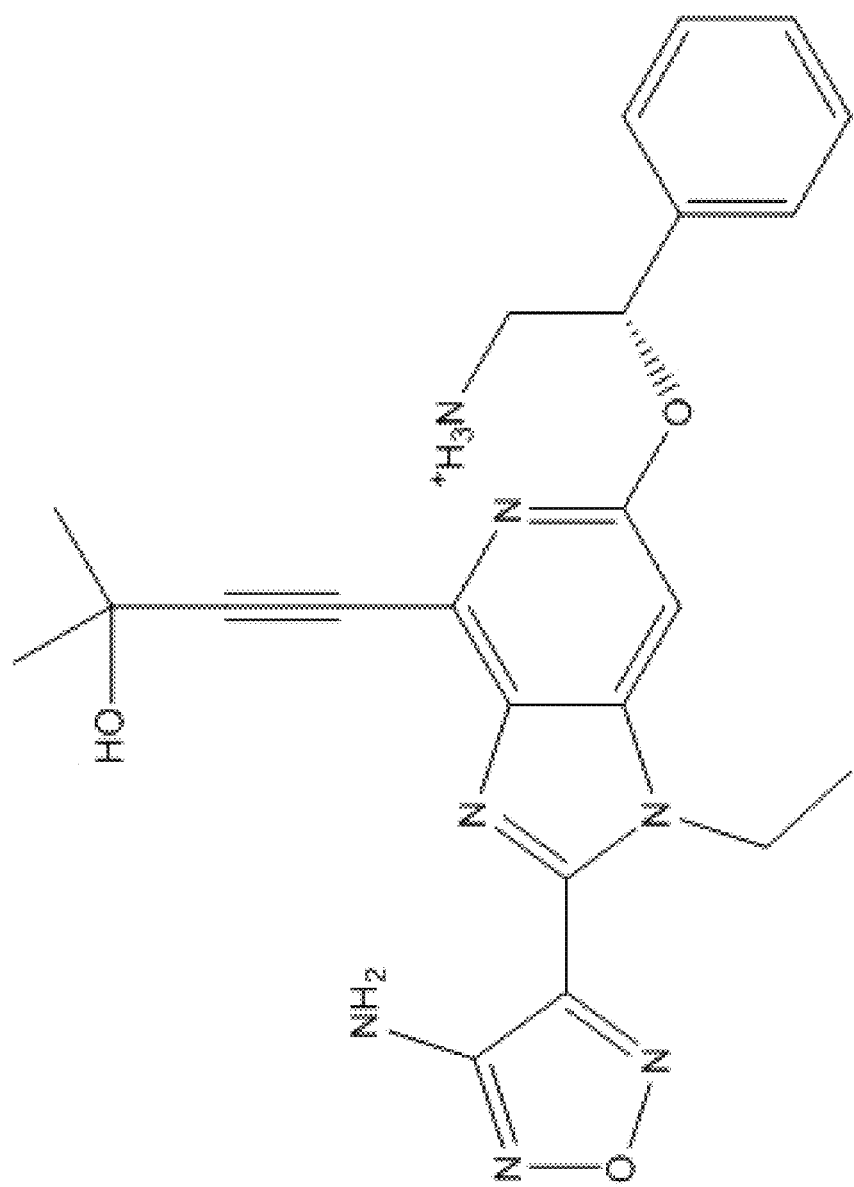
FIG. 19 shows the chemical structure of the AIA kinase inhibitor GSK1007102B-S.
Figure 20:
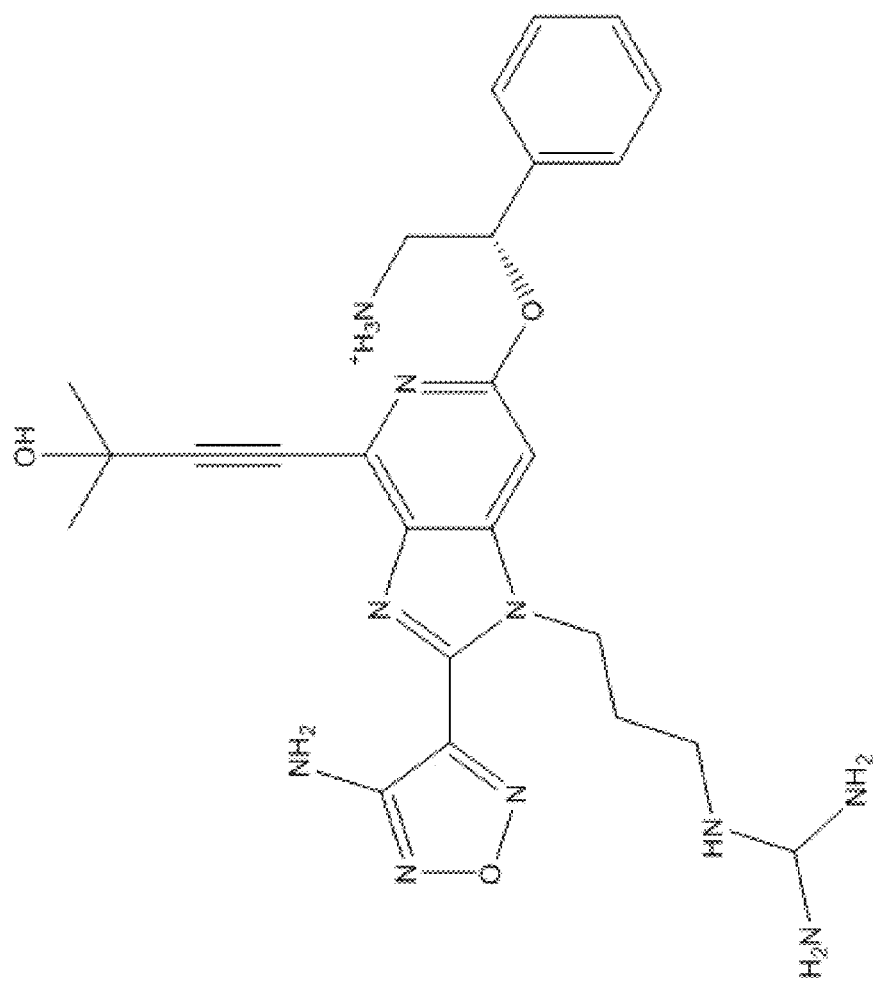
FIG. 20 shows the chemical structure of the AIA analog NW10015674728.
Figure 21:
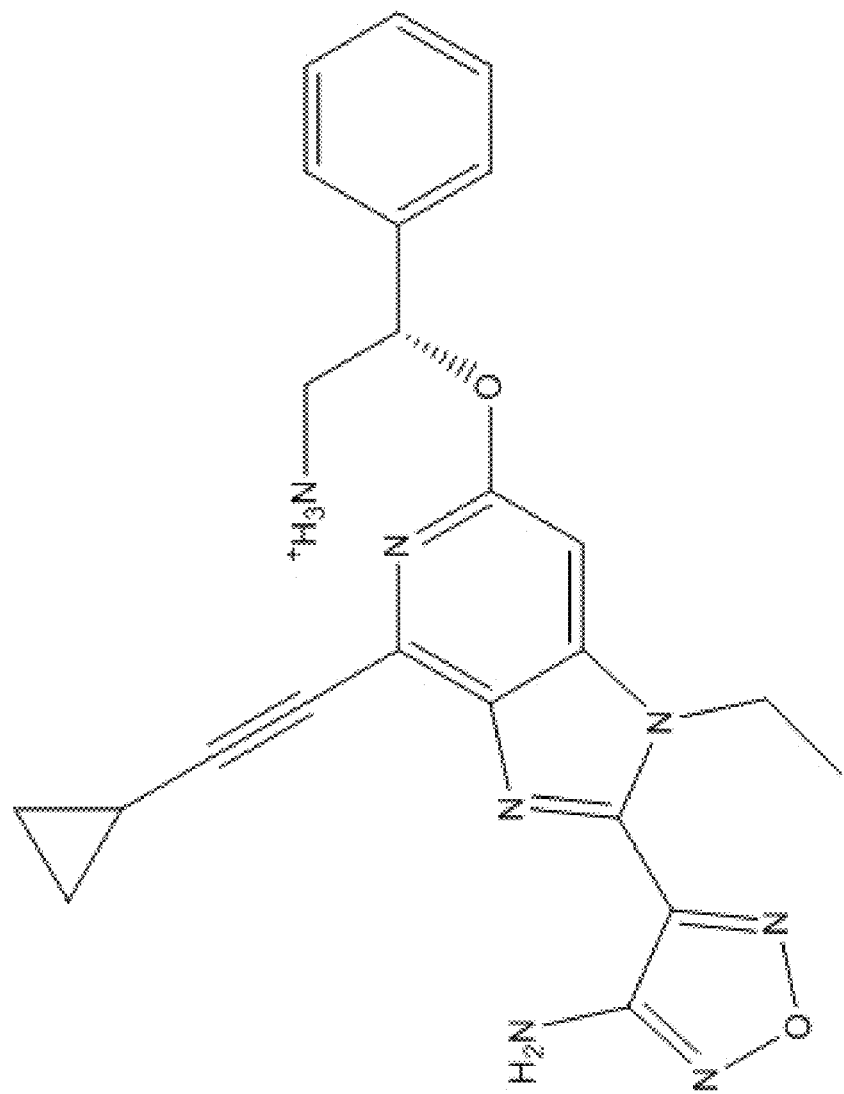
FIG. 21 shows the chemical structure of the AIA analog NW 10025670203.
Figure 22:
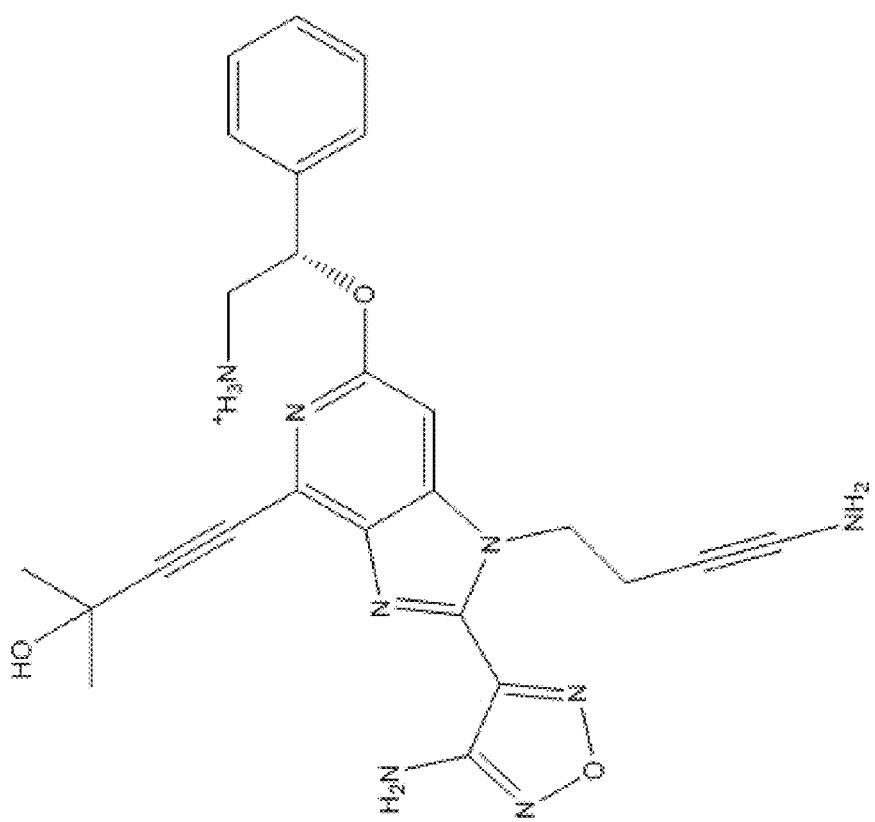
FIG. 22 shows the chemical structure of the AIA analog NW1003S674728.
Figure 23:
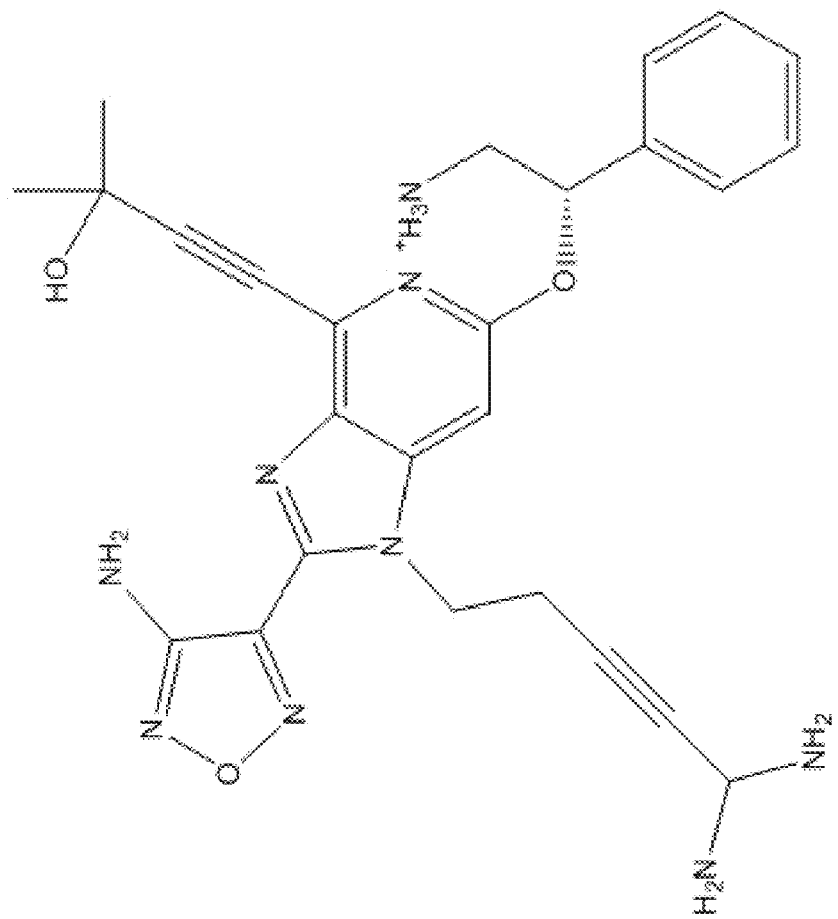
FIG. 23 shows the chemical structure of the AIA analog NW1004674728.
Figure 24:
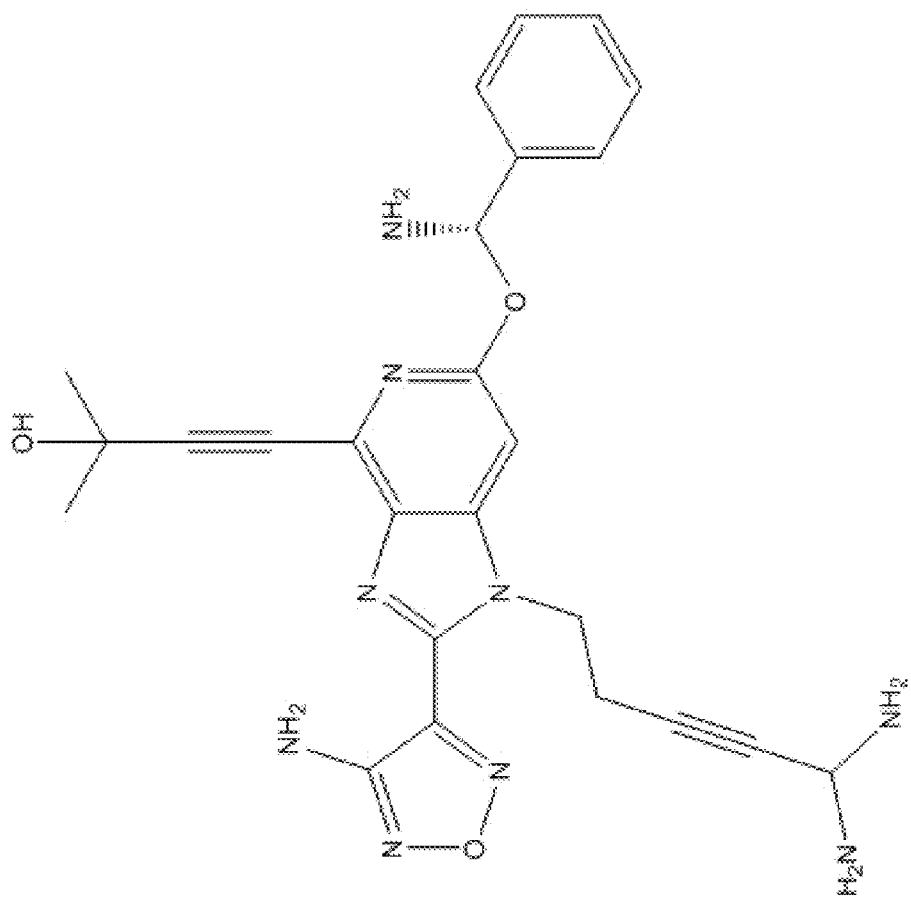
FIG. 24 shows the chemical structure of the AIA analog NW1005S674728.
Figure 25:
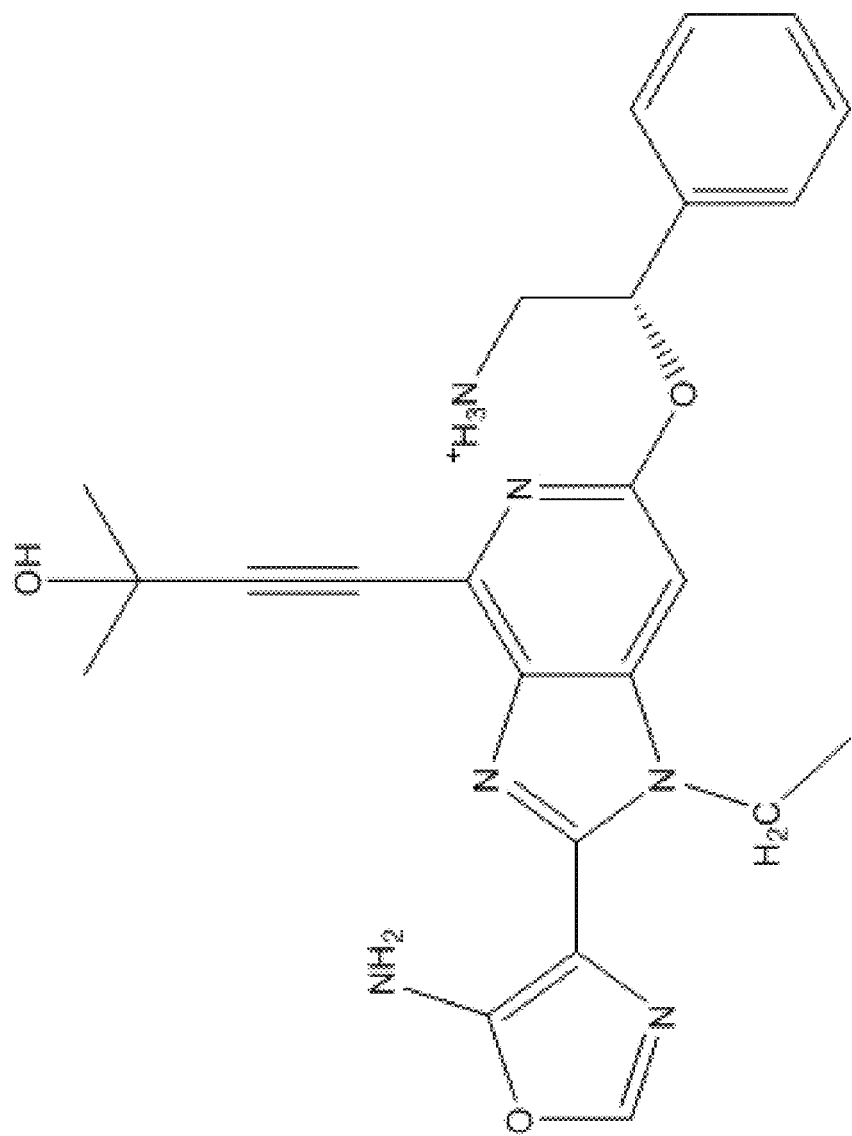
FIG. 25 shows the chemical structure of the AIA analog NW30015670228.
Figure 26:
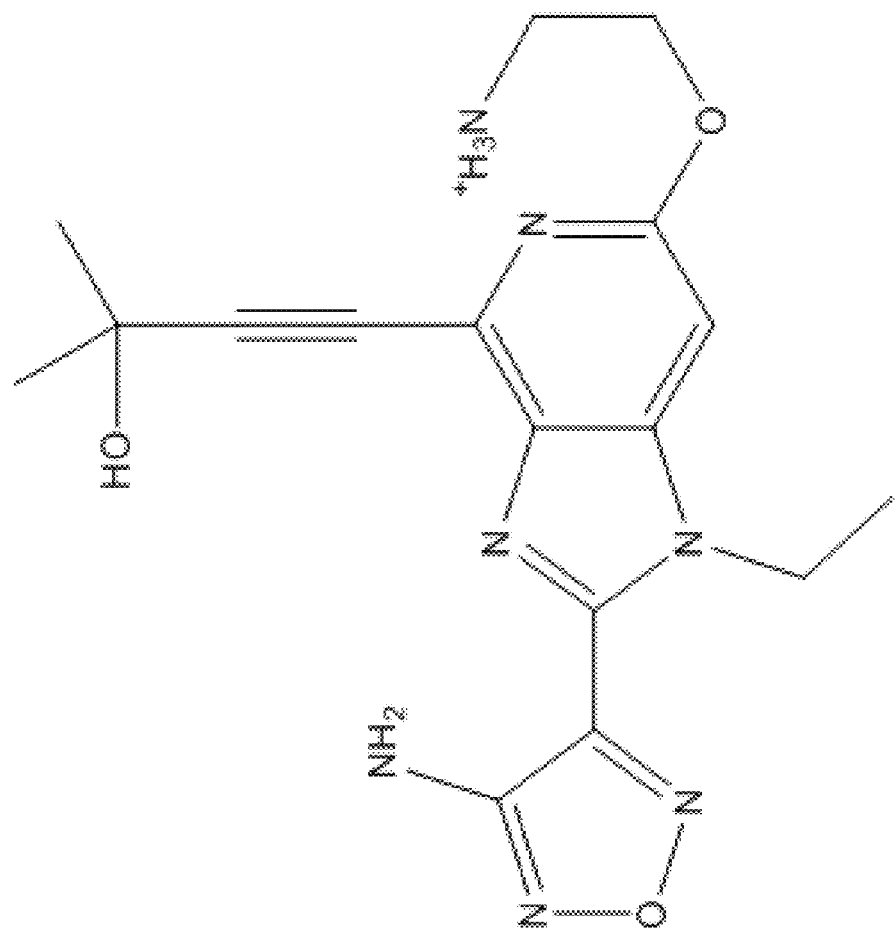
FIG. 26 shows the chemical structure of the AIA analog NW1006A270228.
Figure 27:
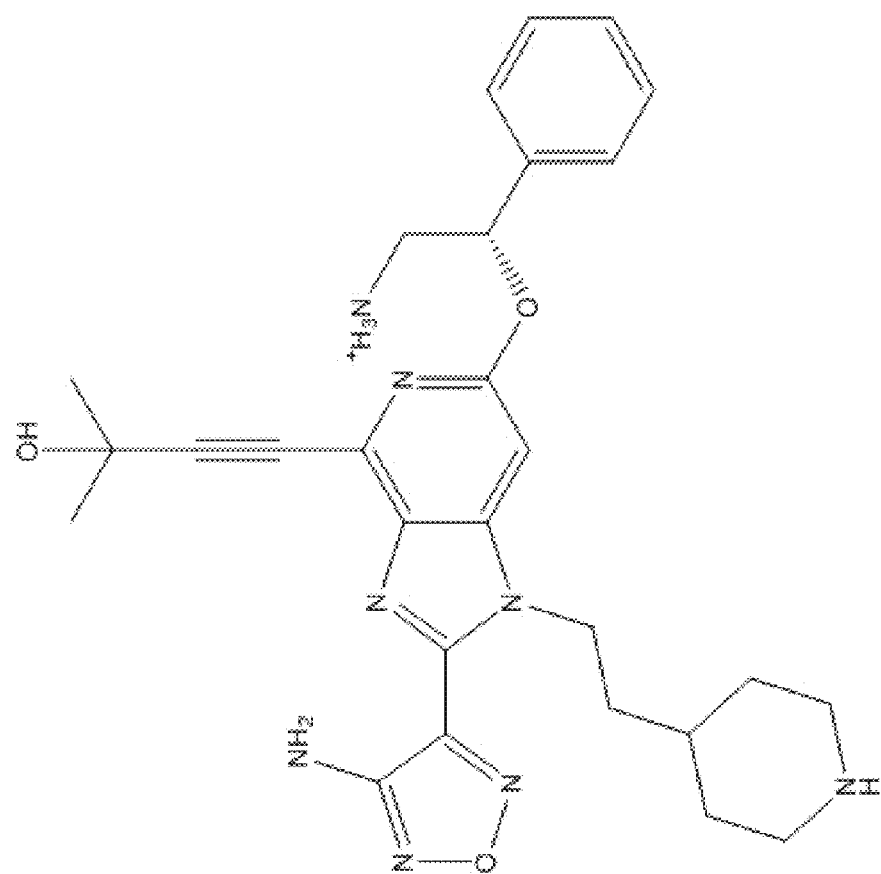
FIG. 27 shows the chemical structure of the AIA analog NW 10075676728.
Figure 28:
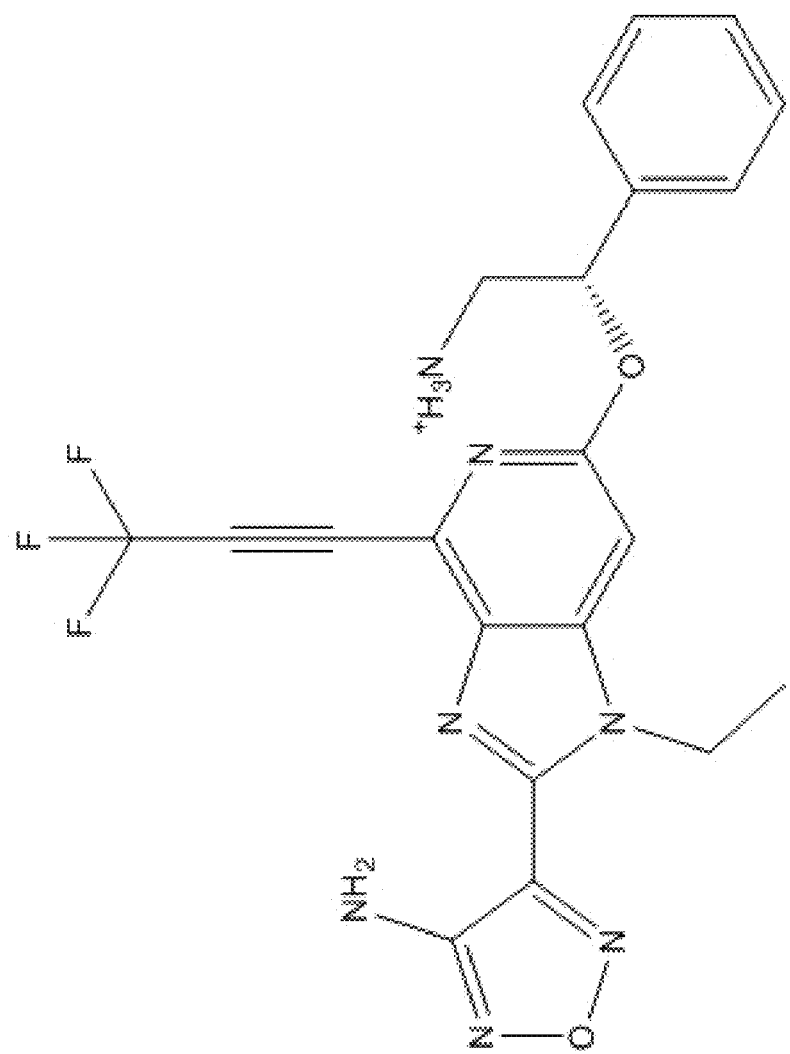
FIG. 28 shows the chemical structure of the AIA analog NW 10085670209.
Figure 29:
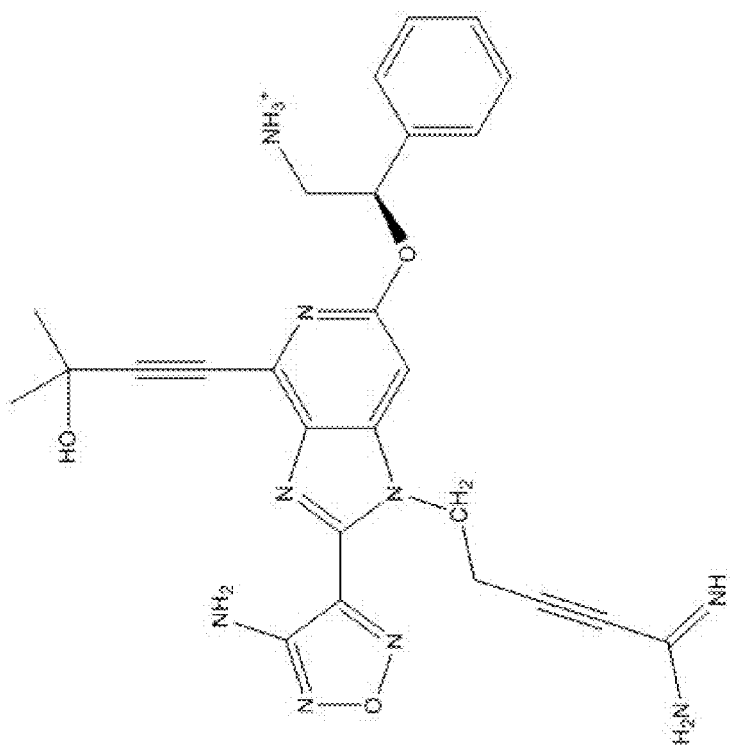
FIG. 29 shows the chemical structure of the AIA analog NW1009R674728.
Figure 30:
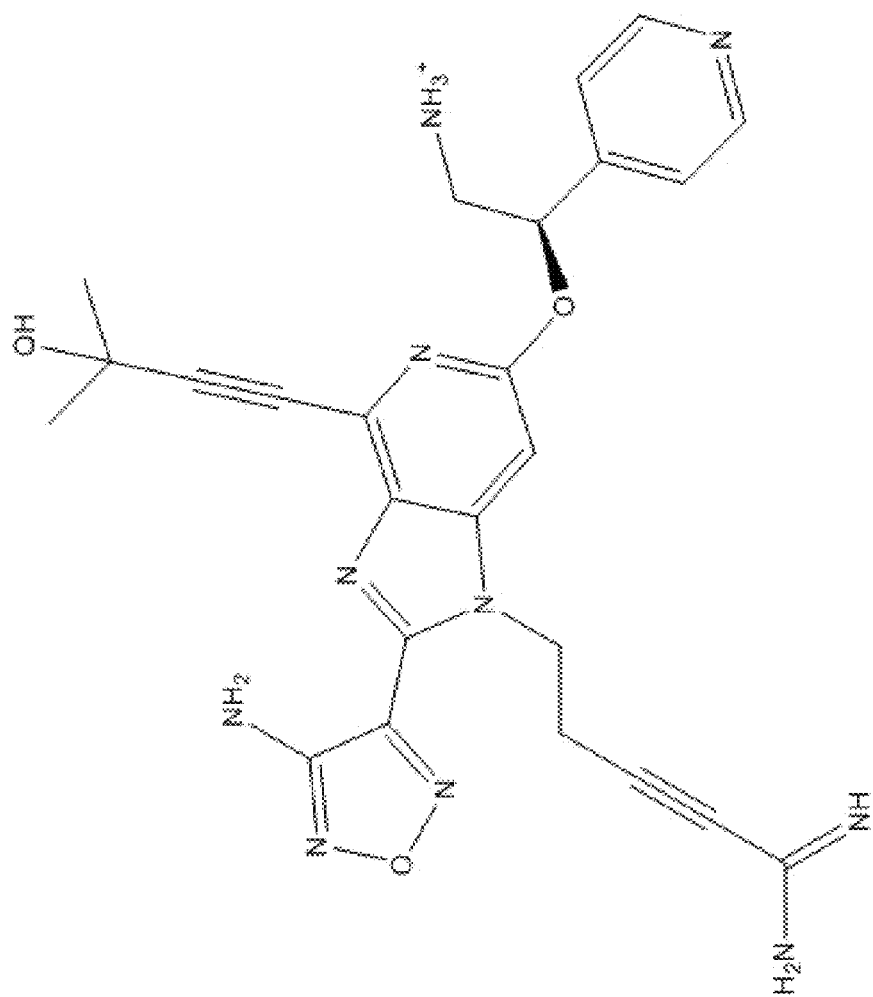
FIG. 30 shows the chemical structure of the AIA analog NW1010R674728.
Figure 31:
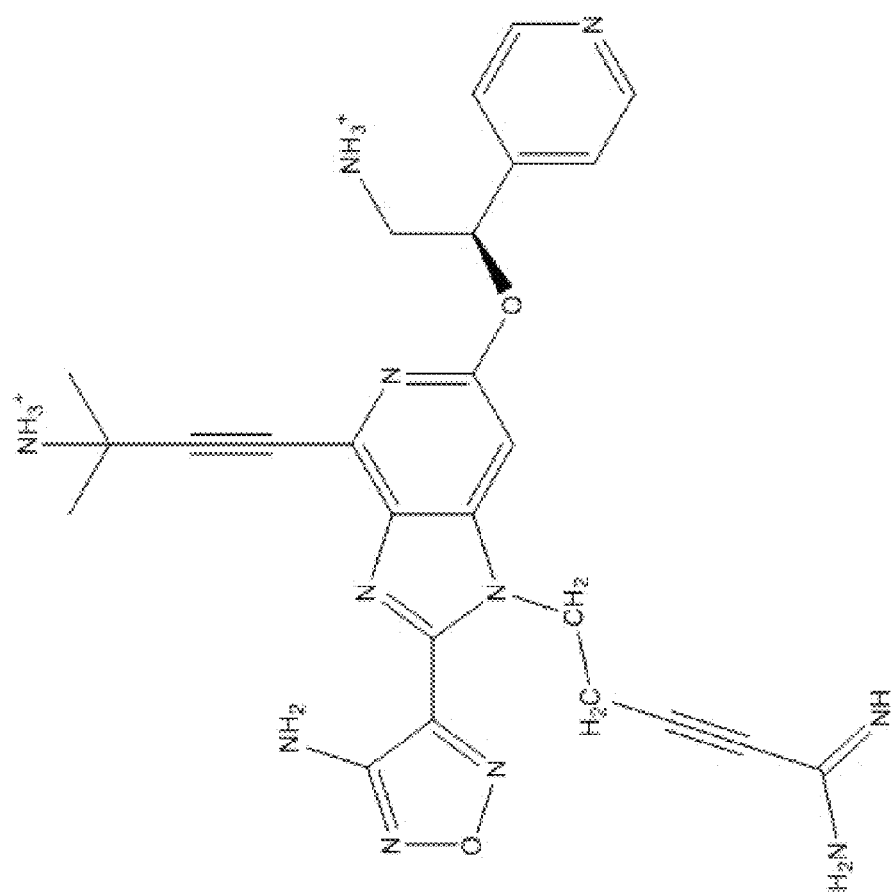
FIG. 31 shows the chemical structure of the AIA analog NW1011R674727.

For compound GSK1007102B-S (see FIG. 19), the predicted binding energy is −10.44 kcal/mol, and the predicted $K_i$ is 17 nM. For compound NW1001S674728 (see FIG. 20), the predicted binding energy is −10.60 kcal/mol, and the predicted $K_i$ is 18 nM. For compound NW1002S670203 (see FIG. 21), the predicted binding energy is −10.89 kcal/mol, and the predicted $K_i$ is 10 nM. For compound NW1003S674728 (see FIG. 22), the predicted binding energy is −11.77 kcal/mol, and the predicted $K_i$ is 2 nM. For compound NW1004674728 (see FIG. 23), the predicted binding energy is −11.43 kcal/mol, and the predicted $K_i$ is 4 nM. For compound NW1005S674728 (see FIG. 24), the predicted binding energy is −10.92 kcal/mol, and the predicted $K_i$ is 10 nM. For compound NW3001S670228 (see FIG. 25), the predicted binding energy is −9.80 kcal/mol, and the predicted $K_i$ is 66 nM. For compound NW1006A270228 (see FIG. 26), the predicted binding energy is −9.79 kcal/mol, and the predicted $K_i$ is 67 nM. For compound NW1007S676728 (see FIG. 27), the predicted binding energy is −11.76 kcal/mol, and the predicted $K_i$ is 4 nM. For compound NW1008S670209 (see FIG. 28), the predicted binding energy is −10.12 kcal/mol, and the predicted $K_i$ is 38 nM. For compound NW1009R674728 (see FIG. 29), the predicted binding energy is −13.09 kcal/mol, and the predicted $K_i$ is 0.25 nM. For compound NW1010R674728 (see FIG. 30), the predicted binding energy is −12.15 kcal/mol, and the predicted $K_i$ is 1 nM. For compound NW1011R674727 (see FIG. 31), the predicted binding energy is −11.61 kcal/mol, and the predicted $K_i$ is 3 nM.

The low $K_i$ reported for some of the analogs provides further clues as to designing compounds having increased efficacy against tuberculosis. This strategy is further explored in Example 7 below.

Example 7

Favored Substituents for Designing Optimized AIA Analogs

In this Example, we further analyzed the in silico docking data to predict specific AIA scaffold structures that favor PknB docking/binding, and thus increased efficacy in synergistic treatment of tuberculosis infections.

Figure 32:
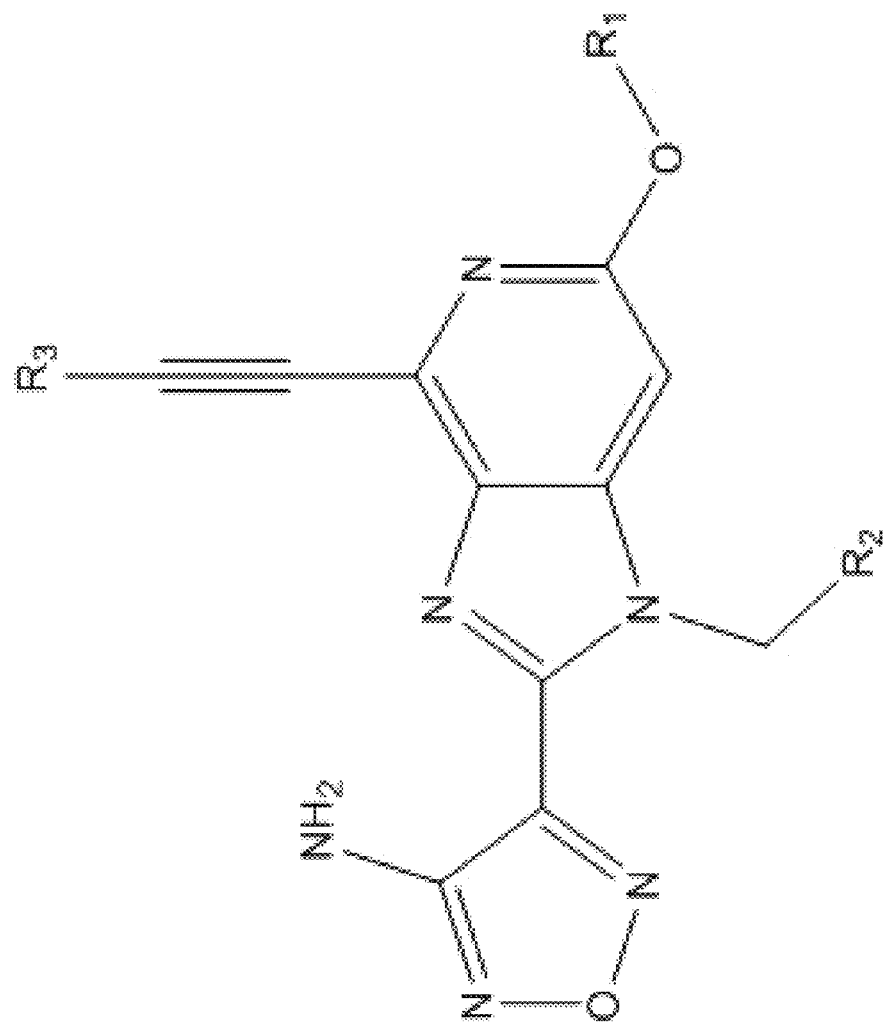
FIG. 32 shows a non-limiting chemical scaffold of AIA analogs that may be used in the disclosed method.
Figure 33:
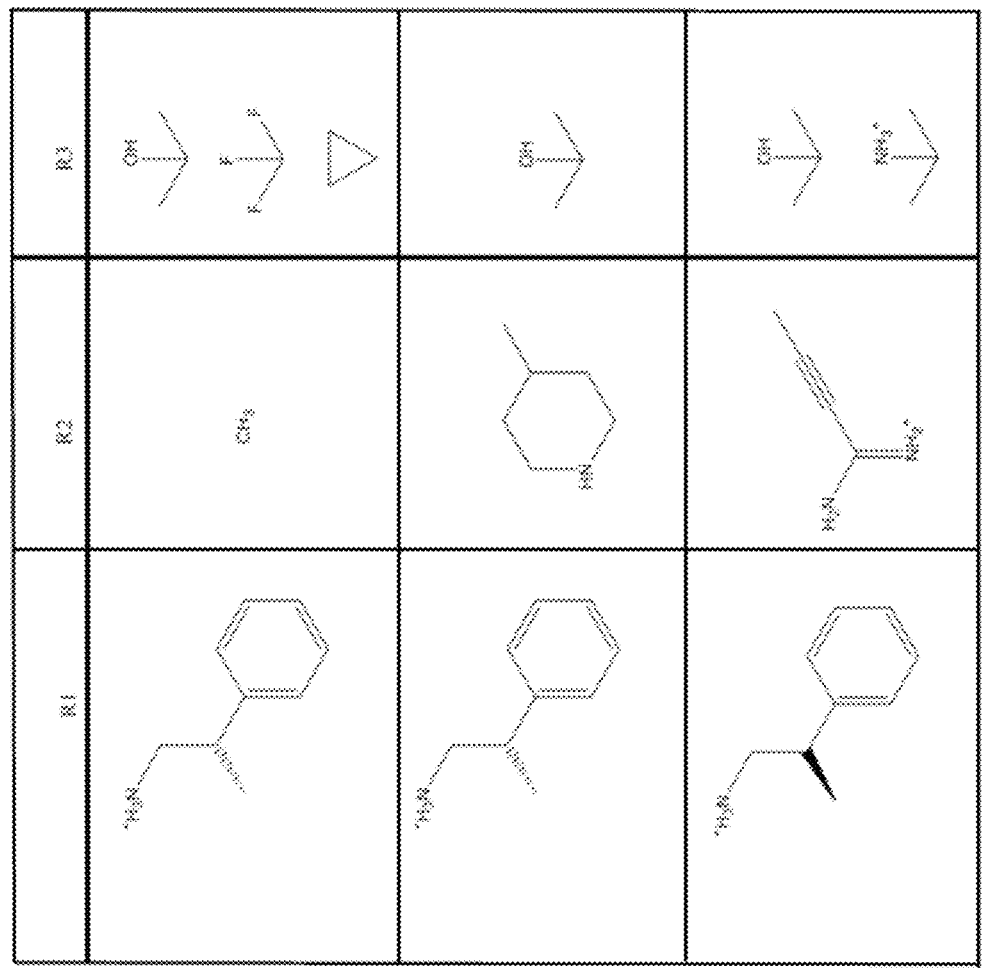
FIG. 33 illustrates non-limiting examples of R groups that may be selected in the scaffold of FIG. 32.

Specifically, based on the in silica docking data, a preferred scaffold for AIAs for use in the claimed invention appears in FIG. 32. FIG. 33 includes a table listing preferred substituents at positions $R_1$, $R_2$, and $R_3$. This Example demonstrates one non-limiting strategy that could be used to optimize the AIAs used in the disclosed method.

Example 8

Selective Pharmacologic Inhibition of a PASTA Kinase with GW779439X Increases Staphylococcus aureus Susceptibility to β-Lactam Antibiotics Abstract.

While β-lactam antibiotics are a critical part of the antimicrobial arsenal, they are frequently compromised by various resistance mechanisms including changes in penicillin binding proteins of the bacterial cell wall. Genetic deletion of the Penicillin binding protein and Serine-Threonine kinase associated protein (PASTA) kinase in Methicillin Resistant Staphylococcus aureus (MRSA) has been shown to restore β-lactam susceptibility. However, the mechanism remains unclear and whether pharmacologic inhibition would have the same effect is unknown.

In this Example, we demonstrate that pharmacologic inhibition of the PASTA kinase in Staphylococcus aureus by the selective kinase inhibitor GWX779439X results in enhanced susceptibility to cephalosporin antibiotics. Overall these results suggest that pharmacologic targeting of PASTA kinases can increase the efficacy of β-lactam antibiotics.

Introduction.

In this Example, we test the hypothesis that pharmacologic inhibition of the PASTA kinase will lead to increased β-lactam susceptibility in the Gram positive pathogen Staphylococcus aureus. We demonstrate that that combination therapy with β-lactam antibiotics and GWX779439X leads to a substantial increase in susceptibility to the β-lactam antibiotic. Taken together with our previous work, this work suggests that pharmacologic inhibition of PASTA kinases, in combination with β-lactam treatment, is a viable antibiotic development strategy.

Methods.

Figure 34:
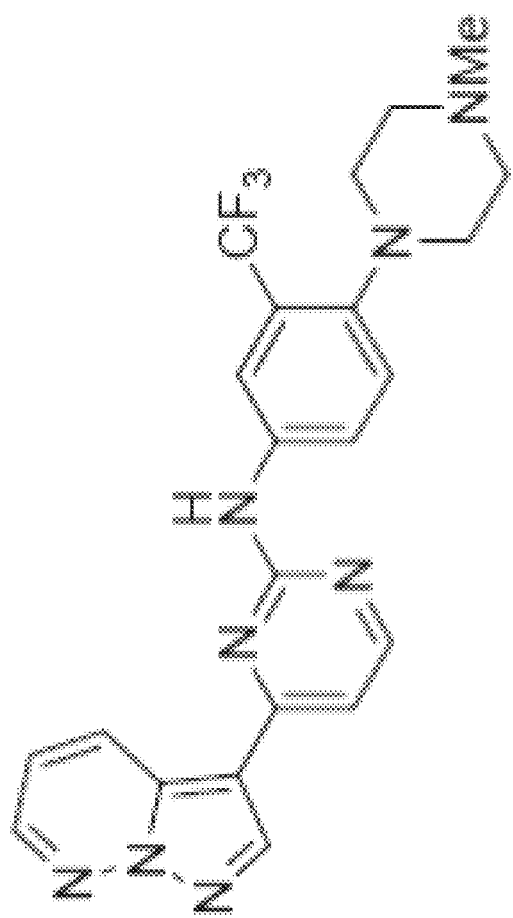
FIG. 34 shows the chemical structure of the CDK inhibitor GW779439X.

Compounds. In this Example, we used the kinase inhibitors GW778894X, GW779439X, and GW780056X, all from a library provided by GlaxoSmithKline GW778894X is deposited in the PubChem Deposited Record as SID 124349996. GW779439X, the structure of which is shown in FIG. 34, is deposited in the PubChem Deposited Record as SID 124349951. GW780056X is identified in PubChem as CID 10215776.

Antibiotics. Ceftriaxone (CTX) was purchased from Sigma Aldrich (St. Louis, Mo.) and resuspended according to the manufacturer's protocol.

Bacterial strains and Growth. Staphylococcus aureus strain USA300 LAC was used in the antibiotic treatment assays.

Broth growth curves. For in vitro growth experiments, Methicillin-resistant S. aureus (strain USA300) was grown in tryptic soy broth (TSB) at 37° C. overnight with gyratory shaking (250 rpm) to stationary phase. Overnight stationary-phase cultures were back diluted 1:100 (S. aureus). Growth was measured at optical density 600 nm ($OD_{600}$) at fifteen minute intervals over the course of 12 hours in a 96-well plate format using an Eon Microplate Spectrophotometer or Synergy HT Microplate Spectrophotometer (BioTek Instruments, Inc., Winooski, Vt.). All growth experiments were repeated at twice. For all in vitro growth assays, GW778894X, GW779439X, or GW 780056X were used at 50 μM, and antibiotics were used at a concentration of 100 1.1 g/ml.

Results

Figure 35A:
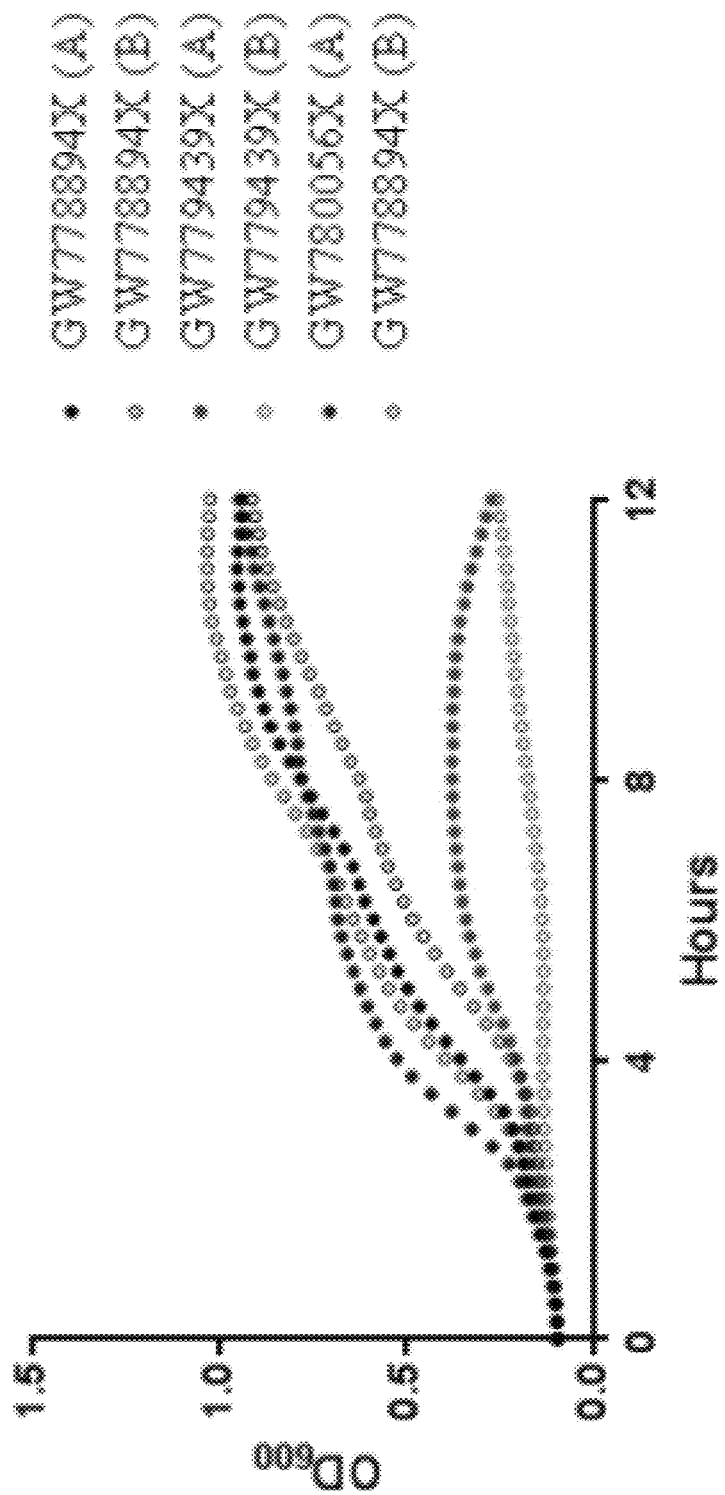
FIGS. 35A and 35B. Graphed data showing that GW779439X sensitizes S. aureus to β-lactam antibiotics. Overnight cultures of S. aureus were back diluted and treated with 100 μg/ml ceftriaxone in the presence of 1004 GW779439X, GX778894X, or GW780056X. Growth was analyzed for 12 hours at 15 minute intervals. The growth data are shown in both linear (FIG. 35A) and logarithmic (FIG. 35B) forms. Two independent repeats were performed for each compound, labeled (A) and (B) in the legends to the right of each figure. The data for the two trials using GW779439X are shown in the bottom two curves in each figure.
Figure 35B:
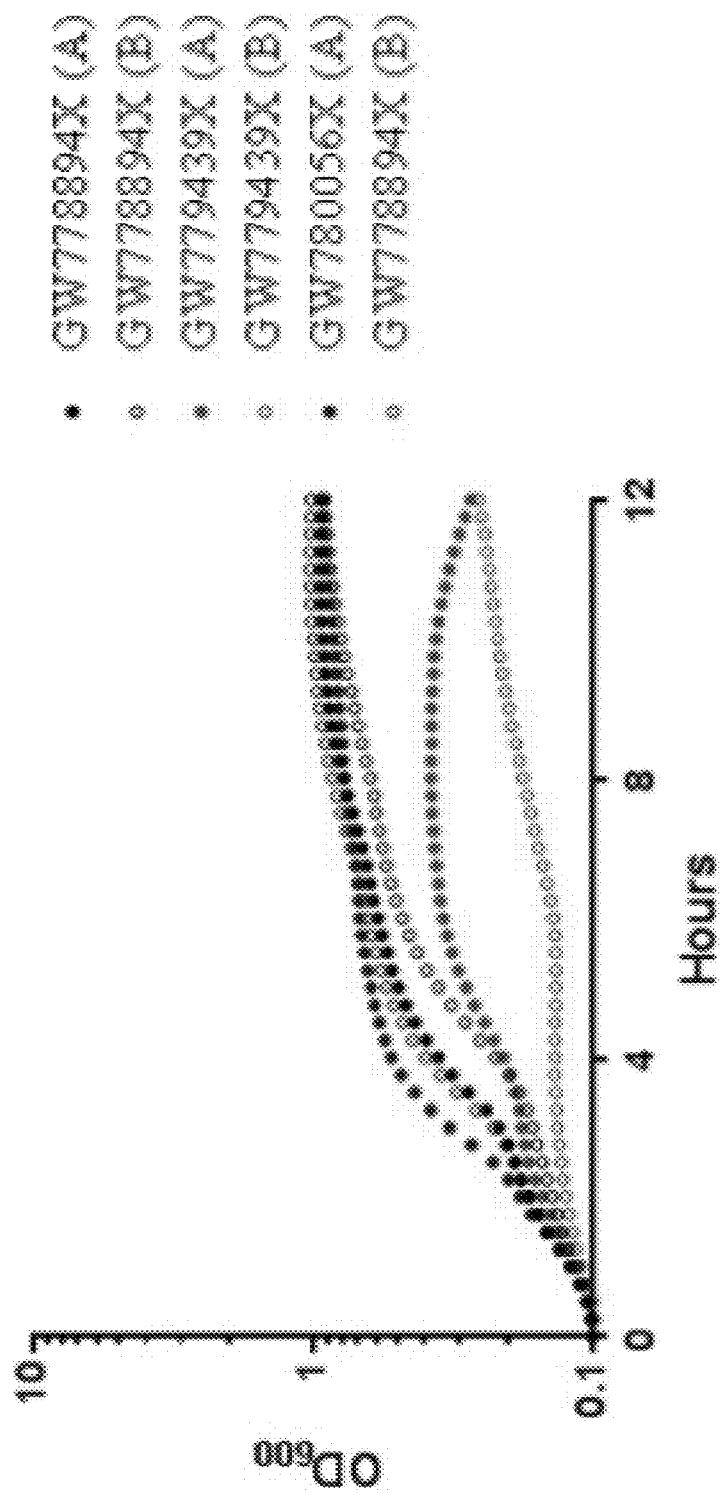

GW779439X sensitizes *Staphylococcus aureus* to β-lactam antibiotics. Deletion of the PASTA kinase in *S. aureus* or *E. faecalis* leads to an increase in susceptibility to β-lactam antibiotics. To test the hypothesis that pharmacologic inhibition of bacterial serine/threonine kinases could result in a synergistic sensitization to antibiotics we separately incubated the model Gram positive pathogens *Staphylococcus aureus* and *Listeria monocytogenes* with the three kinase inhibitors in the presence of ceftriaxone. Kinase inhibitor treatment alone had a minimal effect on growth of *Staphylococcus aureus* or *Listeria monocytogenes* (Data not shown). Similarly, sub-inhibitory concentrations of antibiotic had no effect on growth of *Staphylococcus aureus* or *Listeria monocytogenes* (Data not shown). Furthermore, treatment of *L. monocytogenes* with sub-inhibitory concentrations of β-lactam antibiotic in the presence of each of the tested kinase inhibitors did not increase susceptibility (Data not shown). However, treatment of *Staphylococcus aureus* with sub-inhibitory concentrations of β-lactam antibiotic (Ceftriaxone) in the presence of 5004 GW779439X substantially increased the susceptibility of the *S. aureus* to the tested β-lactam antibiotic (see FIGS. 35A and 35B).

Example 9

GW779439X Increases *Staphylococcus aureus* Susceptibility to β-Lactam Antibiotics in Wild Type MSRA, but not in Knockout Mutants Having a Kinase Deletion In this Example, we provide further data demonstrating that pharmacologic inhibition of the PASTA kinase in wild type *Staphylococcus aureus* by the selective kinase inhibitor GWX779439X results in enhanced susceptibility to cephalosporin antibiotics, while also providing data demonstrating that GWX779439X has no effect in deletion mutants lacking the kinase. These results are consistent with our conclusion that pharmacologic targeting of PASTA kinases can increase the efficacy of β-lactam antibiotics.

Methods.

Compounds. In this Example, we used the kinase inhibitor GW779439X from a library provided by GlaxoSmithKline GW779439X, the structure of which is shown in FIG. 34, is deposited in the PubChem Deposited Record as SID 124349951.

Antibiotics. Ceftriaxone (CTX) was purchased from Sigma Aldrich (St. Louis, Mo.) and resuspended according to the manufacturer's protocol.

Bacterial strains and Growth. *Staphylococcus aureus* strain USA300 LAC (WT USA300), and a deletion mutant lacking Stk1, the PASTA kinase of *S. aureus* (ΔStk1 USA 300), were used in the antibiotic treatment assays.

Broth growth curves. For in vitro growth experiments, Methicillin-resistant *S. aureus* (WT USA300) and the Stk1 deletion mutant (ΔStk1 USA 300) were each grown in tryptic soy broth (TSB) at 37° C. overnight with gyratory shaking (250 rpm) to stationary phase. Overnight stationary-phase cultures were back diluted 1:100 (*S. aureus*). Growth was measured at optical density 600 nm ($OD_{600}$) at fifteen minute intervals over the course of 12 hours in a 96-well plate format using an Eon Microplate Spectrophotometer or Synergy HT Microplate Spectrophotometer (BioTek Instruments, Inc., Winooski, Vt.). Ceftrioxone was used at concentrations of 0, 4, 8, 16, 32, 64, and 128 µM. Each of these concentrations were assayed with (GW) and without (DMSO) GW779439X at a concentration of 2 µM.

Results

Figure 36:
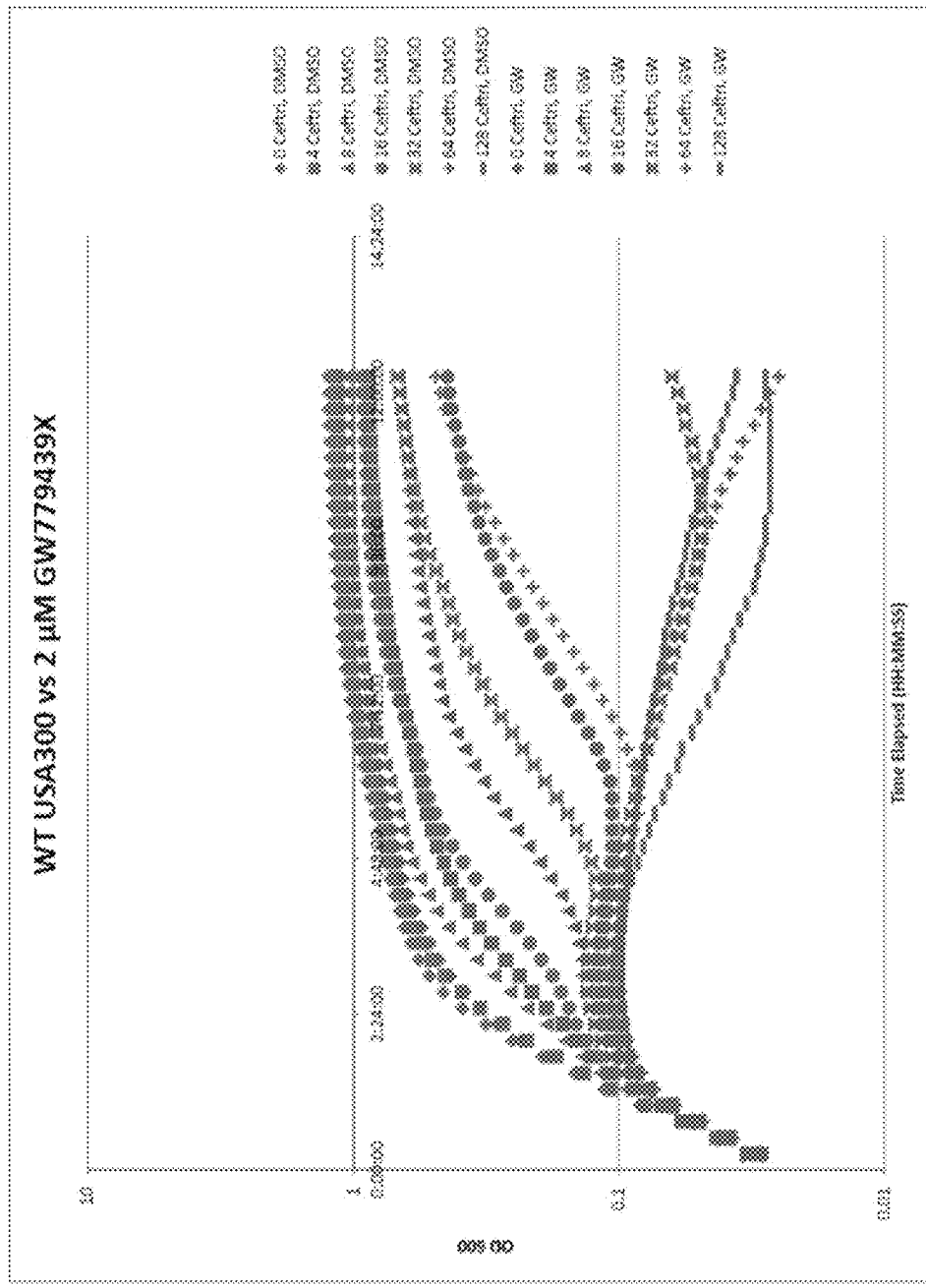
FIG. 36. Graphed data demonstrating that GW779439X sensitizes wild type S. aureus (MRSA WT USA300) to various dosages of the β-lactam antibiotic ceftriaxone. Overnight cultures of S. aureus were back diluted and treated with 0, 4, 8, 16, 32, 64, or 128 μg/ml ceftriaxone in the presence (GW) or absence (DMSO) of 2 μM GW779439X. Growth was analyzed for 12 hours at 15 minute intervals. The growth data are shown in logarithmic form.

GW779439X at various concentrations sensitizes wild type *staphylococcus aureus* to β-lactam antibiotics. As shown in FIG. 36, treatment of WT *Staphylococcus aureus* with sub-inhibitory concentrations of β-lactam antibiotic (Ceftriaxone) in the presence of 2 µM GW779439X substantially increased the susceptibility of the WT strain to the β-lactam antibiotic.

Figure 37:
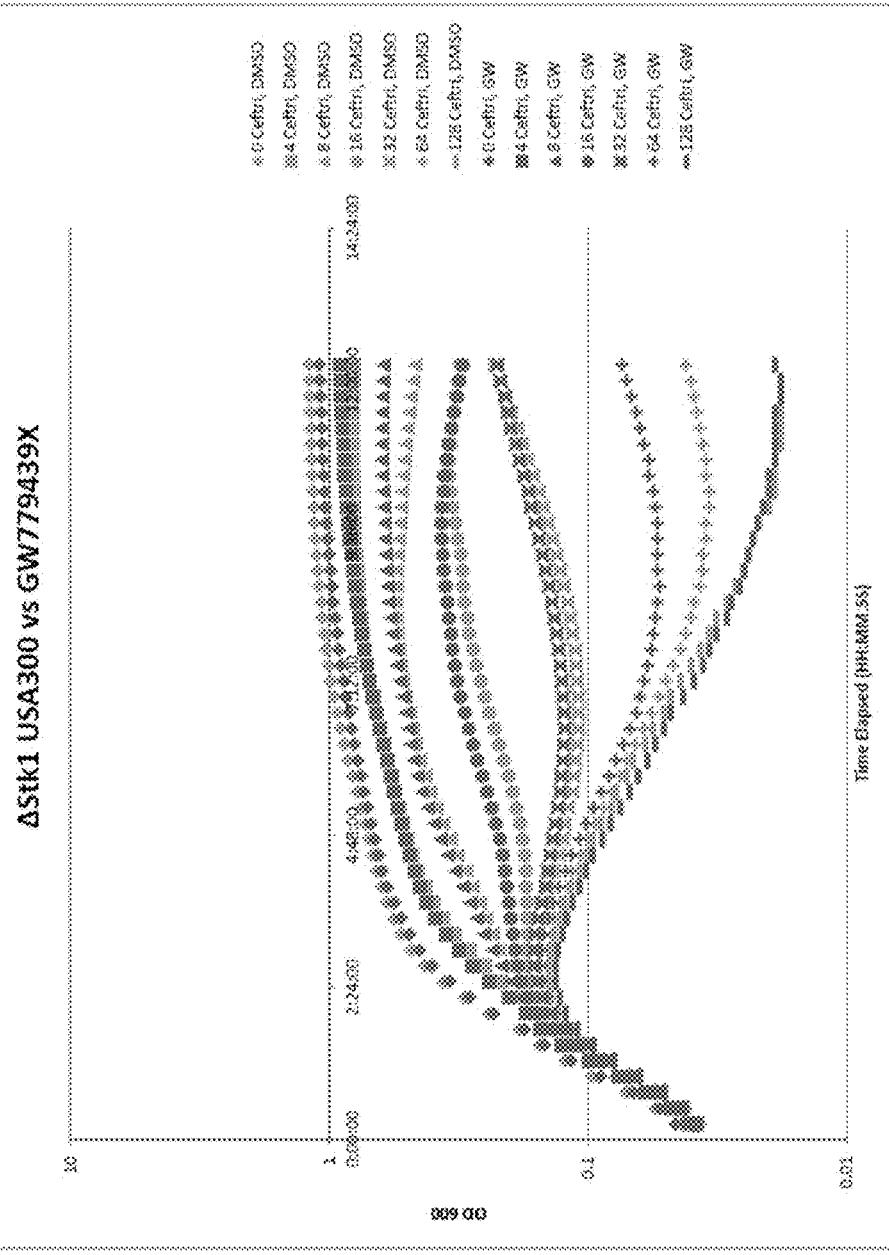
FIG. 37. Graphed data demonstrating that GW779439X does not sensitize S. aureus knockout mutants having a kinase deletion (MRSA ΔStk1 USA300) to the β-lactam antibiotic ceftriaxone. Overnight cultures of ΔStk1 S. aureus were back diluted and treated with 0, 4, 8, 16, 32, 64, or 128 μg/ml ceftriaxone in the presence (GW) or absence (DMSO) of 2 μM GW779439X. Growth was analyzed for 12 hours at 15 minute intervals. The growth data are shown in logarithmic form.

GW779439X does not sensitize the *Staphylococcus aureus* Stk1 deletion mutant to β-lactam antibiotics. As shown in FIG. 37, treatment of ΔStk1 *Staphylococcus aureus* with sub-inhibitory concentrations of β-lactam antibiotic (Ceftriaxone) in the presence of 2 µM GW779439X did not significantly affect the susceptibility of the knockout strain to the β-lactam antibiotic. This is consistent with the proposed mechanism of action of GW779439X, in that the ΔStk1 strain has no PASTA kinase that can potentially be targeted by GW779439X.

Example 10

Repurposing the Pyrazolo[1,5b]Pyridazine Kinase Inhibitor Scaffold with Minimal Human Activity for Use in a General Antibiotic Pathway In this prophetic Example, we provide strategies for generating GWX779439X analogs that are optimized for human use.

We will test related compounds designed by us to optimize activity for bacterial over human kinases against a panel of bacterial and human kinases. Each compound will also be tested in microbial assays against Methicillin Resistant *Staphylococcus aureus* (MRSA) and a mycobacterial species and for toxicity in zebrafish. The single best inhibitor (high bacterial inhibitory activity/low human CDK2 activity) will be co-crystallized with the corresponding bacterial kinase and the crystal structure solved.

We have demonstrated that GW779439X is active against MRSA at 1 µM (GW779439X) and *Mycobacterium smegmatis* at <10 µM. Using related analogs, we will perform biochemical and structural analysis to improve bacterial activity while simultaneously "deoptimizing" them for human kinases, particularly human cyclin dependent kinases (CDKs) and Glycogen Synthase kinase 3 (GSK3), which are all members of a specific, structurally related family of human kinases.

Figure 38:
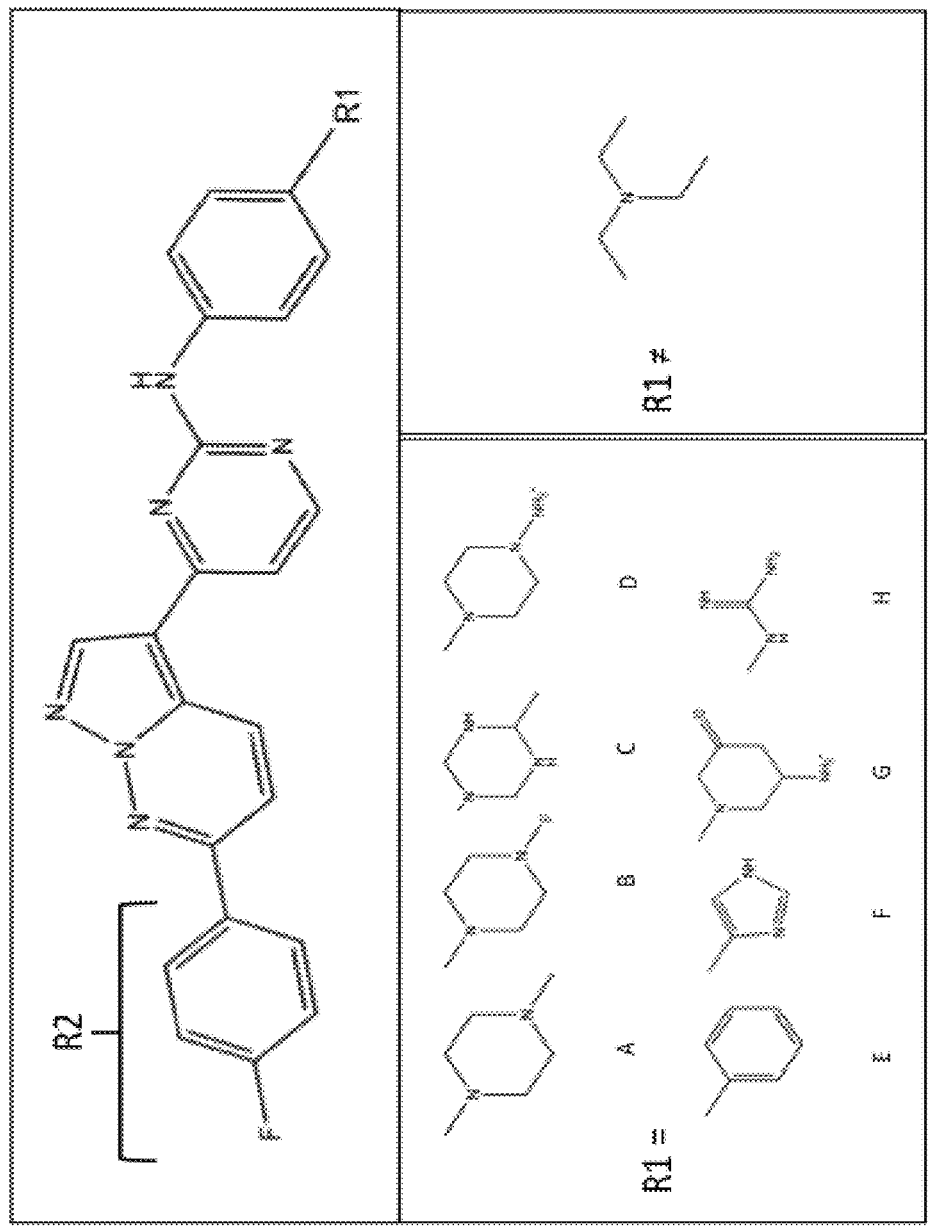
FIG. 38 shows a non-limiting chemical scaffold for analogs of compound 39 that may be used in the disclosed method. Compound 39 is in the top box and differs from GW779439X by the addition of R1 and R2 substituents. The R2 group will be kept constant, since the data suggests this decreases human kinase activity. Hence, we will explore different R1 groups. The bottom right shows an R1 group that does not have antibacterial activity. Bottom left: A represents the R2 group of compound 39 and B-H shows other possible substituents that according to modeling will improve activity against MRSA, tuberculosis or both.

We have selected the GW779439X from the pyrazolo[1,5-b]pyridazine scaffold to focus on because (1) GW779439X has microbiologic activity against MRSA; (2) GW779439X has biochemical activity against both the MRSA and tuberculosis kinases; (3) GW779439X has MRSA activity but only when the kinase target is present; and (4) published data and our in silico analysis the human activity can be "deoptimized" without compromising the antibacterial activity by modifications at R2 (see FIG. 38).

4-{3-(p-Fluorophenyl)-1.2.9-triazabicyclo[4.3.0]nona-2,4,6,8-tetraen-7-yl}-2-pyrimidinyl)[p-(4-methyl-1-piperazinyl)phenyl]amine can be synthesized from the pyrazolo[1,5-b]pyridazine), (R1A, FIG. 3, referred to here as 39), as well as several modifications. Compound 39 and the pyrazolo[1,5-b]pyridazine scaffold in general were chosen because only some of the analogs in this SAR were active against MRSA and substituents at R2 (FIG. 3) increased activity for biochemical and microbiologic activity, but decreased activity for human kinases. We have docked all 41 compounds in this SAR into crystal structures for both the MRSA kinase (Stk1) as well as the tuberculosis kinase (PknB), 39 models even better with the mycobacterial kinase than with the staph kinase. Our docking predicts that compound 39 relative to GW779439X drops from ~3 μM Ki to the nM range. The addition of R2 alone to GW779439X is predicted to lower the binding energy from −9.6 kcal/mol to −11 kcal/mol.

Figure 39A:
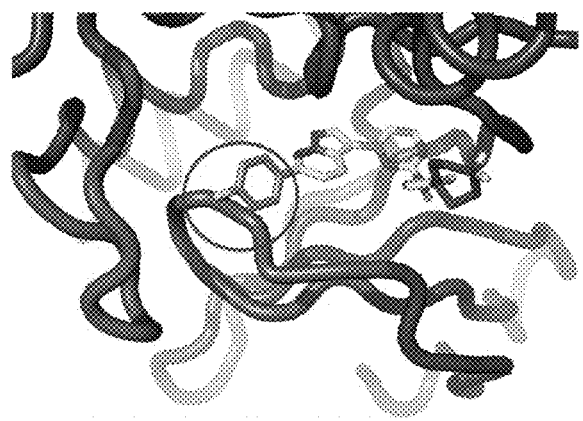
FIGS. 39A-C show modeling studies for compound 39. Compound 39 modeled in the active site of the tuberculosis kinase (FIG. 39A) and 39 modeled on ribbon diagrams of tuberculosis kinase (FIG. 39B) and the human kinase CDK2 (FIG. 39C).
Figure 39B:
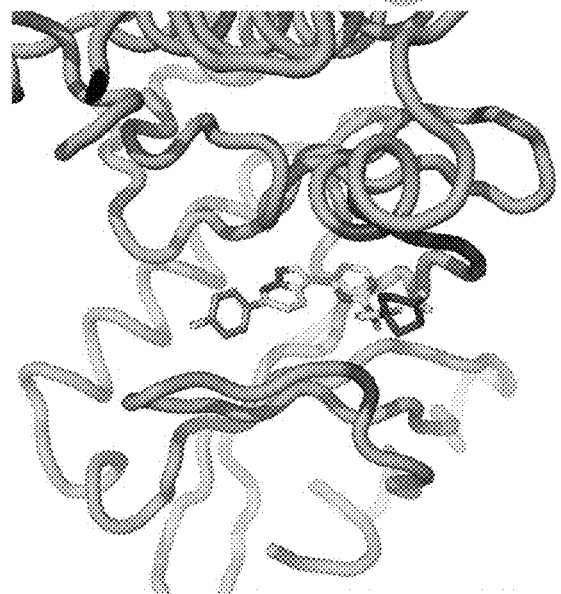
Figure 39C:
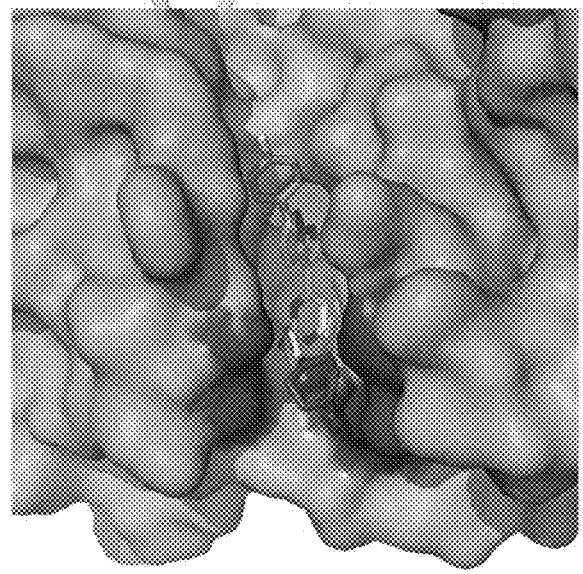

The proposed modifications of compounds 39 were based on our model of the bacterial kinase and, most importantly, the co-crystal structure of the human CDK2 bound to pyrazolo[1,5-b]pyridazine. Using both structures allows us to destabilize the human interaction, which is as critical for our success in making pathogenic specific inhibitors as is improving bacterial kinase binding (see FIG. 39).

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents (including enentiomers) of these exemplary embodiments. All technical publications, patents and published patent applications cited herein are hereby incorporated by reference in their entirety for all purposes.

What is claimed is:

1. A method of treating a Gram positive bacterial infection in a subject in need thereof, comprising administering to said subject an effective amount of a compound having the chemical structure:

(a)

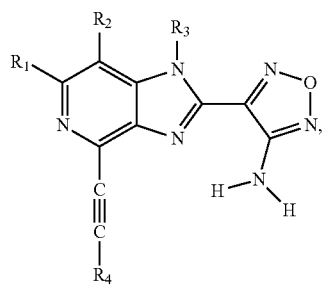

wherein one of $R_1$ and $R_2$ is H;
wherein the other of $R_1$ and $R_2$ is —OX, wherein X is selected from the group consisting of

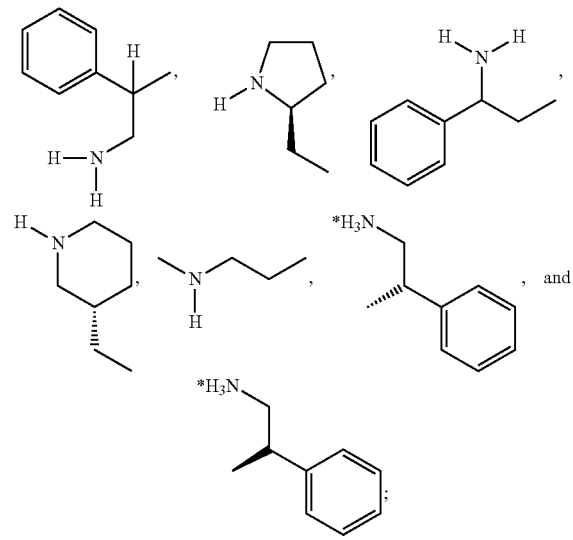

wherein $R_3$ is selected from the group consisting of —CH$_2$CH$_3$,

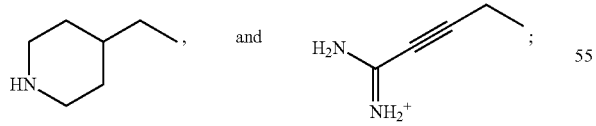

and wherein $R_4$ is selected from the group consisting of

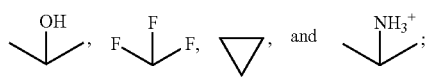

or a pharmaceutically acceptable salt.

2. The method of claim 1, wherein the compound administered has the structure:

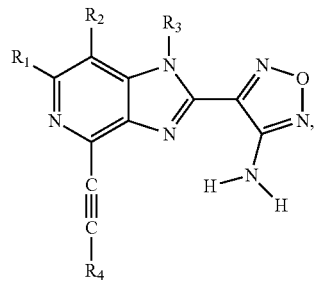

3. The method of claim 2, wherein $R_3$ is —CR$_2$CH$_3$ and $R_4$ is

4. The method of claim 2, wherein X is selected from the group consisting of:

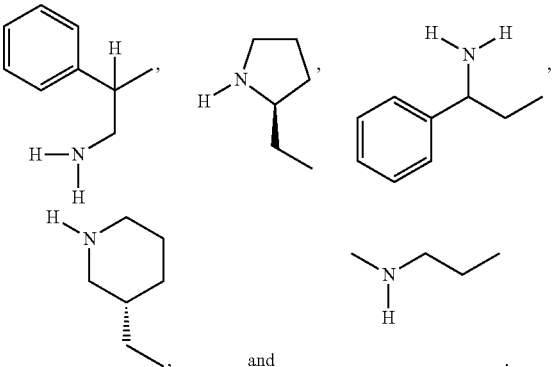

5. The method of claim 2, wherein the compound administered is selected from the group consisting of:

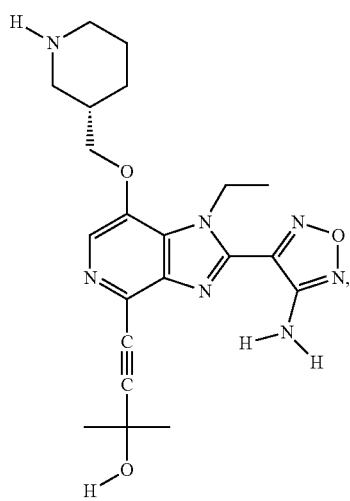

-continued

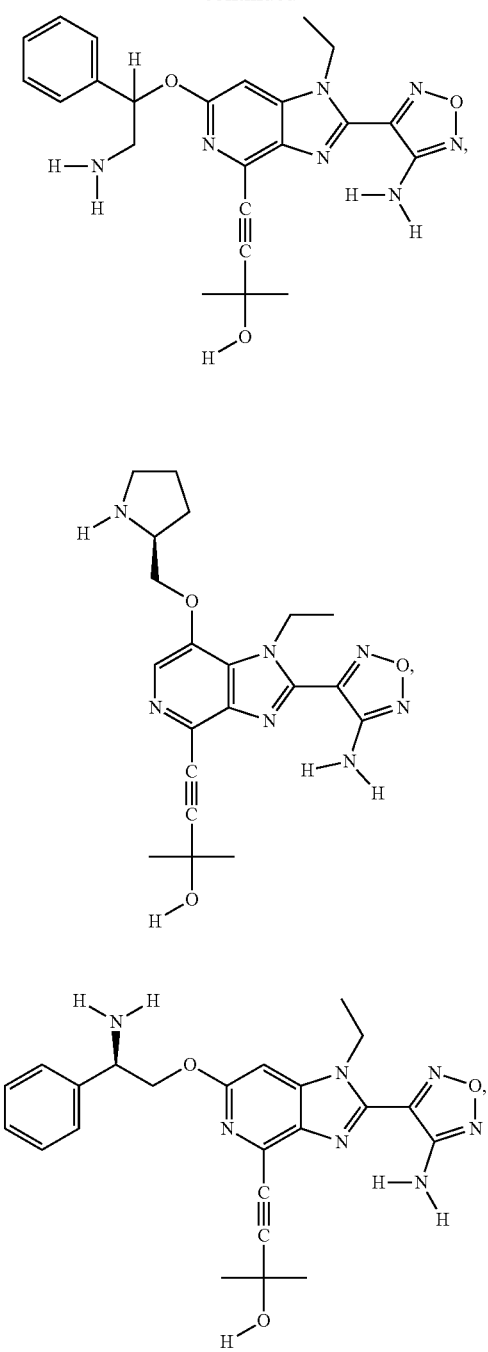

-continued

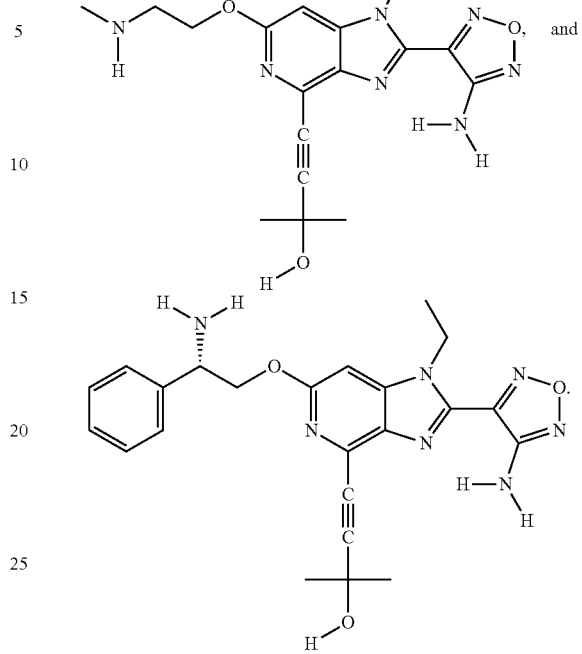

6. The method of claim 1, wherein the Gram positive bacterial infection is caused by *Listeria monocytogenes, Staphylococcus aureus, Streptococcus pneumonia, Mycobacterium tuberculosis, Nocardia* farcinia, a *Clostridium*, or an enteroccci.

7. The method of claim 6, wherein the Gram positive bacterial infection is caused by *Listeria monocytogenes, Mycobacterium tuberculosis*, or Methicillin Resistant *Staphylococcus aureus* (MSRA).

8. The method of any of claim 1, further comprising the step of administering a β-lactam antibiotic to the subject.

9. The method of claim 7, wherein the β-lactam antibiotic is selected from the group consisting of benzathine penicillin, benzylpenicillin (penicillin G), phenoxymethylpenicillin (penicillin V), procaine penicillin, methicillin, oxacillin, nafcillin, cloxacillin, dicloxacillin, flucloxacillin, temocillin, amoxicillin, ampicillin, co-amoxiclav, azlocillin, carbenicillin, ticarcillin, mezlocillin, piperacillin, cephalosporins, cephalexin, cephalothin, cefazolin, cefaclor, cefuroxime, cefamandole, cephamycins, cefotetan, cefoxitin, ceftriaxone, cefotaxime, cefpodoxime, cefixime, ceftazidime, cefepime, cefpirome, imipenem, meropenem, ertapenem, faropenem, doripenem, monobactams, aztreonam, tigemonam, nocardicin A, and tabtoxinine-P-lactam.

\* \* \* \* \*

UNITED STATES PATENT AND TRADEMARK OFFICE
CERTIFICATE OF CORRECTION

PATENT NO. : 9,540,369 B2
APPLICATION NO. : 14/695813
DATED : January 10, 2017
INVENTOR(S) : Robert Todd Striker, John-Demian Sauer and Nathan Wlodarchak Page 1 of 1

It is certified that error appears in the above-identified patent and that said Letters Patent is hereby corrected as shown below:

In the Claims

In Claim 3, at Column 38, Line 17, "-CR2CH3" should read -- -CH2CH3--.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 10

<210> SEQ ID NO 1
<211> LENGTH: 34
<212> TYPE: DNA
<213> ORGANISM: Artificial Sequence
<220> FEATURE:
<223> OTHER INFORMATION: PCR Primer

<400> SEQUENCE: 1
ggccgggccc ggaaatcata aaaaatttat ttgc                                      34

<210> SEQ ID NO 2
<211> LENGTH: 44
<212> TYPE: DNA
<213> ORGANISM: Artificial Sequence
<220> FEATURE:
<223> OTHER INFORMATION: PCR Primer

<400> SEQUENCE: 2
cttaatcgct taccaatcat catcttgttg ttacctcctt agca                           44

<210> SEQ ID NO 3
<211> LENGTH: 44
<212> TYPE: DNA
<213> ORGANISM: Artificial Sequence
<220> FEATURE:
<223> OTHER INFORMATION: PCR Primer

<400> SEQUENCE: 3
tgctaaggag gtaacaacaa gatgatgatt ggtaagcgat taag                           44

<210> SEQ ID NO 4
<211> LENGTH: 32
<212> TYPE: DNA
<213> ORGANISM: Artificial Sequence
<220> FEATURE:
<223> OTHER INFORMATION: PCR Primer

<400> SEQUENCE: 4
ggccctcgag taatttggat aagggactgt ac                                        32

<210> SEQ ID NO 5
<211> LENGTH: 44
<212> TYPE: DNA
<213> ORGANISM: Artificial Sequence
<220> FEATURE:
<223> OTHER INFORMATION: PCR Primer

<400> SEQUENCE: 5
```
atattatgga tccatgatga ttggtaagcg attaagcgat cgat                                44

<210> SEQ ID NO 6
<211> LENGTH: 57
<212> TYPE: DNA
<213> ORGANISM: Artificial Sequence
<220> FEATURE:
<223> OTHER INFORMATION: PCR Primer

<400> SEQUENCE: 6
attatacaat tgtttctttt tcttgctcat ttttttcttt tcttatctt ttttctc                   57

<210> SEQ ID NO 7
<211> LENGTH: 48
<212> TYPE: DNA
<213> ORGANISM: Artificial Sequence
<220> FEATURE:
<223> OTHER INFORMATION: PCR Primer

<400> SEQUENCE: 7
atattatgga tccatgggag aaatgacact tgcttttata gaagaaca                            48

<210> SEQ ID NO 8
<211> LENGTH: 34
<212> TYPE: DNA
<213> ORGANISM: Artificial Sequence
<220> FEATURE:
<223> OTHER INFORMATION: PCR Primer

<400> SEQUENCE: 8
attatacaat tggccctctg ttggtgggct gaat                                           34

<210> SEQ ID NO 9
<211> LENGTH: 33
<212> TYPE: DNA
<213> ORGANISM: Artificial Sequence
<220> FEATURE:
<223> OTHER INFORMATION: PCR Primer

<400> SEQUENCE: 9
taggatccat gataggtaaa ataataaatg aac                                            33

<210> SEQ ID NO 10
<211> LENGTH: 39
<212> TYPE: DNA
<213> ORGANISM: Artificial Sequence
<220> FEATURE:
<223> OTHER INFORMATION: PCR Primer

<400> SEQUENCE: 10
tatagaattc ttatcgtgtt gatttctttt taggttttg                                      39